(12) United States Patent
Dai et al.

(10) Patent No.: US 11,090,335 B2
(45) Date of Patent: Aug. 17, 2021

(54) CHIMERIC ANTIGEN RECEPTOR TARGETING HUMAN NKG2DL AND METHODS OF PREPARING SAID RECEPTOR AND PHARMACEUTICAL COMPOSITION

(71) Applicant: NANJING KAEDI BIOTHERAPEUTICS LTD., Nanjing (CN)

(72) Inventors: Hongjiu Dai, Shanghai (CN); Bin Sun, Kunming (CN); Xudong Zhao, Shanghai (CN)

(73) Assignee: NANJING KAEDI BIOTHERAPEUTICS LTD., Nanjing (CN)

( * ) Notice: Subject to any disclaimer, the term of this patent is extended or adjusted under 35 U.S.C. 154(b) by 435 days.

(21) Appl. No.: 16/116,953

(22) Filed: Aug. 30, 2018

(65) Prior Publication Data

US 2018/0369285 A1   Dec. 27, 2018

Related U.S. Application Data

(63) Continuation-in-part of application No. PCT/CN2018/075389, filed on Feb. 6, 2018.

(30) Foreign Application Priority Data

Mar. 15, 2017  (WO) ................. PCT/CN2017/076795

(51) Int. Cl.
| | | |
|---|---|---|
| *C12N 15/11* | (2006.01) | |
| *A61P 35/00* | (2006.01) | |
| *C07K 14/705* | (2006.01) | |
| *C12N 15/63* | (2006.01) | |
| *A61K 35/17* | (2015.01) | |
| *C07K 14/725* | (2006.01) | |
| *C12N 15/62* | (2006.01) | |
| *A61K 9/00* | (2006.01) | |
| *C07K 14/47* | (2006.01) | |
| *C12N 5/16* | (2006.01) | |
| *A61P 37/06* | (2006.01) | |
| *C12N 5/0783* | (2010.01) | |
| *A61K 39/00* | (2006.01) | |

(52) U.S. Cl.
CPC ............ *A61K 35/17* (2013.01); *A61K 9/0019* (2013.01); *A61K 39/001112* (2018.08); *A61P 35/00* (2018.01); *A61P 37/06* (2018.01); *C07K 14/4726* (2013.01); *C07K 14/7051* (2013.01); *C07K 14/7056* (2013.01); *C07K 14/70517* (2013.01); *C07K 14/70578* (2013.01); *C12N 5/0636* (2013.01); *C12N 5/163* (2013.01); *C12N 15/111* (2013.01); *C12N 15/62* (2013.01); *C12N 15/625* (2013.01); *C12N 15/63* (2013.01); *A61K 2039/5156* (2013.01); *A61K 2039/5158* (2013.01); *A61K 2039/80* (2018.08); *A61K 2039/812* (2018.08); *A61K 2039/828* (2018.08); *A61K 2039/844* (2018.08); *A61K 2039/852* (2018.08); *A61K 2039/86* (2018.08); *A61K 2039/884* (2018.08); *A61K 2039/892* (2018.08); *C07K 2319/00* (2013.01); *C07K 2319/02* (2013.01); *C07K 2319/03* (2013.01); *C07K 2319/32* (2013.01); *C07K 2319/33* (2013.01); *C12N 2510/00* (2013.01); *C12N 2740/16043* (2013.01)

(58) Field of Classification Search
CPC .. A61K 35/17; A61K 9/0019; C07K 14/7051; C07K 14/70517; C12N 15/111; C12N 15/625; C12N 15/63; C12N 5/163; A61P 35/00; A61P 37/06
See application file for complete search history.

(56) References Cited

U.S. PATENT DOCUMENTS 10,836,999 B2 * 11/2020 Campana ............. C12N 5/0646

FOREIGN PATENT DOCUMENTS

| CN | 102361646 A | 2/2012 |
|---|---|---|
| CN | 105001333 A | 10/2015 |
| CN | 106279438 A | 1/2017 |
| CN | 106480097 A | 3/2017 |

OTHER PUBLICATIONS

Tang X-Y et al. (2016) BMJ Open;6:e013904. pp. 1-7. (doi:10.1136/bmjopen-2016-013904).*

(Continued)

*Primary Examiner* — Robert S Landsman
(74) *Attorney, Agent, or Firm* — Bayramoglu Law Offices LLC

(57) ABSTRACT

A chimeric antigen receptor targeting to human NKG2DL, its encoding sequence, and its modified immune response cells, and the preparation and application thereof are provided. This invention constructs a chimeric antigen receptor targeting to NKG2DL and its modified immune response cell based on the NKG2D molecule. The amino acid sequence of the chimeric antigen receptor targeting the human NKG2DL is sequentially connected by the following amino acid sequences from an amino terminal to a carboxy terminal: an amino acid sequence of a guiding sequence, an amino acid sequence of human NKG2D, an amino acid sequence of a human CD8 hinge region, an amino acid sequence of a human CD8 transmembrane region, an amino acid sequence of a human 4-1BB intracellular domain and an amino acid sequence of a human CD3 zeta domain.

7 Claims, 35 Drawing Sheets
Specification includes a Sequence Listing.

(56) References Cited

OTHER PUBLICATIONS

De-Gang Song et al. "Chimeric NKG2D Car-Expressing T Cell-Mediated Attack of Human Ovarian Cancer Is Enhanced by Histone Deacetylase Inhibition", Human Gene Therapy, 24:295-305 (Mar. 2013).
Charles L. Sentman et al. "NKG2D CARs as Cell Therapy for Cancer", Cancer Journal, Dec. 31, 2014 ; 20(2): 156-159.
Manfred Lehner et al. "Redirecting T Cells to Ewing's Sarcoma Family of Tumors by a Chimeric NKG2D Receptor Expressed by Lentiviral Transduction or mRNA Transfection", PLoS One, Feb. 2012, vol. 7, Issue 2.

\* cited by examiner

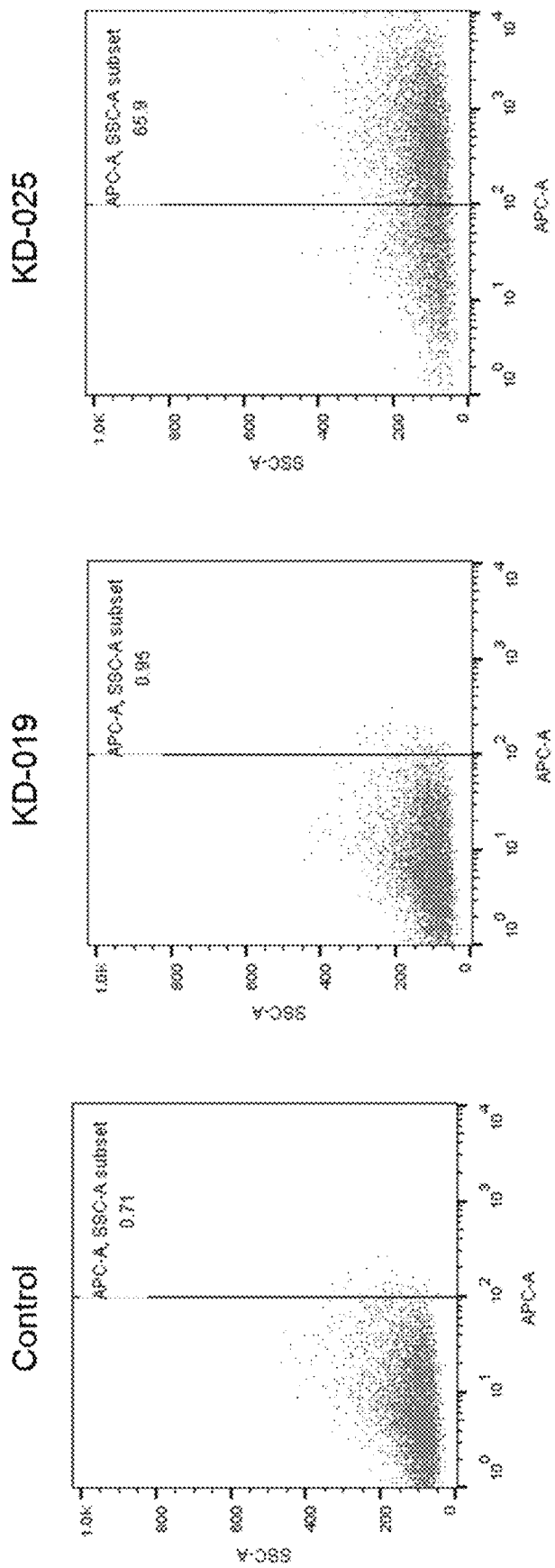

CHIMERIC ANTIGEN RECEPTOR TARGETING HUMAN NKG2DL AND METHODS OF PREPARING SAID RECEPTOR AND PHARMACEUTICAL COMPOSITION

CROSS REFERENCE TO RELATED APPLICATIONS

This application is the Continuation-in-part of International Application No. PCT/CN2018/075389, filed on Feb. 6, 2018, which is based upon and claims priority to PCT Patent Application No. PCT/CN2017/076795, filed Mar. 15, 2017, the entire contents of which are incorporated by reference.

TECHNICAL FIELD

The invention belongs to the field of tumor immunotherapy biological medicine technology and involves specific chimeric antigen receptor T cells. In particular, it relates to a specific targeting NKG2DL comprising NKG2D protein or its variants. Chimeric antigen receptor (CAR) and its modified immune response cells, as well as their preparation methods and applications.

BACKGROUND

With the rapid development of biotechnology, immune cell therapy has become the fourth major therapy in the field of cancer therapy.

Cancer immunotherapy mainly comprises adoptive cell therapy, immunomodulator, tumor vaccine and immunoassay, immunology checkpoint block therapy and so on. Among them, in the field of cell therapy, chimeric antigen receptor modified immune cells (especially Chimeric Antigen Receptor T-Cell (CAR-T) therapy has undoubtedly become a superstar for research institution and pharmaceutical industry. The company is competing for the star.

CAR-T (Chimeric Antigen Receptor T-Cell, chimeric antigen receptor modified T cells) was used as a substitute. The principle of immune therapy is to modify T cells from patients themselves by means of genetic engineering. The antigen receptor is modified to generate CAR-T cells, which can specifically recognize tumor surface associated antigens. The engineering T cells can specifically recognize tumor surface antigen (tumor cell marker), thus targeting to the tumor. Relative to conventional immune cells, CAR-T cells that it has higher targeting, killing activity and persistence, and can overcome the local immunosuppressive microenvironment of tumor. And the state of host immune tolerance is broken. The modified immune cell therapy represented by CAR-T cells is urgent. The treatment of leukemia and non Hodgkin's lymphoma has a significant progresses and is regarded as the most promising therapy approach. One of the methods of tumor treatment.

However, 90% of cancers are solid tumor, more solid tumors and more tumor specific targets. Tumor specific antigens need to be further confirmed. The remarkable bottleneck of CAR-T immunotherapy for solid tumors is CAR-T cells require very high specificity of antigen expression on tumor cells, otherwise, T cells can be easily held. Continuous activation can kill normal cells or release a large number of cytokines, causing serious reaction effects. Although CAR-T exempts the specificity of pestilence therapy for tumor cell antigen expression is very high, but tumor specific target antigens are rare. Most of the antigens expressed by tumor do not have tumor only specificity, and tumor related resistance is not. CAR-T immunotherapy as a target has problems such as "miss the target". Study the broad-spectrum, efficient and safe CAR-T immunotherapy is an urgent need.

The key to the application of chimeric antigen receptor modified immune response cells is to identify at least one tumor associated antigens, which are highly expressed on the surface of tumor cells but not expressed or very low on the surface of normal cells.

In recent years, studies have shown that the expression of NKG2DL protein is an indicator of the cell's "stress state". They are rarely expressed or expressed only in a short time in healthy tissues, but are usually found in different sources. Cell surface has a high level of expression, such as myeloma cells and more than 80% of primary ovarian cancer cells. The expression of NKG2DL was found, especially the low dose of chemotherapeutic drugs and radiotherapy, DNA damage of tumor cells, activation of DNA repair pathway, and increase of NKG2DL on the surface of tumor cells. The receptor of NKG2DL protein is NKG2D. Research shows that NKG2D-NKG2DL system is on the machine, where the body plays an important role in anti-tumor immunity. NKG2D identifies NKG2DL on the surface of tumor cells. NKG2DL transmits activation signals and activates the immune system, thereby killing tumor cells. NKG2DLs expression are a specific change of tumor cells when the tumor occurs. This treatment provides a more precise target and inspiration for the development of new therapies and drugs.

KNOWLEDGE COMMON TO THE INVENTION

Technical Problems

In view of the above problems and/or other problems related to the technology, the aim of the invention is to overcome the existing tumors. The specificity of T cells binding and killing tumor cells is not strong in clinical environment. The problem of low efficiency is to provide chimeric antigen receptors targeting human NKG2DL, and their genes and recombinant expression vectors. Engineered and engineered NKG2DL targeted chimeric antigen receptor modified immune response cells and their applications. The engineered NKG2DL targeted immune response cells can enhance the killing effect of tumor cells. This provides a promising way for cancer therapy.

A Solution to the Problem

SUMMARY

In the first aspect, this application provides a human NKG2D protein ligand or its functional variants target to human NKG2DL, wherein functional variants comprise sequences selected from the following groups:

(1) SEQ ID NO:4, SEQ ID NO:5, SEQ ID NO:6, SEQ ID NO:7, SEQ ID NO:8, or the amino acid sequence shown in SEQ ID No.9, or (2) (1) functional variants generated by modifications at one or more amino acids, wherein the amino acid sequences of the variants have 70~99% identity with the amino acid sequences shown by the SEQ ID NO:4, or SEQ ID NO:5, or SEQ ID NO:6, or SEQ ID NO:7, or SEQ ID NO:8, or SEQ ID NO:9.

In second aspect, this application provides a specific chimeric antigen receptor targeting to human NKG2DL, wherein it comprises a guided sequence, an extracellular domain targeting human NKG2DL, a transmembrane domain, and a intracellular signaling domain connected are sequentially connected from the amino terminal to the carboxyl terminal, wherein the immune response cells modified by the NKG2D protein target human NKG2DL have the killing efficiency up to 40%~70% when effector to target ratio is equal to 10:1, and the extracellular recognition domain of the targeted human NKG2DL comprises human NKG2D protein targeted to human NKG2DL or its functional variants according to claim 1, and preferably the human NKG2D protein targeting to the human NKG2DL is the NKG2DL receptor.

In some embodiments, the specific chimeric antigen receptor also comprises a hinges region.

In some embodiments, the transmembrane domain comprises transmembrane regions.

[In some embodiments, the intracellular signaling domain comprises the receptor tyrosine activating motif and costimulatory signaling domain. In some embodiments, the amino acid modifications include, but are not limited to, substitutions, deletions, and additions of amino acids including, but not limited to, derived polypeptides produced by substitutions, deletions, and additions of amino acids.

In some embodiments, transmembrane domain comprises CD8 transmembrane, CD28 transmembrane, and CD3 zeta transmembrane, CD4 transmembrane, 4-1BB transmembrane, OX40 transmembrane, ICOS transmembrane, CTLA-4 transmembrane, PD-1 transmembrane, LAG-3 transmembrane, 2B4 transmembrane, BTLA transmembrane, and any kind of synthetic peptides (not based on proteins associated with immune responses).

In some embodiments, the immune receptor tyrosine activating motif comprises the intracellular signaling domain of the CD3 zeta or the FcεRIγ intracellular signaling domain.

In some embodiments, the costimulatory signaling domain comprises one of kind CD28 intracellular signaling domain, CD137/4-1.BB intracellular signaling domain, CD134/OX40 intracellular signaling domain and ICOS intracellular signaling domain. In one embodiment, the hinge region or hinge region of the immunoglobulin is modified.

In one embodiment, the leader sequence is selected from (1) an amino acid sequence shown in SEQ ID NO:3, or (2) the amino acid modified functional variants of (1), wherein the amino acid modified functional variants have 70~99% preferably 80~99%, more preferable 90~99%, and most preferably 95~99% respectively identities to the amino acid sequences set forth in SEQ ID NO:3.

In some embodiments, the amino acid sequence of human CD8 polypeptide in the hinge region is selected from SEQ ID NO:10 or (2) amino acid modified functional variants of (1), wherein the amino acid modified functional variants have 70~99% preferably 80~99%, more preferable 90~99%, and most preferably 95~99% respectively identity to the amino acid sequence shown in SEQ ID NO:10.

In some embodiments, the amino acid sequence of human CD8 in the transmembrane domain is selected from SEQ ID NO:11, or (2) amino acid modified functional variants of (1), wherein the amino acid modified functional variants have 70~99%, preferably 80~99%, more preferably 90~99% respectively, and the most preferably 95~99% identity to the amino acid sequence shown in SEQ ID NO: 11.

In some embodiments, the human 4-1BB intracellular domain is selected from (1) a polypeptide with an amino acid sequence shown by SEQ ID NO: 12, or (2) amino acid modified functional variants of (1), wherein the amino acid modified functional variants have 70~99% identity to the amino acid sequence shown by SEQ ID NO:12, preferably 80~99%, more preferably 90~99%, and the most preferably 95~99% respectively identity to the amino acid sequence shown by SEQ ID NO: 12.

In some embodiments, the human CD28 zeta intracellular domain is selected from: (1) a polypeptide with an amino acid sequence shown by SEQ ID NO:13, or (2) amino acid modified functional variants of (1), wherein the amino acid modified functional variants have 70~99% preferably 80~99%, more preferably 90~99%, and the most preferably 95~99% respectively identity to the amino acid sequence shown in SEQ ID NO:13.

In some embodiments, the CD3 zeta intracellular domain is selected from: (1) an amino acid shown in SEQ ID NO:14, or (2) amino acid modified functional variants of (1), wherein the amino acid modified functional variants have 70~99% preferably 80~99%, more preferably 90~99%, and the most preferably 95~99% respectively identity to the amino acid sequence shown in SEQ ID NO: 14.

In some embodiments, the CD3 zeta intracellular domain is selected from: (1) an amino acid shown in SEQ ID NO:15, or (2) amino acid modified functional variants of (1), wherein the amino acid modified functional variants have 70~99% preferably 80~99%, more preferably 90~99%, and the most preferably 95~99% respectively identity to the amino acid sequence shown in SEQ ID NO:15 respectively.

In some embodiments, the chimeric antigen receptor targets human NKG2DL which is expressed by recombination or vector.

In some embodiments, the amino acid sequence from the amino terminal to the carboxyl terminal of the chimeric antigen receptor comprises a guiding sequence, a human NKG2D sequence according to claim 1, a human CD8 hinge region sequence, a human CD8 transmembrane region sequence, a human CD28 intracellular domain sequence, a human 4-1BB intracellular domain sequence, and a CD3 zeta intracellular domain sequence which are sequentially connected.

In some embodiments, the amino acid sequence from the amino terminal to the carboxyl terminal of the chimeric antigen receptor comprises a guided sequence, and a human NKG2D sequence according to claim 1, a CD8 hinge region sequence, a CD8 transmembrane region sequence, and CD28 intracellular domain sequence, and a CD3 zeta intracellular domain sequence which are sequentially connected, or In some embodiments, the amino acid sequence from the amino terminal to the carboxyl terminal of the chimeric antigen receptor comprises a guided sequence, a human NKG2D sequence according to claim 1, a CD8 transmembrane region, a 4-1BB intracellular domain sequence, and a CD3 zeta intracellular domain sequence which are sequentially connected, In some embodiments, the amino acid sequence from the amino terminal to the carboxyl terminal of the chimeric antigen receptor comprises a guided sequence a the human NKG2D sequence according to claim 1, a CD8 transmembrane region sequence, a CD28 intracellular domain sequence, and a CD3 zeta intracellular domain sequence which are sequentially connected.

In a preferred embodiment, the guide sequence is shown by SEQ ID NO:3.

In some preferred embodiments, the human NKG2D sequence is shown by any one of SEQ ID NO:4, SEQ ID NO:5, SEQ ID NO:6, SEQ ID NO:7, SEQ ID NO:8 or SEQ ID NO:9.

In a preferred embodiment, the amino acid sequence of human CD8 hinge region is shown by SEQ ID NO: 10.
In a preferred embodiment the amino acid sequence of human CD8 transmembrane region is shown by SEQ ID NO: 11,
In a preferred embodiment, the amino acid sequence of human 4-1BB intracellular domain is shown by SEQ ID NO: 12,
In a preferred embodiment, the amino acid sequence of CD28 intracellular domain d is shown by SEQ ID NO:13,
In a preferred embodiment, the amino acid sequence of CD3 zeta intracellular domain is shown by SEQ ID NO:14 or SEQ ID NO:15.

In the third aspect, this application provides a plurality of nucleic acid molecules of encoding the specific chimeric antigen receptors targeting to human NKG2DL in the second aspect, wherein the nucleic acid molecules comprise a nucleotide sequence of the guiding sequence, a nucleotide sequence of human NKG2D protein targeting to human NKG2DL, and the a guiding sequence of transmembrane domain, and a nucleotide sequence of intracellular signaling domain, wherein the transmembrane domain comprises a transmembrane region, the intracellular signaling domain comprises an immune receptor tyrosine activation sequence and a costimulatory signaling domain connected sequentially from 5' to 3', and optionally, the nucleic acid molecule also comprises the nucleotide sequence encoding hinges region.

In some embodiments, the intracellular signaling domain comprises the receptor tyrosine activating motif and costimulatory signaling domain.

In some embodiments, the targeted to human NKG2DL specifically chimeric antigen receptors, wherein the nucleic acid molecule comprises the coding sequence of hinge area.

In Some Embodiments

[In some embodiments, the transmembrane domain comprises transmembrane regions.

In some embodiments, the nucleic acid molecules comprise a nucleotide sequence encoding a guiding sequence, a nucleotide sequence encoding human NKG2D targeting to human NKG2DL according to claim 1, a nucleotide sequence encoding human CD8 hinge region, a nucleotide sequence encoding human CD8 transmembrane region, a nucleotide sequence encoding CD28 intracellular domain, a nucleotide sequence encoding human 4-1BB intracellular domain, and a nucleotide sequence encoding CD3 zeta intracellular domain sequentially connected from 5' to 3'.

In some embodiments, the nucleic acid molecules comprise a nucleotide sequence encoding a guiding sequence, a nucleotide sequence encoding human NKG2D targeting to human NKG2DL according to claim 1, a nucleotide sequence encoding human CD8 transmembrane region, a nucleotide sequence encoding human 4-1BB intracellular domain, and a nucleotide sequence encoding CD3 zeta intracellular domain sequentially connected from 5' to 3'.

In some embodiments, the nucleic acid molecules comprise a nucleotide sequence encoding a guiding sequence, a sequence encoding human NKG2D targeting to human NKG2DL according to claim 1, a nucleotide sequence encoding human CD8 hinge region, a nucleotide sequence encoding human CD8 transmembrane region, a nucleotide sequence encoding human 4-1BB intracellular domain, and a nucleotide sequence encoding CD3 zeta intracellular domain sequentially connected from 5' to 3'.

In some embodiments, the nucleic acid molecules comprise a nucleotide sequence of encoding a guiding sequence, a nucleotide sequence encoding human NKG2D targeting to human NKG2DL according to claim 1, a nucleotide sequence encoding human CD8 hinge region, a nucleotide sequence encoding human CD8 transmembrane region, a nucleotide sequence encoding CD28 intracellular domain, and a nucleotide sequence encoding CD3 zeta intracellular domain sequentially connected from 5' to 3'.

In the fourth aspect, this application provides a recombinant vector or expression plasmid comprising the nucleic acid of the third aspect of this application.

In the fifth aspects, this application provides a promoter for constructing the recombinant vector in the fourth aspect, and expressing the specific chimeric antigen receptor of target binding human NKG2DL described in the second aspect of this aspect. The promoters include but are not limited to, nucleotide sequences, such as EF1 Alpha promoter showed as SEQ ID NO:29 and the EFS promoter showed as SEQ ID NO:30.

In a preferred embodiment, the promoter is a nucleotide sequence, such as the EFS promoter shown in SEQ ID NO:30.

In a preferred embodiment, the nucleotide sequences is showed as EF1 alpha promoter of SEQ ID NO:29.

[In the sixth aspect, the application provides the recombinant virus which can express the chimeric antigen receptors specifically targeting to NKG2DL in the second aspect of this application are able to infect immune response cells.

In the seventh aspect, this application provides a separate modified immune response cell, which comprises a chimeric antigen receptor targeting to human NKG2DL in the second aspect of this application and the recombinant vector or expression vector from transformation of is described in the fourth aspect of the invention.

In some embodiments, the immune response cells may comprise cytotoxic T lymphocytes, NK cells, and NKT cells or helper T cells.

In some embodiments, the immune response cells also comprise at least one exogenous costimulatory ligand.

In the eighth aspect, this application provides a preparation method for the separated chimeric antigen receptor modified immune response cells in the seventh aspect of the application, wherein the method comprises the following steps:

First, connected the nucleic acid molecules according to claim 7 to the initial expression vector by molecular cloning, and obtained the expression vector for expressing the specific chimeric antigen receptor targeting to the NKG2DL, Then, transfected the expression vector of specific chimeric antigen receptor targeting to NKG2DL into 293T cells to obtain virus solution, and generated the immune response cells expressing specific chimeric antigen receptor targeting to NKG2DL were produced from the infected cells after infected the immune response cells using the virus solution.

In some embodiments, the immune response cells are selected from T cells, natural killer (NK) cells, Toxic T lymphocytes (CTL), regulatory T cells, human embryonic stem cells and pluripotent stem cell which could be differentiated to lymphoid cells, T cells or natural killer (NK) cells are preferred.

In the ninth aspect, the application provides a pharmaceutical composition used for the treatment or prevention of a tumor diseases, discomfort, or health disorder, which comprises an effective dose of the functional human NKG2D protein ligand or its functional variants targeted to human NKG2DL described in the first aspect of the application, and the chimeric antigen receptor targeting human NKG2DL thereof described in the second aspect, the nucleic acid described in the third aspect of the inventor the isolated and modified immune response cells in the seventh aspect and pharmaceutically acceptable level of excipients, wherein the diseases, discomfort, or health disorder are related to the specific interaction between human NKG2DL target and its ligand NKG2D protein, wherein the disease, discomfort or health disorder of comprise pathogen infection, autoimmune disease, inflammatory disease, allograft, graft rejection and senescence.

In the tenth aspect, the application provides a kit used for the treatment or prevention of a tumor diseases, discomfort, or health disorder, which comprises an effective dose of the functional human NKG2D protein ligand or its functional variants targeted to human NKG2DL described in the first aspect of the application, and the chimeric antigen receptor targeting human NKG2DL thereof described in the second aspect, the nucleic acid described in the third aspect of the invention or the isolated and the modified immune response cells in the seventh aspect and pharmaceutically acceptable level of excipients, wherein the diseases, discomfort, or health disorder are related to the specific interaction between human NKG2DL target and its ligand NKG2D protein, wherein the disease, discomfort or health disorder of comprise pathogen infection, autoimmune disease, inflammatory disease, allograft, graft rejection and senescence.

wherein, the treatments and preventions involve the infusion of the effective quantity chimeric antigen receptor T cells (CAR-T cells) targeting NKG2DL into patients with diseases that are caused by specific interactions with NKG2DL and NKG2D ligand proteins in the seventh aspect of the application.

The discomforts or disorders of health are related to the specific interaction between NKG2DL and NKG2D ligand proteins.

In some embodiments, diseases, discomfort or health disorders comprise tumor formation, infection, autoimmunity, allograft, graft rejection, and aging.

The invention is based on human NKG2D molecule to construct specific chimeric antigen receptor targeting human NKG2DL or the CAR modified T cell (CAR-T cell), the innovative CAR-T cell can effectively target to attack many kinds of tumor cells which can be developed preparations for the treatment of tumors, especially the expression of NKG2DL positive tumor cells.

THE BENEFICIAL EFFECTS OF THE INVENTION

Beneficial Effect

Inventor of the invention accidentally discovered in the research that the invention comprises the specific construction of human NKG2D chimeric antigen receptor targeting human NKG2DL modified T cells, the preparation method is simple. At the effector to target ratio is 10:1, the killing rate of tumor cells from 40% to 70%, and also can significantly prolong persistence of the immune cells in patients. The improvement of immune cells specifically target tumor cells, especially those NKG2DL positive. The improvement of immune cells or their composition cytotoxicity for tumor or tumor formation from liver cancer, gliblastoma, ovarian cancer, gastric cancer, medulloblastoma, pancreatic cancer, lung cancer, prostate cancer, breast cancer, neuroblastoma, bladder cancer, colon cancer, renal cell carcinoma, leukemia, lymphoma, multiple myeloma, melanoma.

Activity. The modified immune response cells that express human chimeric NKG2D receptor targeting NKG2DL positive tumors are described in the invention which is new approach option for tumor immunotherapy, and has potential industrial application prospects.

BRIEF DESCRIPTION OF THE DRAWINGS

FIGS are a connection sequential schematics of the construction of the chimeric antigen receptors in embodiments 1 and 2.

FIGS. 4A, 4B and 4C depict the result of CAR-T cell activity detected by flow cytometry in embodiment 5, wherein FIG. 4A is a blank control which means T cell without infection with virus, FIG. 4B is specific CAR-T targeting CD19 KD-019 control, FIG. 4C is a specific CAR-T cell targeting to NKG2DL KD-025

FIGS. 5A, 5B and 5C depict the result of expression of KD-025 CAR molecules detected by flow cytometry in embodiment 5, wherein FIG. 5A is a blank control which means T cell without infection with virus, FIG. 5B is specific CAR-T targeting CD19 KD-019 control, FIG. 5C is a specific CAR-T cell targeting to NKG2DL KD-025.

FIG. 6A is control: a comparison (R&D Systems, IC003A), FIG. 6B is hepatoma cell SMMC7721, FIG. 6C is glioblastoma cell U251, FIG. 6D is ovarian cancer cell SKOV3, FIG. 6E is gastric cancer cell NUGC4, FIG. 6F is medulloblastoma HTB186, FIG. 6G is pancreatic cancer cell BXPC3, FIG. 6H is lung cancer cell A549, FIG. 6I is prostate cancer cell PC3, FIG. 6J is breast cancer cell MCF7.

FIGS. 20A and 20B depict the safety tolerance dose and toxicology test results by using B-NSG animals with KD-025 CAR, wherein FIG. 20A shows toxicological test results, and FIG. 20B shows the test results of a safe tolerance dose experiment.

DETAILED DESCRIPTION OF THE EMBODIMENTS

Figure 1:
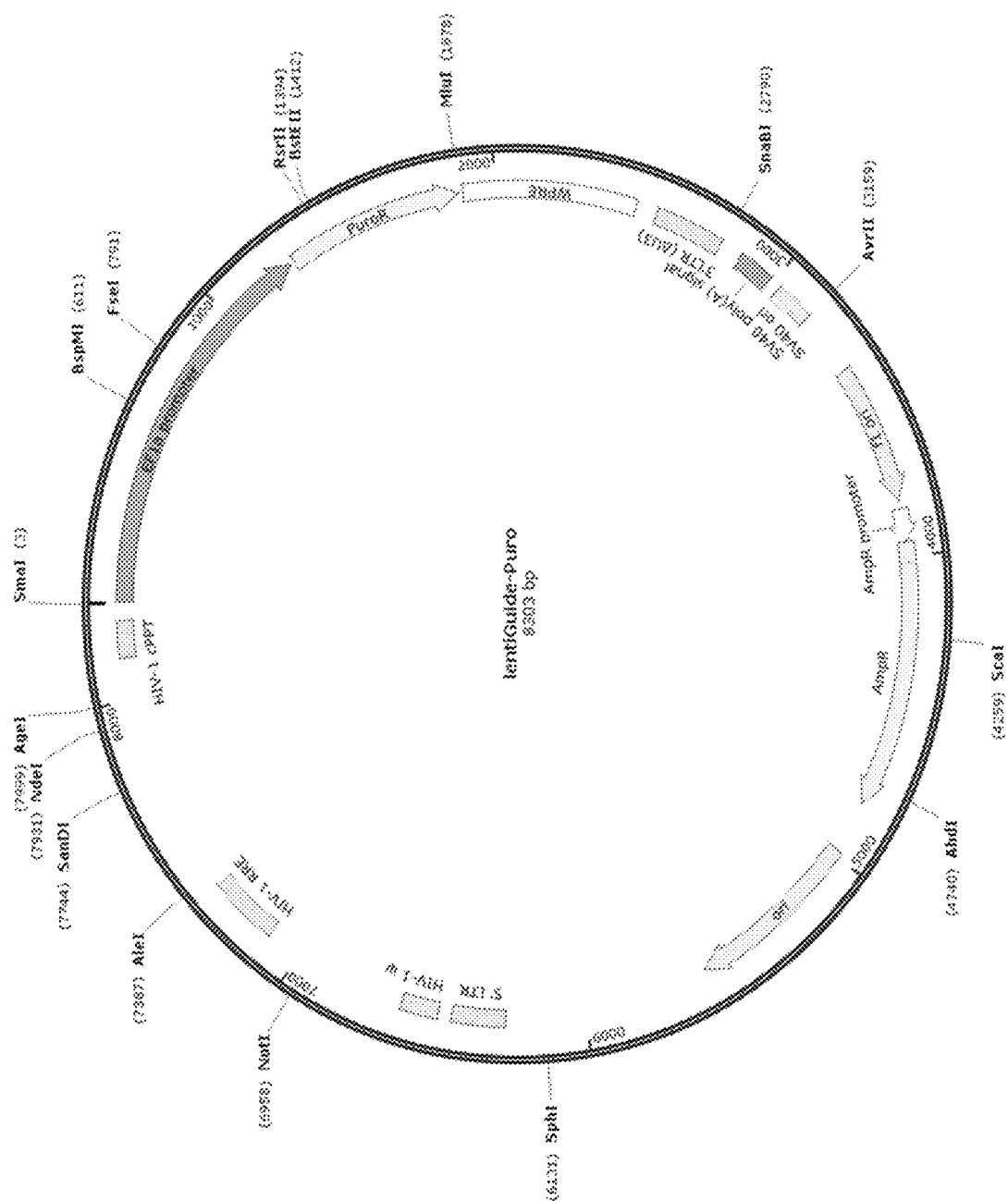
FIG. 1 is a schematics of lentivirus vector used in the present invention as an example.

Unless otherwise defined, all technical and scientific terms used in this article are technical personnel in the field of the invention. The meaning that is usually understood.

Term "functional variant" is the term "functional variety" that is modified by the maternal structure. With the same or similar biological functions and properties, such as those having the same target binding function with the maternal body. Variant. As a particular example, functional variants can be carried out in one or more places in the matrix. The replacement is obtained. The functional variant in this application is the amino acid sequence of the ligand NKG2D in NKG2DL. Based on the modified structure produced by combining NKG2DL targets.

Term "amino acid modification" refers to CAR which does not significantly affect or alter the disclosure of the amino acid sequence, i.e., the extracellular recognition domain is characterized by a conservative amino acid modification. This conservative modification comprises the amino acid substitution, addition and deletion.

Term "homology" refers to the amino group of the target amino sequence or the target nucleotide sequence matches with the reference sequence with a high proportions homology of acid or nucleotides. The homology in this application can be produced using standard software such as BLAST or FAST.

Term of chimeric antigen receptor (CAR).

The chimeric antigen receptor comprises the guiding peptide, extracellular target recognition domain, transmembrane domain and intracellular domain.

Specific chimeric antigen receptor (CAR) is a specific antibody or ligand designed artificially to bind target antigens, i.e., a specific chimeric antigen receptor (CAR) targeting human NKG2DL in this application. CAR could integrate specifically coding sequences into T cells through lentiviral vectors, i.e., transferring the coding sequence of monoclonal antibodies into T cells.

Term "antigen" refers to the highly specific expression of a target molecule in the surface of tumor cells, which can be identified and targeted specifically with ligand. In this invention, it refers to the human NKG2DL. The extracellular antigen binding domain is NKG2D in specific exemplary embodiments. Any NKG2D molecule sequence is possible to exist in heterogeneous sequences of fusion protein to form extracellular antigen binding domain in specific particular embodiments.

The receptor of NKG2DL protein is NKG2D and NKG2D-NKG2DL system plays an important role in antitumor immunity of the body. NKG2D targets NKG2DL produced on the surface of tumor cells and transduce the activation function of immune system, and thereby killing the tumor cells.

Term "recognition" refers to the selective combination of targets. The term "specific combination" or "specific combining" "or" specific targeting" is used in this article which means that peptides or their fragments recognize and bind to the target biomolecules, such as peptides, but it basically does not recognize the binding of other molecules in the sample, i.e., naturally including other molecules of biological sample of the polypeptide of the invention.

Term "specific binding" refers to the combination of two molecules, such as ligand and receptor, which are very characteristic. When there are many other molecules, one molecule (ligand) and another specific molecule (receptor). The ability to combine, that is, to show the preferential combination ability of one molecule to another molecule in the heterogeneous mixture of molecules. The specific binding of ligand to receptor is also verified as follows: when there is an excess of unlabeled ligands, the binding of the labelled ligand to the receptor decreased (i.e., the competition test).

The term "receptor" is a molecular structure that can be specifically combined with target sequences. In particular, the receptor is combined with another the ligand on the cell surface allows cell to cell recognition and/or interaction. The receptor is the NKG2D targeting human NKG2DL in the present invention.

Term "costimulatory molecule" refers to a molecule on the cell surface except antigen receptors or their ligands which affects lymphocytes recognizing antigens.

Costimulatory ligand is a protein expressed on the cell surface, which produces a co stimulation response when it combines with its receptor, that is, the intracellular response to the stimulation of the antigen when the antigen is combined with its CAR molecule.

Term "vector" refers to any genetic element, such as plasmid, phage, transposon, clay, chromosome, viruses, virus particles, etc., which can be duplicated under appropriate control elements, and transfers gene sequence to the target cell. Therefore, the term comprises cloning and expression vectors, as well as viral vectors and plasmid.

Term "expression vector" refers to a recombinant nucleic acid sequence, that is, recombinant DNA molecule, which comprises the coding sequence and nucleic acids sequence necessary for expressing the coding sequences in specific host organisms. The nucleic acid sequences necessary for expression in prokaryotes typically comprise promoters, operon (optional) and ribosomal binding sites are usually accompanied by other sequences whereas eukaryotic cells utilize promoters, enhancers, terminator and polyadenosine acidification signal.

The term "immune response cell" used in this article is the cell or its progenitor or its progeny cells that play important role in the immune response.

The term "isolation cells" refers to the immune cells that are isolated from the molecules and/or cell components of natural cells mixture.

The term "pathogen" used in this article refers to Viruses, bacteria, fungi, parasites, or protozoans that can cause diseases.

The term "(treating, treatment)" refers to clinical intervention that attempts to change the process of disease of an individual or cell that is being treated, and can be used for prevention or during the process of clinical pathology. The therapeutic effects of treatment comprise, but not limited to, the occurrence or recurrence of the disease, the remission of the symptoms, the reduction of any direct or indirect pathological consequences of the disease, the prevention of metastasis, the speed of reducing the progression of the disease, the reduction or mitigation of the state of the disease, and the prognosis of remission or improvement. By preventing the progress of disease or disease, treatment can prevent the deterioration caused by the patients who have been attacked or diagnosed or suspected to suffer from the disease, and the treatment can prevent the disease or symptoms of the subjects who have the risk of the disease or those who are suspected to have the disease.

The term "killing efficiency" refers to a certain ratio of tumor cell dead after tumor antagonists and tumor cells are mixed in the in vitro testing system. In this article, the ratio of tumor cell death caused by chimeric antigen receptor modified immune response cells. In particular, the killing ratio of the tumor cells expressing NKG2DL is described when NKG2D chimeric antigen receptor modified T cells with an effector to target ratio of 10:1.

The term "disease" used in this article is any disease or disorder that destroys or interferes with the normal functions of cells, tissues, or organs such as diseases comprise tumor formation or cell pathogen infection.

The term "effective dose" used in this article refers to the amount enough to have therapeutic effect. In one embodiment, effective dose is the amount enough to prevent, improve, or suppress the growth, continuous proliferation, or metastasis of a tumor formation, ie., invasion or migration.

The term "exogenous nucleic acid molecules or peptides" used in this article, refers to nucleic acid molecules or peptides that are not normally found in or obtained by cells. (ie., cDNA, DNA or RNA molecules). The nucleic acid may be derived from another organism, or it can be an mRNA molecule that is not normally exist in cells or samples.

In the first aspect, this application provides a human NKG2D protein targeting to human NKG2DL and its functional variants, which include the following:

(1) SEQ ID NO:4, SEQ ID NO:5, SEQ ID NO:6, SEQ ID NO:7, SEQ ID NO:8, or SEQ ID NO:9 the amino acid sequence shown as (1), or (2) the amino acid modified variants of (1), wherein the amino acid sequences of the variants have 70~99% identity to the amino acid sequences shown by the SEQ ID NO:4, or SEQ ID NO:5, or SEQ ID NO:6, or SEQ ID NO:7, or SEQ ID NO:8, or SEQ ID NO:9.

According to the existing researches, the peptide NKG2D protein targeting human NKG2DL is based on the amino acid sequence of human NKG2D protein.

According to the existing researches, herein CAR constructed based on the full length amino acid sequence of NKG2D only have poor function, because the functional domains such as the NKG2D intracellular region is derived from natural killer cells and is not compatible with the T cells.

Then, the inventor screened and analyzed NKG2D amino acid sequence targeting NKG2DL based on the full length amino acid sequence of NKG2D by using protein prediction tool for sequence analysis and the functional domain optimization, and further designed and constructed the amino acid sequence of chimeric antigen receptor, which comprises the specific part sequence of NKG2D targeting to human NKG2DL, wherein it is also a technical challenge for the skilled person in this field to design and develop the amino acid sequences of the hinge area, transmembrane region, and intracellular signaling activation region most suitable with and matched with T cells.

Through the creative work and continuous amino acid sequence design and sequence assembly and screening, the inventor conducted random screening test and specific function verification, such as constructing viral vectors and further infection of T cells to obtain modified T cells, and detecting the cytotoxic activity of modified T cell in vitro, the sequences of more than 10 different CAR molecules are screened by, the sequences were then adjusted according to the comparison and blast of the results of multiple random composition, and finally the best sequence was screened out. The NKG2D amino acid sequence and its functional variants at the high titer targeting to human NKG2DL of the invention were obtained.

In some particular embodiments, the amino acid modifications include, but are not limited to substitutions, deletions, and additions of amino acids, the functional variants include, but are not limited to the derived peptides or peptide analogues of the human NKG2D amino acid sequences of the target human NKG2DL produced by the substitutions, deletions, and additions of amino acids, and the derived peptides and peptide analogues are homologous to the amino acid sequences of human NKG2D.

In some particular embodiments, the amino acid modifications include, but are not limited to, chemical modifications of the amino acid side chain, natural or un natural amino acid substitutions, mutations, deletions, insertions, or the post-translational modifications.

In some particular embodiments, the variants of amino acid produced by modifications at one or more points in the amino acid sequences of the NKG2D amino acid sequence of the target human NKG2DL are the polypeptides homologous to the amino acid sequence shown by SEQ ID NO:5. In some particular embodiments, the variant of amino acid modified by one or more amino acid sequences of the NKG2D amino acid sequence of the target human NKG2DL is a polypeptide that is homologous to the amino acid sequence shown by SEQ ID NO:6. In some particular embodiments, the variants of amino acid produced by modifications at one or more points in the amino acid sequences of the NKG2D amino acid sequence of the target human NKG2DL are the polypeptides homologous to the amino acid sequence shown by SEQ ID NO:7. In some particular embodiments, the variants of amino acid produced by modifications at one or more points in the amino acid sequences of the NKG2D amino acid sequence of the target human NKG2DL are the polypeptides homologous to the amino acid sequence shown by SEQ ID NO:8. In some particular embodiments, the variants of amino acid produced by modifications at one or more amino acid sequences of the NKG2D amino acid sequence of the target human NKG2DL are the polypeptides homologous to the amino acid sequence shown by SEQ ID NO:9.

The homologous polypeptides in the first aspect determined compared with the reference polypeptide, herein these peptides refer to the polypeptides with 70~99% preferably 80~99%, more preferable 90~99%, and most preferably 95~99% identity to the NKG2D targeting to the human NKG2DL.

In some particular embodiments, the polypeptides with 70~99% preferably 80~99%, more preferable 90~99%, and most preferably 95~99% identity to the amino acid sequences set forth by SEQ ID NO:4, SEQ ID NO:5, SEQ ID NO:6 as described. SEQ ID NO:7, SEQ ID NO:8 or SEQ ID NO:9 are the polypeptides derived by substitution, deletion or addition of 1~10 amino acids, preferably 1~5 amino acids, more preferably 1~3 amino acids from any one amino acid sequence among SEQ ID NO:4, SEQ ID NO:5, SEQ ID NO:6, SEQ ID NO:7, SEQ ID NO:8 or SEQ ID NO:9.

In addition to full-length polypeptides, the subject of the first aspect of the application also provides any fragment of a peptide or peptide domain in the topics for the purpose of this application. In some embodiments, the fragments may be at least 5~15 amino acids. In some embodiments, the fragments may be at least 20 continuous amino acids, at least 30 continuous or at least 50 continuous amino acids. In some embodiments, the fragments may be at least 60 to 80, 100, 200, 300, or more continuous amino acids.

The amino acid fragments of the first aspect of the application may be produced by a method known by the skilled person in the field, or the non protein analogue may be produced by a processing strategy (e.g., removing the amino acids that is not needed for the biological activity from the new polypeptides or removing the amino acids by the alternative mRNA splicing or the alternative protein processing events).

In the second aspect, this application provides a specific chimeric antigen receptor targeting human NKG2DL characterized in that, the chimeric antigen receptor comprises a guided sequence from the amino terminal to the carboxyl terminal, an extracellular domain targeting human NKG2DL, a transmembrane domain, and a intracellular signaling domain, wherein the immune response cells modified by the NKG2D protein target human NKG2DL have the killing efficiency up to 40%~70% when effector to target ratio is equal to 10:1, and the extracellular recognition domain of the targeted human NKG2DL comprises human NKG2D protein or its functional variant targeted to human NKG2DL according to claim 1, and preferably the human NKG2D protein targeting to the human NKG2DL is the NKG2DL receptor.

In some embodiments, the target chimeric antigen receptor binding to human NKG2DL comprises hinge regions. In some particular embodiments, a CAR further comprise a spacer region, which connects the antigen binding domain to the transmembrane domain. The spacers region may be sufficiently flexible to orients the antigen binding domains in different directions to facilitate antigen recognition. The spacer region may originate from the hinge region of IgG1, or the CH2CH3 region of immunoglobulin and the portion of CD3.

In some particular embodiments, CAR can comprise the spacer, which connects the antigen binding domain to the transmembrane domain. A spacer region can be flexible enough to allow antigen binding domains to orientate in different directions to facilitate antigen recognition. The spacer area can be from the hinge area of IgG1, or the CH2CH3 area of immunoglobulin and the part of CD3.

In some embodiments, the specific chimeric antigen receptor that targets to human NKG2DL comprises a hinge region. In some embodiments, the intracellular signal domain comprises an immunoreceptor tyrosine activation motif, a costimulatory signal domain, an intracellular signal domain comprises an immunoreceptor activation motif and optionally one or more costimulatory signaling domains. The intracellular signaling domain comprises the immune receptor activation motif and optionally comprises one or more costimulatory signaling domains.

In some particular embodiments, the intracellular domain of CAR also comprises at least one costimulatory signaling transduction region, which comprises at least one costimulatory molecule that can provide optimal lymphocyte activation. The "costimulatory molecule" used in this article refers to the effect of lymphocytes on antigen, except for a cell surface molecule from antigen receptor or ligand. At least one costimulatory signaling transduction region comprise CD28 polypeptide, 4-1BB polypeptide and OX40 polypeptide, ICOS polypeptide, 2B4 polypeptide, BTLA polypeptide, synthetic peptide (not based on proteins associated with immune responses), or their composition. Costimulatory molecule can be combined with costimulatory ligands, and costimulatory ligands are proteins expressed on the cell surface, which produce a costimulatory response when they combine with their receptors, that is, the intracellular response to the stimulation of the antigen when the antigen is combined with its CAR molecule. Costimulatory ligands comprise, but are not limited to, CD80, CD86, CD70, OX40L, 4-1BBL, CD48, TNFRSF14 and PD-L1. As an embodiment, the 4-1BB ligand (4-1BBL) can combine 4-1BB (also known as "CD137") to provide intracellular signals, which combine with CAR signals to induce the function of CAR+T cells.

In some embodiments, the costimulatory signaling transduction region of intracellular domain of CAR comprises two kinds of costimulatory molecules: CD28 and 4-1BB (see Sadelain et al., Cancer Discovery, OF1-11, (2013)), or CD28 and OX40.

In some particular embodiments, the intracellular domain of CAR can comprise CD3 zeta polypeptides that activate or stimulate cells, such as lymphoid lineages, such as T cells. The CD3 zeta comprises three Immune receptor tyrosine-based activation motif, and the activation signal is transmitted to the cell after binding antigen (for example, the lymphoid lineage cells, such as T cells).

In some particular embodiments the extracellular recognition domain (also referred to as the extracellular domain or simply referred by the recognition element contained therein) comprises a recognition elements that specifically binds to molecules and antigens present on the surface of the cell of the target cell. The function of the extracellular recognition domain is to anchor the binding cell membrane. The extracellular recognition domain may also comprise a leader sequence or signal peptide that introduces a nascent protein into the endoplasmic reticulum. A signal peptide or leader sequence may be necessary if the CAR will be glycosylated and anchored in the cell membrane. The signal sequence or leader sequence may be a peptide sequence (about 5, about 10, about 15, about 20, about 25 or about 30 amino acids in length) present at the N-terminus of the newly synthesized protein, which directs the protein into the secretory pathway.

The domain of extracellular recognition antigen can also comprise the guide sequence or signal peptide that guides new proteins into the endoplasmic reticulum.

In some particular examples, the leader sequence is covalently linked to the 5-terminal of the extracellular antigen binding domain.

In some particular embodiments, the transmembrane domain comprises a transmembrane domain.

In some particular embodiments, the intracellular signaling domains comprise immune receptor tyrosine activating motif and costimulatory signaling domain.

In some particular embodiments, the transmembrane domains of CAR comprise at least part of hydrophobic alpha helices. Different transmembrane domains produce different receptor stability. After antigen recognition, receptor clusters and signals are transduced to cells.

In some particular embodiments, the transmembrane domains of CAR also comprises any kind of the CD8 transmembrane, the CD28 transmembrane, the CD3 zeta transmembrane, the CD4 transmembrane, the 4-1BB transmembrane, the OX40 transmembrane, the ICOS transmembrane, the CTLA-4 transmembrane, the PD-1 transmembrane, the LAG-3 trans membrane, the 2B4 transmembrane and the transmembrane region, any kind of synthetic peptides (not based on proteins associated with immune responses).

In some particular embodiments, the immune receptor tyrosine activating motif comprises intracellular signaling domain of the CD3 zeta or the FcεRIγ intracellular signaling domain.

In some particular embodiments, the costimulatory signaling domain comprises at least one of the CD28 intracellular signaling domains, the CD137/4-1BB intracellular signaling domain, the CD134/OX40 intracellular signaling domain, and the ICOS intracellular signaling domain.

In some particular embodiments, the hinge is selected from the hinges of the CD8 alpha hinge, the IgG hinge, or the variants of the hinges or hinges of the whole or part of the immunoglobulin through modifications at one or more amino acids In some particular embodiments, the intracellular domain of a CAR comprise a human CD3ζ polypeptide that can activate or stimulate cells (eg, cells of the lymphoid lineage, such as T cells). CD3ζ contains 3 ITAMs and transmits an activation signal to cells (eg, cells of the lymphoid lineage, such as T cells) upon binding to the antigen.

In some particular embodiments, the intracellular domain of CAR can comprise CD3 zeta polypeptides that activate or stimulate cells, such as lymphoid lineages, such as T cells. The CD3 zeta comprises three Immune receptor tyrosine-based activation motif, and the activation signal is transmitted to the cell after binding antigen (for example, the lymphoid lineage cells, such as T cells).

In certain particular embodiments, the intracellular domain of the CAR further comprises at least one costimulatory signaling region which comprises at least one costimulatory molecule that provides optimal lymphocyte activation. The "costimulatory molecule" used in this article refers to the effect of lymphocytes on antigen, except for a cell surface molecule from antigen receptor or ligand. As used herein, "costimulatory molecule" refers to a cell surface molecule other than an antigen receptor or its ligand required for an effective response of a lymphocyte to an antigen. At least one costimulatory signaling region comprise a CD28 polypeptide, a 4-1BB polypeptide, an OX40 polypeptide, an ICOS polypeptide, a 2B4 polypeptide, a BTLA polypeptide, a synthetic peptide (not based on a protein associated with an immune response), or a combination thereof. A costimulatory molecule can bind to a costimulatory ligand, which is a protein expressed on the cell surface that, when bound to its receptor, produces a costimulatory response, ie, a cell that provides stimulation when the antigen binds to its CAR molecule. Should be inside costimulatory ligands include, but are not limited to, CD80, CD86, CD70, OX40L, 4-1BBL, CD48, TNFRSF14, and PD-L1.

In an exemplary embodiment, the costimulatory molecule is a 4-1BB ligand, (ie, 4-1BBL), which can bind to 4-1BB (also known as "CD137") to provide an intracellular signal that is combined with the CAR signal to induce CAR Effector cell function of +T cells.

In some embodiments, the costimulatory signaling transduction region of intracellular domain of CAR comprises two kinds of costimulatory molecules: CD28 and 4-1BB (see Sadelain et al., Cancer discovery, OF1-11, (2013)), or CD28 and OX40.

In some non-limiting embodiments, the hinge region are selected from the group consisting of a CD8 alpha hinge region, an IgG hinge region, or the entire or portion of the variants of the immunoglobulin comprising one or more amino acid modifications in the hinge region or hinge region.

In one embodiment, the amino acid sequence of the chimeric antigen receptor from the amino terminus to the carboxy terminus comprises the leader sequence, the amino acid sequence of human NKG2D targeting human NKG2DL described in the first aspect of the present application, and the human CD8 hinge region, the amino acid sequence, the amino acid sequence of the human CD8 transmembrane region, the amino acid sequence of the human CD28 intracellular domain, the amino acid sequence of the human 4-1BB intracellular domain, and the amino acid sequence of the human CD3 cell intracellular domain sequentially connected in series;

In one preferred embodiment, the amino acid sequence of the chimeric antigen receptor from the amino terminus to the carboxy terminus is sequentially connected in series by the leader sequence, the amino acid sequence of human NKG2D targeted to bind human NKG2DL described in the first aspect of the present application, and the human CD8 transmembrane, the amino acid sequence of the region, the amino acid sequence of the human CD8 hinge region sequence, the amino acid sequence of the intracellular domain of human CD28, and the amino acid sequence of the CD3 cell intracellular domain.

In one preferred embodiment, the amino acid sequence of the chimeric antigen receptor from the amino terminus to the carboxy terminus by a leader sequence, a human NKG2D amino acid sequence targeted to bind human NKG2DL described in the first aspect of the present application, a human CD8 transmembrane region, the amino acid sequence, the amino acid sequence of the 4-1BB intracellular domain, and the amino acid sequence of the CD3 cell intracellular domain are sequentially connected in series.

In one preferred embodiment, the amino acid sequence of the chimeric antigen receptor from the amino terminus to the carboxyl end comprises the leader sequence, the amino acid sequence of NKG2D target human NKG2DL described in the first aspect of the present application, amino acid sequence of human CD8 transmembrane region, amino acid sequence of human CD28 intracellular domain and amino acid sequence of human CD3 zeta intracellular domain are sequentially connected in this application.

In one preferred embodiment, the amino acid sequence of the chimeric antigen receptor from the amino terminus to the carboxyl end comprises the leader sequence, the amino acid sequence of NKG2D target human NKG2DL described in the first aspect of the present application, amino acid sequence of human CD8 hinge region, amino acid sequence of human CD8 transmembrane region, amino acid sequence of human CD28 intracellular domain and amino acid sequence of human CD3 zeta intracellular domain are sequentially connected in this application.

In a preferred embodiment, the amino acid sequence of the chimeric antigen receptor from the amino terminus to the carboxyl end comprises the leader sequence, the amino acid sequence of NKG2D target human NKG2DL described in the first aspect of the present application, amino acid sequence of human CD8 transmembrane region, amino acid sequence of human 4-1BB intracellular domain and amino acid sequence of human CD3 zeta intracellular domain are sequentially connected in this application.

In a preferred embodiment, the amino acid sequence of the chimeric antigen receptor from the amino terminus to the carboxyl end comprises the leader sequence, the amino acid sequence of NKG2D target human NKG2DL described in the first aspect of the present application, amino acid sequence of human CD8 transmembrane region, amino acid sequence of human CD28 intracellular domain and amino acid sequence of human CD3 zeta intracellular domain are sequentially connected in this application.

In one preferred embodiment, the amino acid sequence of the chimeric antigen receptor from the amino terminus to the carboxyl end comprises the leader sequence, the amino acid sequence of NKG2D target human NKG2DL described in the first aspect of the present application, amino acid sequence of human CD8 hinge region, amino acid sequence of human CD8 transmembrane region, amino acid sequence of human 4-1BB intracellular domain and amino acid sequence of human CD3 zeta intracellular domain are sequentially connected in this application.

In one preferred embodiment, the amino acid sequence of the chimeric antigen receptor from the amino terminus to the carboxyl end comprises the leader sequence, the amino acid sequence of NKG2D target human NKG2DL described in the first aspect of the present application, amino acid sequence of human CD8 hinge region amino acid sequence of human CD8 transmembrane region, amino acid sequence of human CD28 intracellular domain and amino acid sequence of human CD3 zeta intracellular domain are sequentially connected in this application.

In some particular embodiments, the guiding sequence is selected from (1) a polypeptide with an amino acid sequence shown by SEQ ID NO:3, or (2) a functional variants of (1) produced by amino acid modifications, wherein the amino acid modified functional variant have 70~99% preferably 80~99%, more preferable 90~99%, and most preferably 95~99% identity to the amino acid sequence shown by SEQ ID NO:3, In some particular embodiments, the CAR of the subject disclosed in the second aspect of this application comprises the spacer region, also known as the hinge region, which connects the antigen binding domain to the transmembrane domain. A spacer region can be flexible enough to allow antigen binding domains to orientate in different directions to facilitate antigen recognition. The spacer region may originate from the hinge area of IgG1, or the CH2CH3 area of immunoglobulin and the part of CD3. Some spacer regions comprise the immunoglobulin CH3 domain or the CH3 domain and the CH2 domain, while some spacer region comprise the whole or part of the immunoglobulin (for example, IgG1, IgG2, IgG3, IgG4) hinges, that is, the sequence locates between the CH1 and the CH2 domains of the immunoglobulin, such as the IgG4Fc hinges or CD8 hinges. The sequence of immunoglobulin sources can comprise one or more amino acid modifications, for example, 1, 2, 3, 4 or 5 substitutions. In some particular embodiments, the spacer area is hinge region.

In some particular embodiments, the subject covered by CAR in the second aspect of the transmembrane domain comprising CD28 polypeptide and the costimulatory signaling transduction region comprising CD28 polypeptide.

In some embodiments, hinge region comprises human CD8 polypeptide that is selected from (1) a polypeptide with an amino acid sequence shown by SEQ ID NO: 10, or (2) functional variants of amino acid produced by amino acid modifications, wherein the amino acid modified functional variants have 70~99% preferably 80~99%, more preferable 90~99%, and most preferably 95~99% identity to the amino acid sequence shown by SEQ ID NO:10, or optionally comprise at most one or at most two or at most three conserved amino acid substitutions. In particular embodiments, the human CD8 hinge region amino acid sequence has a continuous amino acid sequence showed as SEQ ID NO:10 with the length of at least 20, or at least 30, or at least 40, or at least 50, less and up to 164 amino acids.

In some embodiments, the transmembrane region comprises human CD8 peptides that is selected from (1) a polypeptide with an amino acid sequence shown by SEQ ID NO:11, or (2) amino acid modified functional variants of (1), wherein the amino acid modified functional variants have 70~99% preferably 80~99%, more preferable 90~99%, and most preferably 95~99% identity to the amino acid sequence shown by SEQ ID NO:11, or can be optionally comprised at most one or at most two or at most three conserved amino acids substitution. In particular embodiments, the human CD8 transmembrane region amino acid sequence has a continuous amino acid sequence showed as SEQ ID NO:11 with the length of at least 20, or at least 30, or at least 40, or at least 50, less and up to 164 amino acids.

In some embodiments, the amino acid sequence of the human 4-1BB intracellular domain is selected from (1) a polypeptide with an amino acid sequence shown by SEQ ID NO: 12, or (2) amino acid modified functional variants have 70~99% preferably 80~99%, more preferable 90~99%, and most preferably 95~99%, wherein the amino acid modified functional variants have 70~99% preferably 80~99%, more preferable 90~99%, and most preferably 95~99% identity to the amino acid sequence shown by SEQ ID NO: 12, or optionally comprised at most one or more two or more than three conserved amino acids substitution. In particular embodiments, the human 4-1BB intracellular domain amino acid sequence has a continuous amino acid sequence showed as SEQ ID NO: 12 with the length of at least 20, or at least 30, or at least 40, or at least 50, less and up to 164 amino acids.

In some particular embodiments, the intracellular domain of CAR can comprise CD3 zeta polypeptides that activate or stimulate cells, such as lymphoid lineages, such as T cells. The CD3 zeta comprises three Immune receptor tyrosine-based activation motif, and the activation signal is transmitted to the cell after binding antigen (for example, the lymphoid lineage cells, such as T cells).

In some embodiments, the amino acid sequence of the CD3 zeta intracellular domain is selected from (1) a polypeptide with an amino acid sequence shown by SEQ ID NO: 14, or (2) the amino acid modified functional variants, wherein the amino acid modified functional variants have 70~99% preferably 80~99%, more preferable 90~99%, and most preferably 95~99% identity to the amino acid sequence shown by SEQ ID NO: 14, or optionally comprise at most one or more two or more than three conserved amino acids substitution. In particular embodiments, the CD3 zeta intracellular domain amino acid sequence has a continuous amino acid sequence showed as SEQ ID NO: 14, with the length of at least 20, or at least 30, or at least 40, or at least 50, less and up to 164 amino acids.

In some particular embodiments, the amino acid sequence of the CD3 zeta intracellular domain is selected from is selected from (1) a polypeptide with a sequence of amino acids shown by SEQ ID NO:15, or (2) amino acid modified functional variants of amino acid modified, wherein the amino acid modified functional variants have 70~99% preferably 80~99%, more preferable 90~99%, and most preferably 95~99% identity to the amino acid sequence shown by SEQ ID NO:15, or optionally comprise at most one or more two or more than three conserved amino acids substitution. In particular embodiments, the CD3 zeta intracellular domain amino acid sequence has a continuous amino acid sequence of SEQ ID showed as NO:15, with the length of at least 20, or at least 30, or at least 40, or at least 50, less and up to 164

In some embodiments, the amino acid sequence of the human CD28 intracellular domain is selected from (1) a polypeptide with an amino acid sequence shown by SEQ ID NO:13, or (2) (1) amino acid modified functional variants, wherein the amino acid modified functional variants have 70~99% preferably 80~99%, more preferable 90~99%, and most preferably 95~99% identity to the amino acid sequence shown by SEQ ID NO:13, or optionally comprised at most one or more two or more than three conserved amino acids substitution. In particular embodiments, the human CD28 intracellular domain amino acid sequence has a continuous amino acid sequence showed, by SEQ ID NO: 13 with the length of at least 20, or at least 30, or at least 40, or at least 50, less and up to 255 amino acids.

In an exemplary embodiment, the guiding sequence is shown as SEQ ID No.3.

In an exemplary embodiment, amino acid sequence of human NKG2D is described as SEQ ID NO:4. In an exemplary embodiment, amino acid sequence of human NKG2D is described as SEQ ID NO:5. In an exemplary embodiment, amino acid sequence of human NKG2D is described as SEQ ID NO:6. In an exemplary embodiment, amino acid sequence of human NKG2D is described as SEQ ID NO:7. In an exemplary embodiment, amino acid sequence of human NKG2D is described as SEQ ID NO:8. In an exemplary embodiment, amino acid sequence of human NKG2D is described as SEQ ID NO:9.

In an exemplary embodiment, amino acid sequence of human CD8 hinge region is described as SEQ ID NO:10.

In an exemplary embodiment, amino acid sequence of CD8 transmembrane region is described as SEQ ID NO: 11.

In an exemplary embodiment, amino acid sequence of the intracellular domain of human 4-1BB is described as SEQ ID NO:12.

In an exemplary embodiment, amino acid sequence of CD28 domain is described as SEQ ID NO: 13.

In an exemplary embodiment, amino acid sequence of the CD3 zeta domain is described as SEQ ID NO: 14.

In an exemplary embodiment, amino acid sequence of the CD3 zeta domain is described as SEQ ID NO:15.

In one particular embodiments, specific chimeric antigen receptor (CAR) targeting to human NKG2DL is expressed in recombinant system or by vector.

In some particular embodiments, the intracellular domain of the CAR of the target binding human NKG2DL also comprises at least one costimulatory signaling conduction region, which comprises at least one of the costimulatory ligand molecules that activates lymphocyte. It is combined with CAR signal to induce the effector cell function of CAR-T cells wherein, the costimulatory ligands comprise but are not limited to CD80, CD86, CD70, OX40L, 4-1BBL, CD48, TNFRSF14 and PD-L1.

In one particular embodiments, intracellular domain of CAR targeting human NKG2DL in this application comprises 4-1BB polypeptide. 4-1BB can act as a ligand to tumor necrosis factor (TNF) and has stimulatory activity. 4-1BBL is covalently connect to the 5' terminal of the extracellular antigen binding domain or, to the 3' terminal of the intracellular domain.

In particular embodiments of this application, 4-1BB polypeptide is selected from (1) a polypeptide with a sequence of amino acids shown by SEQ ID NO: 12, or (2)amino acid modified functional variants of, wherein the amino acid modified functional variants have 70~99% preferably 80~99%, more preferable 90~99%, and most preferably 95~99% identity to the amino acid sequence shown by SEQ ID NO: 12, or optionally comprise substitutions of at most one or more two or more than three conserved amino acids.

In particular embodiments, 4-1BB polypeptide has a continuous amino acid sequence of SEQ ID NO: 12 showed, and its length is at least 20, or at least 30, or at least 40, or at least 50, less and up to 255 amino acids.

In the third aspect, the application comprises a nucleic acid molecule of encoding the specific chimeric antigen receptor targeting to human NKG2DL described in second aspect, wherein the nucleic acid molecules comprise a nucleotide sequence encoding guiding sequence sequentially connected from 5' to 3' a nucleotide sequence encoding human NKG2D targeting to human NKG2DL, a nucleotide sequences encoding the transmembrane domain, and a nucleotide sequence encoding intracellular signaling domain, wherein the polynucleotide encoding an extracellular recognition domain that binds to human NKG2DL can be modified by codon optimization. Codon optimization can alter naturally occurring and recombinant gene sequences to achieve the highest possible level of productivity in any given expression system. Factors involved in different stages of protein expression include codon adaptability, mRNA structure, and various cis-elements in transcription and translation.

In some embodiments, the nucleic acid molecules also comprises a nucleotide sequences encoding the hinge region.

In some embodiments, the intracellular signaling domain comprises a receptor tyrosine activating motif] and the costimulatory signaling domain;

In some exemplary embodiments, the nucleic acid molecules respectively comprise nucleotide sequence encoding a guiding sequence, and the human NKG2D sequence in the first aspect of this application, and human CD8 hinge region sequence, and human CD8 transmembrane region sequence, and human CD28 intracellular domain sequence, and human 4-1BB intracellular domain sequence and human CD3 zeta intracellular domain sequence from 5' to 3' sequentially.

In some exemplary embodiments, the nucleic acid molecules respectively comprise nucleotide sequence for encoding a guiding sequence, and the human NKG2D sequence in the first aspect of the application, and the human CD8 transmembrane region sequence, and the human 4-1BB intracellular domain sequence and the human CD3 zeta intracellular domain sequence from 5' to 3' sequentially.

In some exemplary embodiments, the nucleic acid molecules respectively comprise nucleotide sequence encoding a guiding sequence, and the human NKG2D sequence in the first aspect of this application, and human CD8 hinge region sequence, and human CD8 transmembrane region sequence, and human 4-1BB intracellular domain sequence and human CD3 zeta intracellular domain sequence from 5' to 3' sequentially.

In some embodiments, the transmembrane domain comprises a CD8 transmembrane domain, a CD28 transmembrane domain, a CD3ζ transmembrane domain, a CD4 transmembrane domain, a 4-1BB transmembrane domain, an OX40 transmembrane domain, ICOS transmembrane domain, CTLA-4 transmembrane domain, PD-1 transmembrane domain, LAG-3 transmembrane domain, 2B4 transmembrane domain, BTLA transmembrane domain, synthetic peptide (not based on immune response) Any of the related proteins), In some embodiments, the immunoreceptor tyrosine activation motif comprises an intracellular signal domain of a CD3 ζ chain or an FcεRIγ intracellular signal structure.

In some embodiments, the costimulatory signal domain comprises at least one of a CD28 intracellular signaling domain, a CD137/4-1BB intracellular signaling domain, a CD134/OX40 intracellular signaling domain, and an ICOS intracellular signaling domain.

In some embodiments, the hinge region is selected from the group consisting of a CD8 alpha hinge region, an IgG hinge region, or a hinge region or hinge region comprising all or part of an immunoglobulin that has been modified by one or more amino acids.

In some embodiments, the nucleotide sequence encoding human NKG2D targeting the extracellular recognition domain of human NKG2DL is shown as SEQ ID NO:17 or has identity of 80%, 85%, 90%, 95% or 99% with the sequence shown by SEQ ID NO: 17.

In an exemplary embodiment, the nucleotide sequence encoding human NKG2D targeting the extracellular recognition domain of human NKG2DL is shown as SEQ ID NO:18 or has the identity of 80%, 85%, 90%, 95% or 99% with the sequence shown by SEQ ID NO:18.

In an exemplary embodiments, the nucleotide sequence encoding human NKG2D targeting the extracellular recognition domain of human NKG2DL is shown as SEQ ID NO:19 or has the identity of 80%, 85%, 90%, 95% or 99% with the sequence shown by SEQ ID NO:19.

In one embodiments, the nucleotide sequence encoding human NKG2D targeting the extracellular recognition domain of human NKG2DL is shown as SEQ ID NO:20 or has the identity of 80%, 85%, 90%, 95% or 99% with the sequence by SEQ ID NO:20.

In one embodiments, the nucleotide sequence encoding human NKG2D targeting the extracellular recognition domain of human NKG2DL is shown as SEQ ID NO:21 or has the identity sequence with shown by SEQ ID NO:21.

In one embodiments, the nucleotide sequence encoding human NKG2D targeting the extracellular recognition domain of human NKG2DL is shown as SEQ ID NO:22 or has the identity of 80%, 85%, 90%, 95% or 99% with the sequence shown by SEQ ID NO:22.

In some embodiments, the nucleotide sequence encoding human CD8 hinge region is shown as SEQ ID NO:23 or has the identity of 80%, 85%, 90%, 95% or 99% with the sequence shown by SEQ ID NO:23.

In some embodiments, the nucleotide sequence encoding human CD8 transmembrane region is shown as SEQ ID NO:24 or has the identity of 80%, 85%, 90%, 95% or 99% with the sequence shown by SEQ ID NO:24.

In some embodiments, the nucleotide sequence encoding human 4-1BB intracellular domain is shown as SEQ ID NO:25 or has the identity of 80%, 85%, 90%, 95% or 99% with the sequence shown by SEQ ID NO:25.

In some embodiments, the nucleotide sequence encoding CD28 intracellular domain is shown as SEQ ID NO:26 or has the identity s of 80%, 85%, 90%, 95% or 99% with the sequence shown by SEQ ID NO:26.

In some embodiments, the nucleotide sequence encoding CD3 zeta intracellular domain is shown as SEQ ID NO:27 or has the identity of 80%, 85%, 90%, 95% or 99% with the sequence shown by SEQ ID NO:27.

In some embodiments, the nucleotide sequence encoding CD3 zeta intracellular domain is shown as SEQ ID NO:28 or has the identity of 80%, 85%, 90%, 95% or 99% with the sequence shown by SEQ ID NO:28.

In the fourth aspect, this application provides the recombinant vector or expression plasmid comprising the chimeric antigen receptor in the second aspect or the nucleic acid in the third aspect of the application.

The gene modification to immune response cells (for example, T cells, CTL cells, NK cells) can be achieved by using recombinant DNA or RNA to construct cell transducers of basically homologous cell compositions. In one embodiment, the vector is retroviral vector (eg., gamma retrovirus or lentivirus), which can transduce DNA or RNA constructs into the host cell genome. For example, the polynucleotides encoding NKG2D specific CAR targeting human NKG2DL can be cloned into a retroviral vector and can be expressed from its endogenous promoter, the long terminal repeat sequence of the retrovirus, or from an alternative internal promoter.

The non-viral vector or RNA or usomh Random chromosome integration or targeted integration (such as nuclease, transcriptional activation of TALEN, ZFN, and/or regular cluster interval short palindrome repetition (CRISPR) or transgenic expression (for example, using natural or chemically modified RNA) may be another alternative to construct the recombinant vector or expression plasmid.

In some embodiments, the vectors may be selected from the gamma retrovirus vector, lentiviral vector, adenovirus vector, or adenosine related virus vector. In an example embodiment, the vector is a gamma retroviral vector.

In the fifth aspect, The present application provides a promoter for constructing a recombinant vector in the fourth aspect of the application and expressing a specific chimeric antigen receptor of the target binding human NKG2DL in the second aspect of the application, the promoters comprise, but are not limited to, nucleotide sequences, such as EF1 alpha promoter shown in SEQ ID NO:29 and EFS promoters as shown in SEQ ID NO:30.

In an exemplary preferred embodiment, the promoter is used to construct the recombinant vector in the fourth aspect and to express the specific chimeric antigen receptor of the target binding human NKG2DL in the second aspect is the EF1 alpha promoter as shown by the SEQ ID NO:29.

In an exemplary preferred embodiment, the promoter is used to construct the recombinant vector in the fourth aspect and to express the specific chimeric antigen receptor of the target binding human NKG2DL in the second aspect is the EFS promoter as shown by the SEQ ID NO:30.

In the sixth aspects, the present application provides a recombinant virus, which can express chimeric antigen receptor targeting to NKG2DL and infect the immune response cells in the second aspect of the invention.

In some embodiments, the immune response cells are cytotoxic T lymphocytes, NK cells, and NKT cell or auxiliary T cells, etc.

In an exemplary embodiment, the immune response cells are cytotoxic T lymphocytes.

In some embodiments, the virus is lentivirus, adenovirus, adenosine related virus or retrovirus.

In an exemplary embodiment, the virus is lentivirus.

In an exemplary embodiment, the virus is adenovirus.

In the seventh aspect, the present application provides an isolated modified immune response cell comprising the chimeric antigen receptor in the second application, which is derived in the transformants from the recombinant vector or an expression plasmid in the third aspect of the application.

In respect to the initial gene modification of the cell to provide targeted human NKG2DL specific immune response cells, retroviral vectors are usually used in transduction, however any other appropriate viral vector or non viral delivery system may be used. In respect to the subsequent gene modification to provide cells comprising at least two kinds of antigen presenting complexes with costimulatory ligands, retroviral gene transfer (transduction) is also proved to be effective for cells. The combination of retroviral vectors and suitable assembly lines is also suitable, in which capsid proteins are functional for human infected cells.

In some embodiments, the immune response cell comprises at least one exogenous costimulatory ligand.

Optional transduction methods also comprise direct co-culture of cells and production cells.

In some embodiments, a possible transduction method further comprises direct co-cultivation of the cells with the producer cells. The viral vectors for transducing can be used to express costimulatory ligands (e.g., 4-1BBL and IL-12) in immune response cells. Preferably, the selected vector exhibits high infection efficiency and stable integration and expression.

In some embodiments, preferably, the at least one of the costimulatory ligand is selected from 4-1BBL, CD80, CD86, CD70, OX40L, CD48, TNFRSF14 and their composition, or more preferably, the costimulatory ligand is 4-1BBL.

In some embodiments, the immune response cell is selected from T cells, natural killer (NK) cells, cytotoxic T lymphocytes (CTL), regulatory T cells, human embryonic stem cells and pluripotent stem cells that differentiate into lymphoid cells, preferably T cells and natural killer (NK) cells, preferable as T cells.

In some embodiments, vectors for CAR expression may be used to transduce multiple T cell subsets isolated from patients.

The seventh aspect of this application disclose isolated and modified immune response cells, which can express the extracellular identification domain able to specifically binding human NKG2DL, and which may be used to treat or prevent tumor formation, immune disease, or for antiaging.

In an exemplary embodiment, wherein the isolated and modified immune response cells are CAR-T cells.

The genetically modified central memory type T cells can be prepared from human NKG2D chimeric antigen receptor targeting human NKG2DL and then kept in cold storage.

In the eighth aspect of the present application provides a method for preparing an isolated and modified chimeric antigen receptor modified immune response cell in the sixth aspect of this application, include the following steps:

First, connected and isolated the nucleic acid molecules in the third aspect into the expression vector through molecular cloning, and obtained the specific expression vector of the specific chimeric antigen receptor of the target NKG2DL;

and then, transfected the specific CAR expression vector targeting NKG2DL into 293T cells to obtain the virus solution;

Finally, used the virus to infect the immune response cells, and produced the isolated and modified immune response cells expressing the specific chimeric antigen receptor targeting NKG2DL after virus infection.

In some particular embodiments, the immune response cells modified in the invention can be cells of lymphoid lineages. The cells of the lymphatic family are selected from B, T and natural killer (NK) cells, which provide the production of antibodies, the regulation of the cellular immune system, the detection of foreign substances in the blood, and the function detection foreign cells of the host. Lymphoid cell lines in particular embodiments comprise T cells, natural killer (NK) cells, cytotoxic T lymphocytes (CTL), regulatory T cells, embryonic stem cells, and pluripotent stem cells (for example, pluripotent stem cells that can be differentiated into lymphoid cells).

In some embodiments, immune response cells are selected from T cells, natural killer (NK) cells, cytotoxic T lymphocytes (CTL), regulatory T cells, human embryonic stem cells, and pluripotent stem cells which can be differentiated into lymphoid cells, prefer T cells or natural killer (NK) cells. In some instance embodiments, T cells are mature lymphocytes in the thymus and mainly response for cell-mediated immunity. T cells participate in the acquired immune system.

In some particular embodiments, T cells comprise but are not limited to helper T cells, cytotoxic T cells, and memory T cells (including central memory T cells, stem like memory T cells (or stem like memory T cells) and two types of effector memory T cells (e.g., TEM and TEMRA cells), regulatory T cells (also known as inhibitory T cells), natural killer cells, sticky membrane related constant T cells, and gamma delta T cells. In some embodiments, T cells expressing CAR express Foxp3 to achieve and maintain T regulatory phenotype.

The modified immune response cells of the application can further comprise at least one exogenous costimulatory ligand, which makes the immune response cells co-expressing exogenously or be induced to co-express exogenously based on NKG2D, specific chimeric receptor targeting human NKG2DL and at least one exogenous costimulatory ligand. The interaction between the specific CAR targeting human NKG2DL and at least one of the costimulatory ligands provides an important non antigen specific signal for the complete activation of immune response cells, such as T cells. In some embodiments, at least one costimulatory ligand is selected from 4-1BBL, CD80, CD86, CD70, OX40L, and composition thereof. In one embodiment, the costimulatory ligand is 4-1BBL. In one embodiment, the costimulatory ligand is 4-1BBL.

In a preferred embodiment, the isolated modified immune response cells are T cells.

In a preferred embodiment, the isolated modified immune response cells are natural killer (NK) cells In some particular embodiments, the isolated and modified immune response cells (such as T cells) may be autologous, non autologous (for example, allogeneic), or derived from engineered progenitor cells or stem cells in vitro.

In the ninth aspect, the application provides a pharmaceutical composition, which comprises an effective amount of the isolated and modified immune response cell in the sixth aspect of the invention and pharmaceutical acceptable excipients.

The disclosed drug composition in the application comprises an isolated and modified immune response cell and a pharmaceutically acceptable vector that express for the specific chimeric antigen receptor targeting human NKG2DL.

The application of the pharmaceutical composition can be autologous or allogeneic. For example, the immune response cells expressing the specific CAR of the target human NKG2DL and the composition can be obtained from one subject and applied to the same subject or different compatible subjects. Local injection, including catheter delivery, whole body injection, local injection, intravenous injection, or gastrointestinal administration, can be used to use T cells or their progeny of the peripheral blood of the invention (for example, in vivo, in vitro, or in vitro derived). The public subject pharmaceutical composition in this invention is applied such as a pharmaceutical composition comprising an immune response cell expressing NKG2D specific CAR, is used, it is usually prepared into a unit dose injectable form as solution, suspension, emulsion.

The composition of the application can be a preparation, immune response cells express the specific chimeric antigen receptor (CAR) of the targeted human NKG2DL and the composition thereof, which can be conveniently provided as a sterile liquid preparation, such as a water solution, a suspension, a emulsion, a dispersive solution or a sticky composition, which can be buffered to the selected Liquid formulations are usually easily prepared than gel, other viscous compositions and solid compositions. In addition, liquid compositions are more convenient to use, especially by injection. On the other hand, the composition of stickiness samples can be prepared in the proper viscosity range to provide longer contact time with specific tissues. Liquid or a viscous composition may comprise a carrier, which may comprise water, saline, phosphate buffer salts. Solvents or fractions of water, polyols (e.g. glycerol, propylene glycol, liquid polyethylene glycol, etc.), suitable mixtures and dispersive medium thereof.

The additives, including antimicrobial, preservatives, antioxidants, chelating agents and buffers, can be added to enhance the stability and aseptic properties of the composition.

All of carriers, diluents or additives used in this application must be compatible with an immune response cell expressing a specific chimeric antigen receptor (CAR) targeting human NKG2DL in the public theme of the invention.

If necessary, the viscosity of the composition can be maintained at a selected level using a pharmaceutically acceptable thickening reagents. The selection of appropriate carriers and other additives will depend on the exact approach of delivery and the nature of specific dosage forms, such as liquid dosage forms (for example, whether the composition is prepared in a solution, a suspension, a gel or another liquid form, such as a time release form or a liquid filling form).

In the tenth aspect, the present application provides a kit for the treatment or prevention of tumor formation, pathogen infection, autoimmune disease, allograft, or graft rejection or anti-aging, wherein comprises the immune response cells in a sixth aspect or the nucleate in a third aspect of the invention of the invention.

If necessary, the immune response cells are provided with the instructions together, which are applied to the subjects with symptom of a risk of tumor formation, or pathogen infection, or immune disease, or allograft or senescence. Instructions usually comprise information about compositions used in the treatment or prevention of tumor formation, pathogen infection, immune diseases or allograft. In other embodiments, the instructions comprise at least one of the following: a description of a therapeutic preparation which comprises a dose regimen and application method for the treatment or prevention of the formation of a tumor, a pathogen infection, an immune disease or a allograft or its symptoms; note which comprises taboo; indications; non indication; information overload; adverse reactions; animal pharmacology; clinical research; and/or reference. The instructions can be directly attached on the container (when it exists), or as a label on the container, or as a separate page, handbook, card, or folding print, in the container or with the container.

In the eleventh aspect, the application provides human NKG2D protein and its variants targeted to human NKG2DL in the first aspect of the invention, and the chimeric antigen receptor target binding to human NKG2DL in the second aspect, and the recombinant vector or expressing plasmid in the fourth aspect, and the recombinant virus in the fifth aspect, and the isolated and modified immune response cells are obtained by preparation method in the seventh aspect, and composition in the eighth aspect, and the application of kits in the treatment or prevention of diseases in the ninth aspect, which the treatment or prevention comprises the application of the effective amount NKG2D targeting NKG2DL CAR-T cells in the second aspect of this application to the patients with diseases caused by specific interactions with NKG2DL and NKG2D proteins.

In some embodiments, the diseases comprises tumor formation, pathogen infection, autoimmune diseases, allograft, graft rejection, and aging.

In some embodiments, the tumor formation, infection of pathogens, autoimmune diseases, inflammatory diseases, allograft, or transplant rejection or senescence are related to the specific interaction of NKG2DL and NKG2D proteins.

In some embodiments, the treatment or prevention of tumor formation involves increasing the growth of immune activated cytokines by reducing the tumor load in the subjects, increasing or prolonging the survival of the subjects with the tumor formation or responding to the cancer cells or pathogens of the subjects.

In some embodiments, tumor or tumor formation is selected from Liver cancer, glioblastoma, gastric cancer, ovarian cancer, medulloblastoma, pancreatic cancer, lung cancer, prostate cancer, breast cancer and neuroblastoma, bladder cancer, colon cancer, renal cell carcinoma, leukemia, lymphoma, multiple myeloma, melanoma, and its composition (and to correspond target cells tested in embodiments).

In an exemplary embodiment, the tumor or tumor formation is liver cancer.

In an exemplary embodiment, the tumor or tumor formation is glioblastoma.

In an exemplary embodiment, the tumor or tumor formation is ovarian cancer.

In an exemplary embodiment, the tumor or tumor formation is gastric cancer.

In an exemplary embodiment, the tumor or tumor formation is medulloblastoma.

In an exemplary embodiment, the tumor or tumor formation is pancreatic cancer.

In an exemplary embodiment, the tumor or tumor formation is lung cancer.

In an exemplary embodiment, the tumor or tumor formation is prostate cancer.

In an exemplary embodiment, the tumor or tumor formation is breast cancer.

The invention is based on human NKG2D molecule to construct specific chimeric antigen receptor (CAR) targeting human NKG2DL and the CAR modified T cell (CAR-T cell). The new CAR-T cell can effectively target a variety of tumor cells and can be used to prepare preparations for the treatment of tumors, especially the NKG2DL positive expression tumor.

In the study, the inventor of the invention has unexpectedly discovered that the preparation method is convenient of the isolated T cells which are modified by human NKG2D chimeric antigen receptor. When the effector to target ratio is 10:1, the killing rate of tumor cells is from 40% to 70%, and also can significantly prolong persistence of the immune cells in patients. The improvement of immune cells specifically target tumor cells, especially those NKG2DL positive. The improvement of immune cells cytotoxicity for lung cancer, the modified immune response cells that express human chimeric NKG2D receptor targeting NKG2DL positive tumors are described in the invention, which is new approach option for tumor immunotherapy, and has potential industrial application prospects.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

The following is further explained by the embodiment, but the invention is not limited to these specific Examples.

The materials and reagents used in the following embodiments can be acquired from commercial companies without special explanation.

Example 1

Preparation of expression plasmid which expresses specific chimeric antigen receptor targeting NKG2DL.

Step 1), determination of amino acid sequence of specific chimeric antigen receptor targeting NKG2DL First, full length amino acid sequences (as shown by SEQ ID NO: 1) and full length nucleotide sequences (as shown by SEQ by ID NO:2) are searched and found from the NCBI Genbank database of the National Medical Library of the United States.

Second, construction of the specific chimeric antigen receptor targeting NKG2DL as follows:

The amino acid sequences of specific CAR molecules targeting NKG2DL from the amino terminal to the carboxyl end, which are sequentially formed with the amino acid sequence of the guided peptide (as shown by SEQ ID NO:3), and the amino acids sequence of the human NKG2D (as shown by SEQ ID NO:4), and the amino acid sequence of the human CD8 hinge region (as shown by SEQ ID NO: 10), and the amino acid sequence of human CD8 transmembrane region (as shown by SEQ ID NO:11), and the amino acid sequence of the intracellular domain of human 4-1BB (as shown by SEQ ID NO:12), and the amino acid sequence of the human CD3 zeta domain (as shown by SEQ ID NO: 14) and sequentially connected.

the nucleotide sequence of specific CAR molecules targeting to NKG2DL from the 5' terminal to the 3' terminal, which is sequentially connected with nucleotide sequence of the encoding guide sequence (as shown by SEQ ID NO: 16), and nucleotide sequence encoding the human NKG2D (as shown by SEQ ID NO: 17), and nucleotide sequence encoding the human CD8 hinge region (as shown by SEQ ID NO:23), and nucleotide sequence encoding the human CD8 transmembrane region (as shown by SEQ ID NO:24), and nucleotide sequence encoding the intracellular domain of human 4-1BB (as shown by SEQ ID NO:25), and nucleotide sequence encoding the human CD3 zeta domain (as shown by SEQ ID NO:27).

Step 2), construction and identification of plasmid expressing the specific CAR molecule targeting NKG2DL.

The nucleotide sequences of the specific CAR molecules targeting to NKG2DL by de novo synthesis are connected to the lentivirus vector lentiGuide-Puro (Idobio, Nanjing as shown by FIG. 1 shown) by molecular cloning, and the full length CAR sequence expression frame of a single coding frame is constructed and expressed by using the EF1 alpha promoter (described in sequence table as shown by SEQ ID NO:29). The specific operation steps are as follows:

De novo synthesize the nucleotide sequence of the specific CAR molecules targeting to NKG2DL comprises the guiding sequence, and human NKG2D sequence, and CD8 hinge region, and CD8 transmembrane region, and 4-1BB intracellular domain, and CD3 zeta domain (Idobio, Nanjing), which was amplified by PCR with primers as follow showed: 5'-cactttggcgccggctcgagggggcccgggtgcaaagatgga-taaagttttaaacagagagga-3' (described in sequence table as shown by SEQ ID NO:31) or 5'-cactttggcgccggctcgaggggggcccgggtaggtcttgaaaggagtgg-gaattggctcc-3' (described in sequence table as shown by SEQ ID NO:32) and 5'-tccagaggttgattgtcgacttaacgcgtt-tagcgaggggggcagggcctgcatgtgaag-3' (described in sequence table as shown by SEQ ID NO:33) and recovered by Axygen gel Recovery Kit (ZeHeng, Hangzhou), and then the homologous recombination ligation was performed with the lentiGuide-Puro vector (Idobio, Nanjing), which was digested by the restriction endonuclease SmaI and MluI. The system and conditions for the particular recombination ligation reaction as follows:

Recombination ligation system:

ligation reaction system comprises the 5 µl recovered PCR products by gel purification, and the 3 µl plasmid which was digested by the restriction endonuclease SmaI and MluI by gel purification, and 5 µl of 4×1402 QuickCloning Kit (Jinuomei, Nanjing) and 7 µl ddH2O with total volume of 20 µl.

Recombination ligation condition: the above reaction system was placed in 50 degree Celsius water bath, which was placed on the ice 1 min after water bath 15 mins.

The recombinant products of 10 µl were transformed into the competent Stbl3, and the specific transformation steps were as follows:

The 5 µl product was added to 50 µl of Stbl3 competent cells (purchased from Invitrogen), and then ice bath 30 min, heat shock at 42° C. 45 s, ice bath 2 min again, and then add 500 µl without LB liquid medium, 37° C. 200 rpm vortex culture 40 min, inoculated cells into ampicillin resistant LB solid plate, cultured overnight in shaking incubator at 37° C. After single colony emerged, pick up 5 moderately sized colonies, extract plasmids and send out for sequencing (Idobio, Nanjing). Sequenced the company sequencing (Idobio, Nanjing), sequenced the results and synthesized the NKG2D specific CAR. Comparing the sequencing results with the sequence of the synthesized NKG2D specific CAR molecule, the sequence was completely correct and proved that the expression plasmids of the specific CAR targeting NKG2DL was obtained (Abbreviation of KD-025 CAR lentivirus vector, EFS promoter).

Step 3), extraction and purification of specific CAR expression plasmid targeting NKG2DL.

In step 2) the Stbl3 strain comprising the plasmid that expresses the specific CAR molecule targeting NKG2DL is cultured in LB medium, and is extracted by using the high purity and without endotoxin Qiagen Plasmid Midi Kit (Qiagen, German) for the infecting purpose. The operation steps are as follows thereof:

1. Harvest overnight bacterial culture 150 ml in a centrifuge tube by centrifuging at 6000×g for 15 mins, as much as possible to remove the supernatant (bacterial cells can be precipitated by multiple centrifugation to collect into one centrifuge tube if the bacterial liquid is overload).

2. Completely suspend the bacterial pellet in 4 ml buffer P1 at the centrifuge tube by a pipette or a vortex oscillator (check if RNase A was added first).

3. Add 4 ml buffer P2, mix thoroughly by softly inverting 4-6 times, and incubate at room temperature for 5 mins.

4. Add 4 ml prechilled buffer P3, mix thoroughly by softly inverting 4-6 times, and incubate at room temperature for 5 mins.

5. Centrifuge at 20000×g for 10 mins at 4° C.

6. Equilibrate a QIAGEN-tip 100 by applying 4 ml buffer QBT, and allow column to empty by gravity flow.

7. Apply the supernatant from step 5 to the QIAGEN-tip and allow it to enter the resin by gravity flow.

8. Wash the QIAGEN-tip with 2×10 ml buffer QC which is allowed to move through the QIAGEN-tip by gravity flow, repeat operation again.

9. Add 5 ml elution buffer QF into the QIAGEN-tip and collect it into a 15 ml new centrifuge tube.

10. Precipitate DNA by adding 3.5 ml room-temperature isopropanol to the eluted DNA and mix thoroughly, and centrifuge at 15000 for 30 mins at 4° C., and carefully decant the supernatant.

11. Wash the DNA pellet with 2 ml room-temperature 70% ethanol and centrifuge at 15000 for 30 mins at 4° C., and carefully decant the supernatant.

12. Air-dry pellet for 5-10 mins and redissolve DNA in a suitable volume of appropriate buffer, and then completely transfer DNA solution into a new 1.5 ml centrifuge tube.

Example 2

Preparation of the plasmid that expresses the specific chimeric antigen receptor targeting NKG2DL in the embodiment 2.

In addition to the human NKG2D sequence in the amino acid sequence of the specific CAR molecule targeting NKG2DL (as shown by SEQ ID NO:5), and the amino acid sequence of the CD3 zeta domain (as shown by SEQ ID NO: 15), encodes the nucleotide sequence of human NKG2D in the nucleotide sequence of the specificity CAR molecules targeting NKG2DL (as shown by SEQ ID NO:18), and step 2) the construction and identification of the specific CAR molecules of the target NKG2DL and the identification of the nucleotide sequences of the specific CAR molecules targeted to NKG2DL by de novo synthesis, and then connected to the lentivirus vector lenti-Guide-Puro (Idobio, Nanjing, FIG. 1) by molecular cloning, and construct a full length CAR sequence of a single encoding frame by the EFS promoter (as shown by sequence table SEQ ID NO:30) in step 1, the rest is the same as the example 1.

Example 3

Preparation of the plasmid that expresses the specific chimeric antigen receptor targeting NKG2DL.

In addition to the human NKG2D sequence in the amino acid sequence of the specific CAR molecule targeting NKG2DL (as shown by SEQ ID NO:6), and encodes the nucleotide sequence of human NKG2D in the nucleotide sequence of the specificity CAR molecules targeting NKG2DL (as shown by SEQ ID NO: 19) in step 1, the rest is the same as the example 1.

Example 4

Preparation of the plasmid that expresses the specific chimeric antigen receptor targeting NKG2DL.

In addition to the human NKG2D sequence in the amino acid sequence of the specific CAR molecule targeting NKG2DL (as shown by SEQ ID NO:7), and encodes the nucleotide sequence of human NKG2D in the nucleotide sequence of the specificity CAR molecules targeting NKG2DL (as shown by SEQ ID NO:20) in step 1, the rest is the same as the example 1.

Example 5

Preparation of the plasmid that expresses the specific chimeric antigen receptor targeting NKG2DL.

In addition to the human NKG2D sequence in the amino acid sequence of the specific CAR molecule targeting NKG2DL (as shown by SEQ ID NO:8), and encodes the nucleotide sequence of human NKG2D in the nucleotide sequence of the specificity CAR molecules targeting NKG2DL (as shown by SEQ ID NO:21) in step 1, the rest is the same as the example 1.

Example 6

Preparation of the plasmid that expresses the specific chimeric antigen receptor targeting NKG2DL.

In addition to the human NKG2D sequence in the amino acid sequence of the specific CAR molecule targeting NKG2DL (as shown by SEQ ID NO:9), and encodes the nucleotide sequence of human NKG2D in the nucleotide sequence of the specificity CAR molecules targeting NKG2DL (as shown by SEQ ID NO:22) in step 1, the rest is the same as the example 1.

Example 7

Isolation and culture of T cells.

Figure 3:
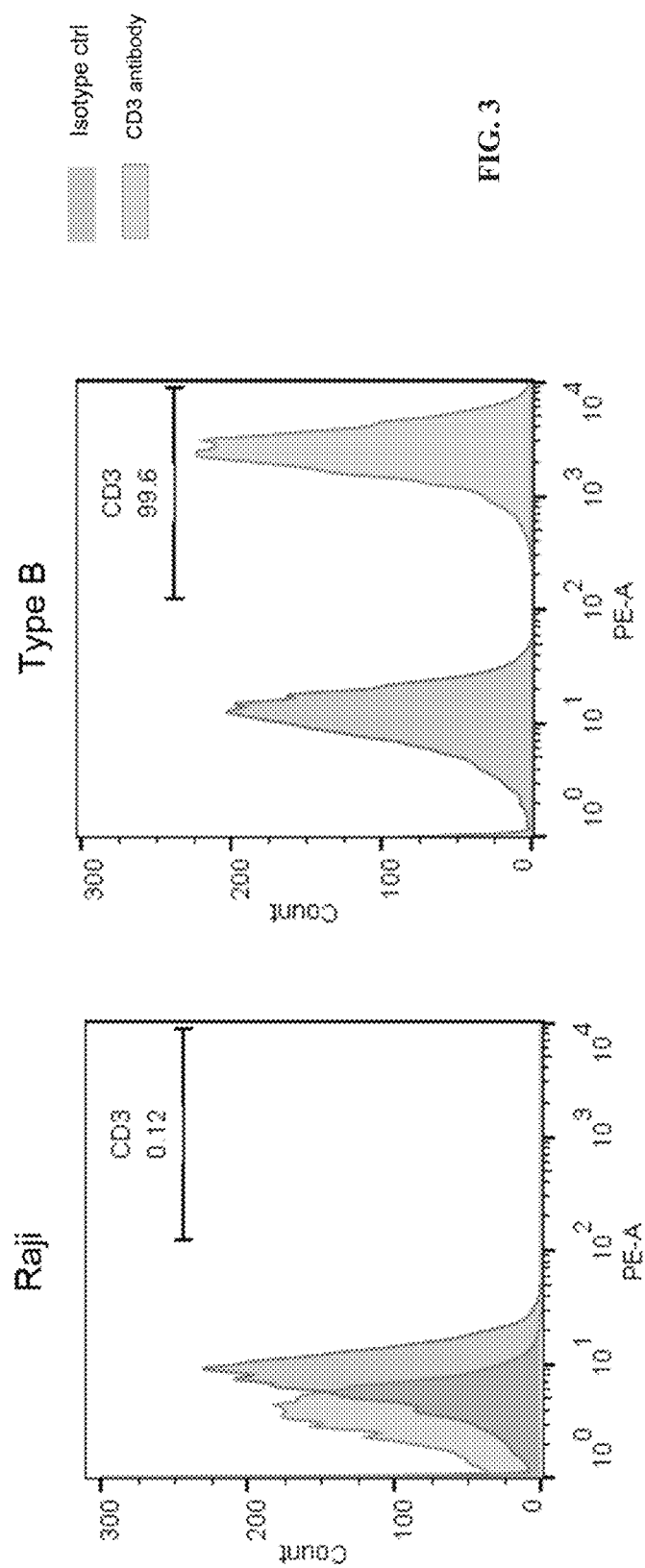
FIG. 3 depicts the result of T cell purity analyzed by flow cytometry in embodiment 2.

Fresh peripheral blood mononuclear cells were isolated from the fresh peripheral blood of healthy donors by density gradient centrifugation, and then used paramagnetic beads coupled with anti-CD3 antibodies and anti-CD28 antibodies (purchased from Invitrogen, USA; Dynabeads Human T-Activator CD3/CD28, catalogue number: 11161D described as the product information) to enrich CD3+T cells. Specifically, peripheral blood mononuclear cells were diluted to the concentration of $(10~30)\times10^6$ cells/ml, then the magnetic beads and cells were mixed thoroughly in the ratio of 3:1 and incubated culture dishes for 2~3 hours at room temperature, and then enriched CD3+T cells by using magnetic particle collector (Magnetic particles Concentrator, referred to as MPC, purchased from Invitrogen, USA, catalogue number: 12301D). Finally, the enriched CD3+T cells were suspended in the culture medium (purchased from Life Technologies, USA, pTmizerT-Cell Expansion SFM, A1048503 described as product information), and adjusted to the solubility at $1\times10^6$ cells/ml, continue to culture at 37° C. and 5% CO2 incubator for 2 days. T cell purity was assayed by using flow cytometry with anti PE anti-human CD3 antibody (purchased from BioLegend, USA, catalogue number: 300408), which the results showed that the purity of T cells after magnetic bead enrichment was more than 97% (FIG. 3).

Example 8

Preparation of virus solution.

Step 3 of embodiment 1) obtained the plasmid that expressed the specific CAR of the target NKG2DL, and the package plasmids psPAX2 and VSVG, which were mixed at the ratio of 10:8:5, and co-transfected into 293T cells (ATCC product, product number: CRL-3216) by using the polyethylene imide transfection reagent (408727, Sigma). The preparation method of package plasmid is referred to Lenti-X Packaging Single Shots instructions (Takara), and the specific transfection procedure is referred to Sigma transfection manual.

After 6 hours transfection, the medium was replaced with a complete medium (purchased from Life Technologies, product number: 11995-065). After 48 hours and 72 hours culture, the virus supernatant was collected respectively and centrifuge at 3000 rpm for 10-15 mins at 4° C. and then was filtered by 0.45 micron membrane. Finally, Super-centrifuge at 25000 rpm for 2~3 hours at 4° C., and then, the virus was condensed. After that the virus was transferred to −80° C. for storage.

Example 9

Preparation of specific CAR-T cells targeting NKG2DL.

The CD3+T cells obtained from embodiment 2 were inoculated into 24 well plates with the concentration of $1\times10^5$ cells/ml, and then cultured for 24 hours at 37° C. and 5% CO2 (culture time based on practice. Typically, the cell confluence rate was between 50-70% when the virus infected).

Figure 2A:
FIG. 2A. EF1 alpha promoter (sequence showed in table as SEQ ID NO:29), FIG. 2B. EFS promoter (sequence showed in table as SEQ ID NO:30), wherein the amino acid sequence of human CD3 zeta domain is described as marker 1, the amino acid sequence of human 4-1BB intracellular domain is described as marker 2, and the amino acid sequence, wherein the amino acid sequence of human CD8 transmembrane region is described as marker 3, and CD8 hinge region amino acid sequence is described as marker 4, human NKG2D amino group, acid sequence is described as marker 5, the guidance amino acid sequence is described is described as marker 6. 7 shows EF1 alpha promoter whereas 8 is EFS promoter.
Figure 2B:

Next day, taking the virus concentrate from embodiment 3, which was added to the cell culture bottle at the value of MOI=1~10. Sealed and centrifuged at low speed (500 g-1000 g/min) for 30~60 minutes, and then placed it to culture at 37° C. incubator. After 48 hours infection, the T cell KD-025 CAR-T cell expressing NKG2D CAR molecule, namely the new CAR-T cell, was obtained, and the molecular structure of CAR was shown in FIG. 2, which can be performed the next functional experiment.

Example 10: Identification

Figure 4C:
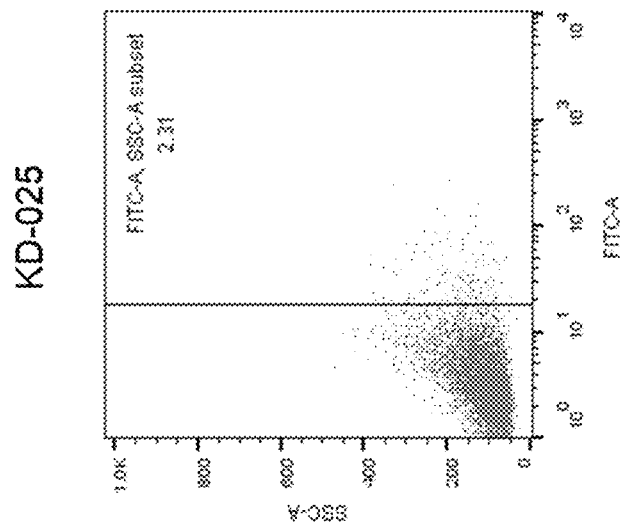
Figure 4B:
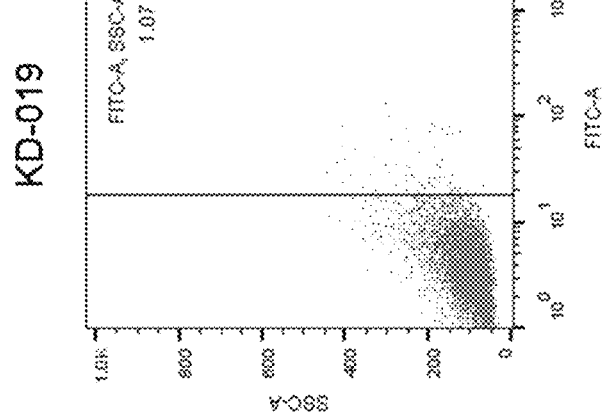
Figure 4A:
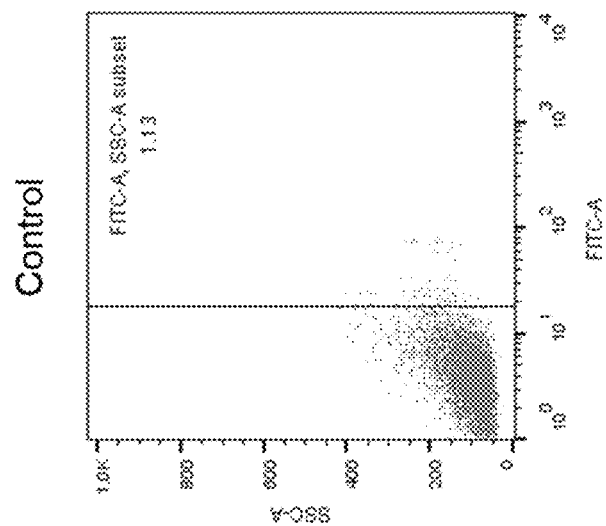
Figure 6A:
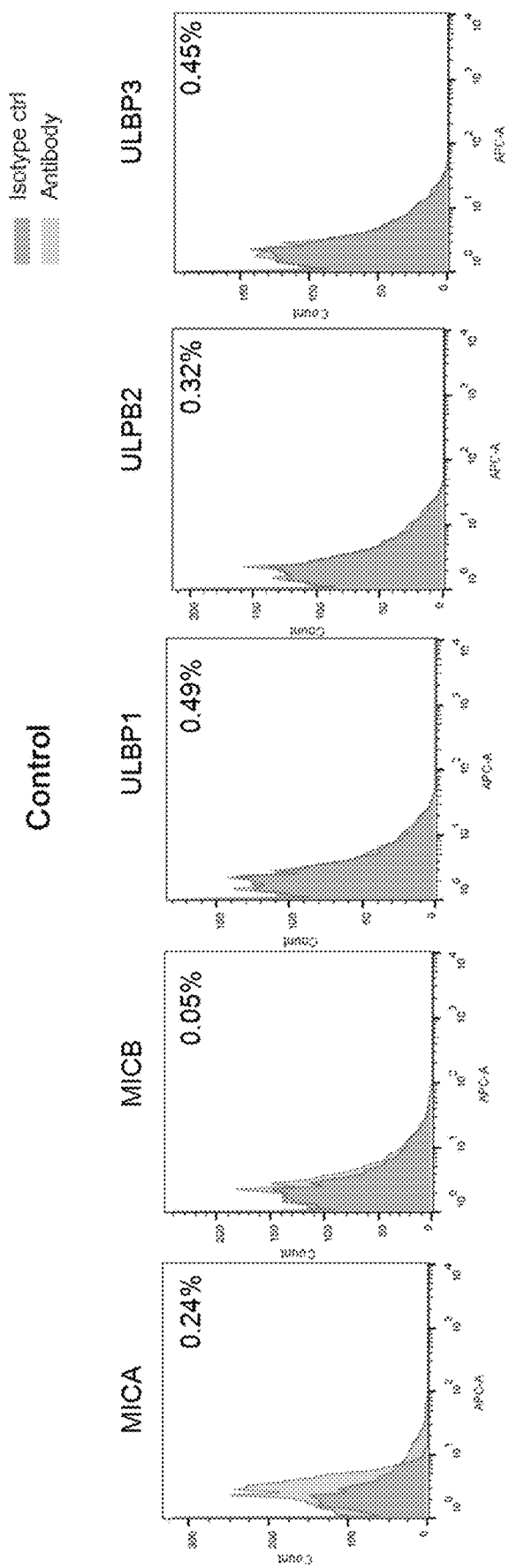
[FIGS. 6A, 6B, 6C, 6D, 6E, 6F, 6G, 6H, 6I and 6J depict the expression of major subtypes MicA, MicB, ULBP1, ULBP2 and ULBP3 of NKG2DLs detected in tumor cells such as liver cancer, ovarian cancer, gastric cancer, prostate cancer, lung cancer, breast cancer and glioblastoma.
Figure 6B:
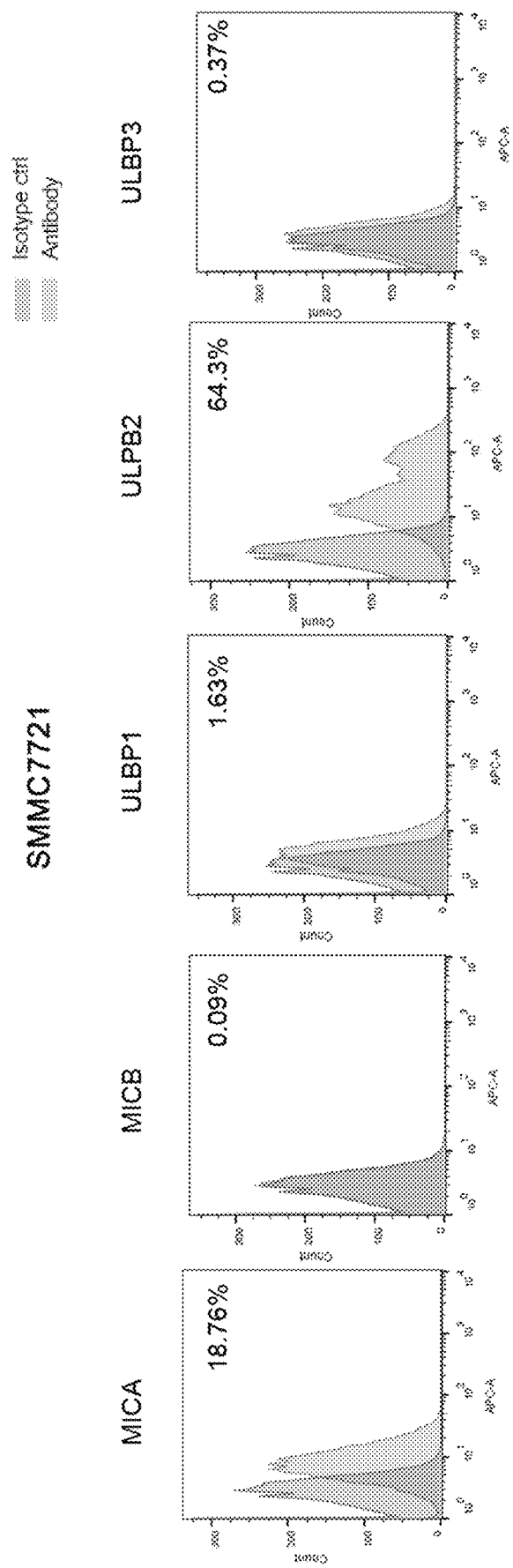
Figure 6C:
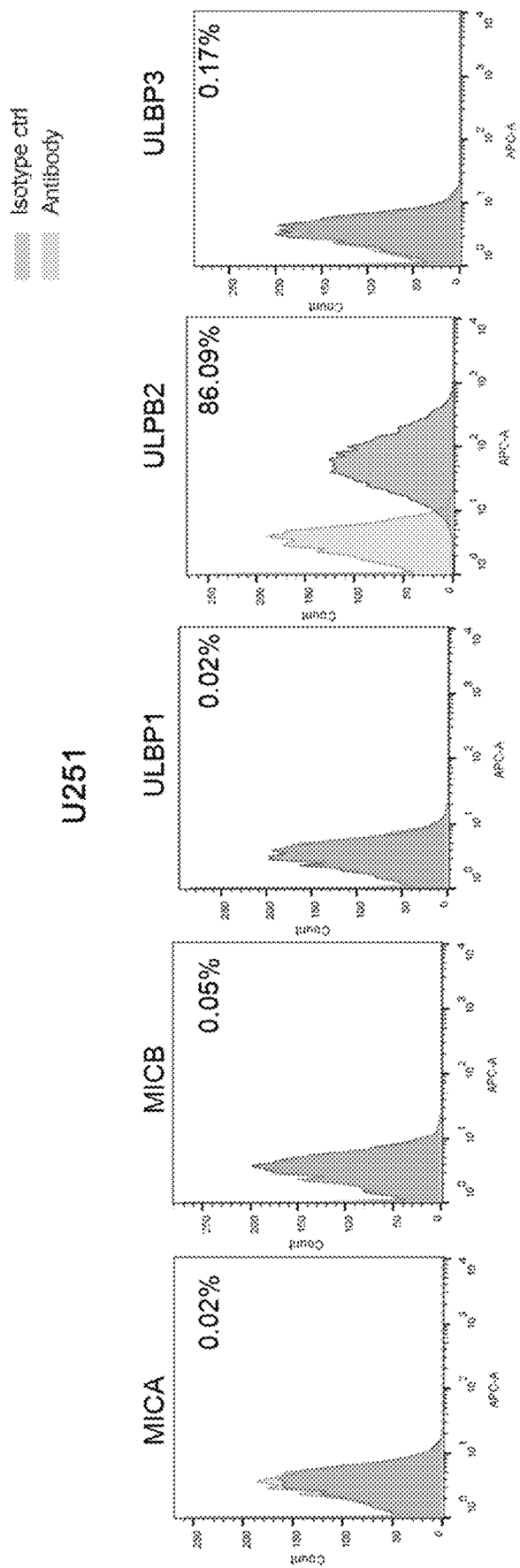
Figure 6D:
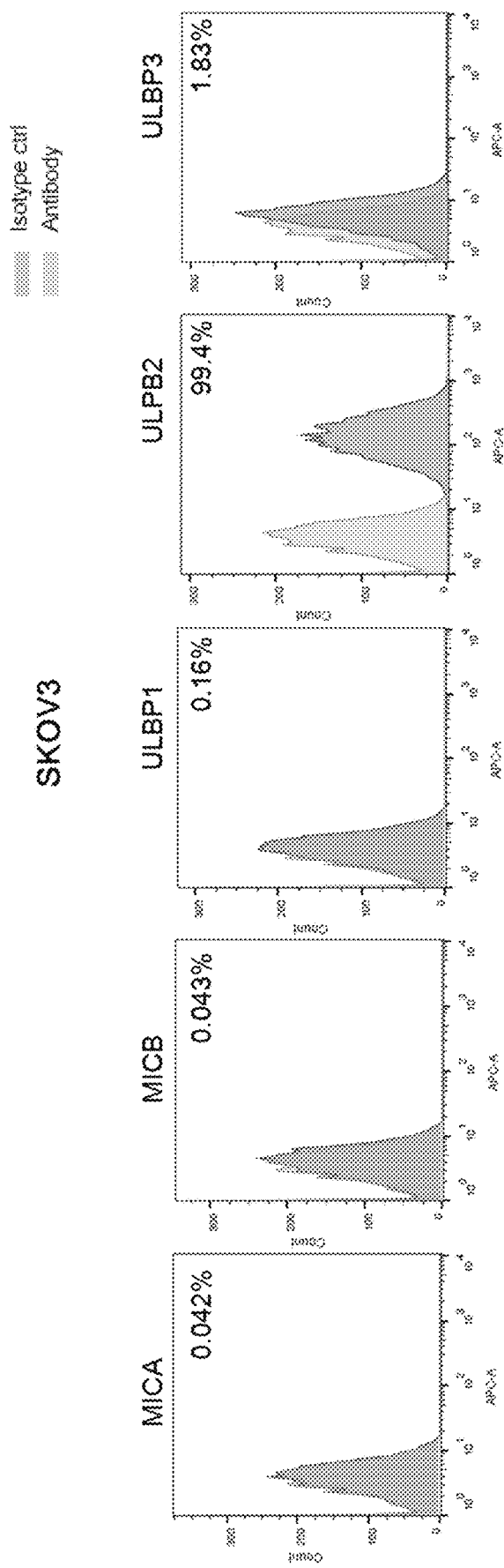
Figure 6E:
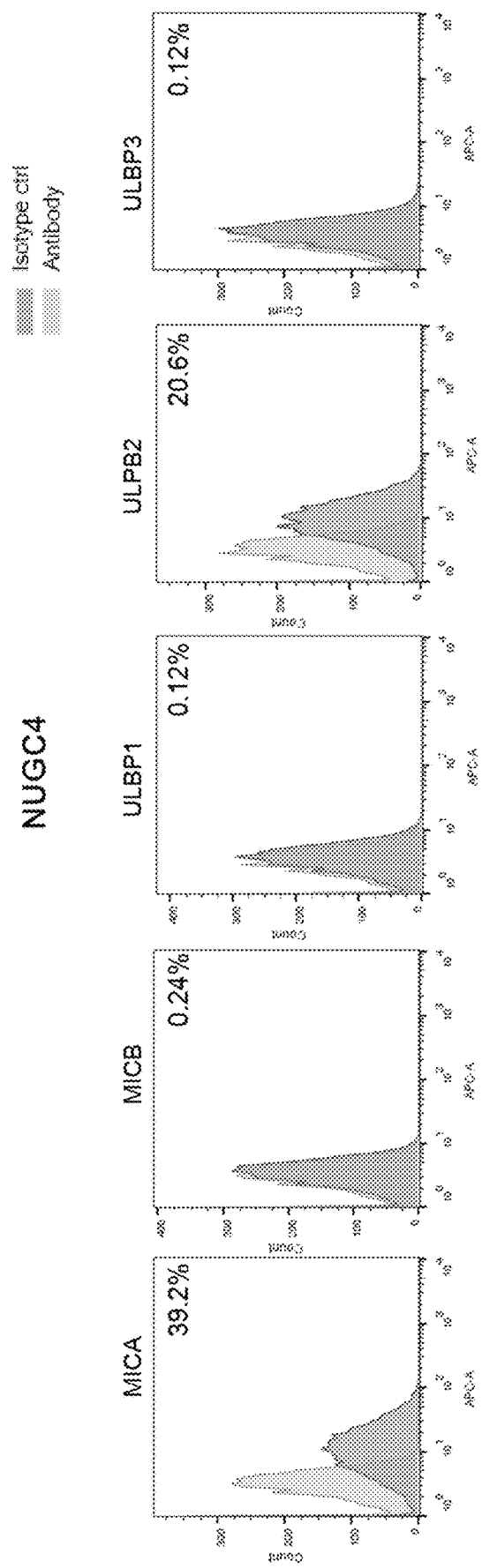
Figure 6F:
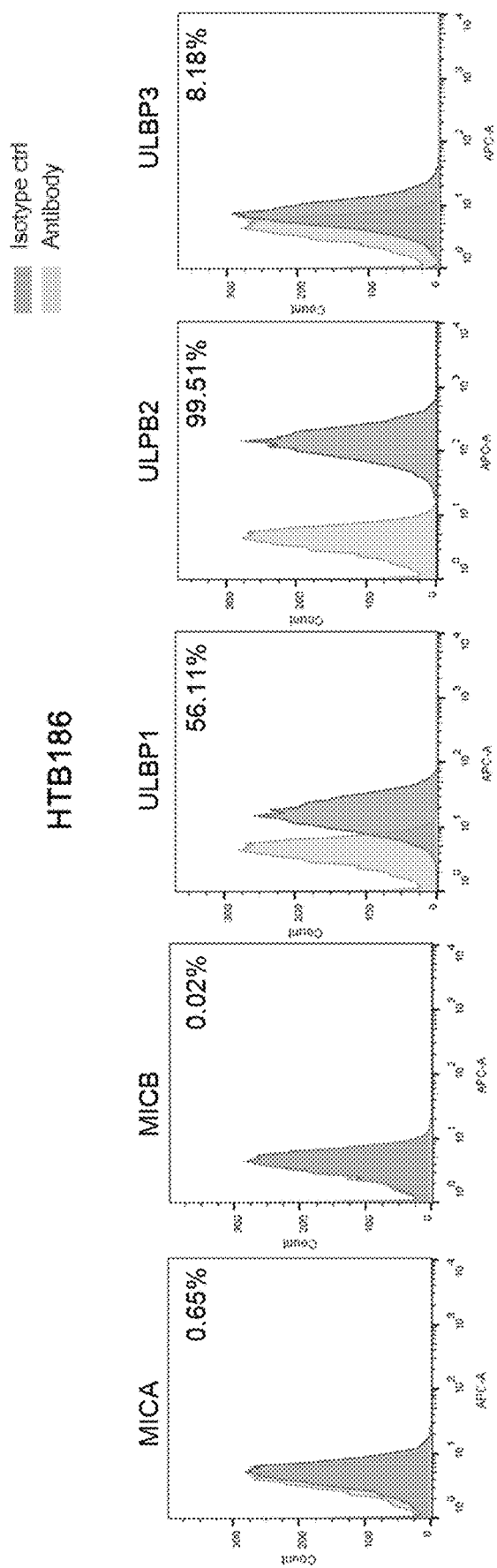
Figure 6G:
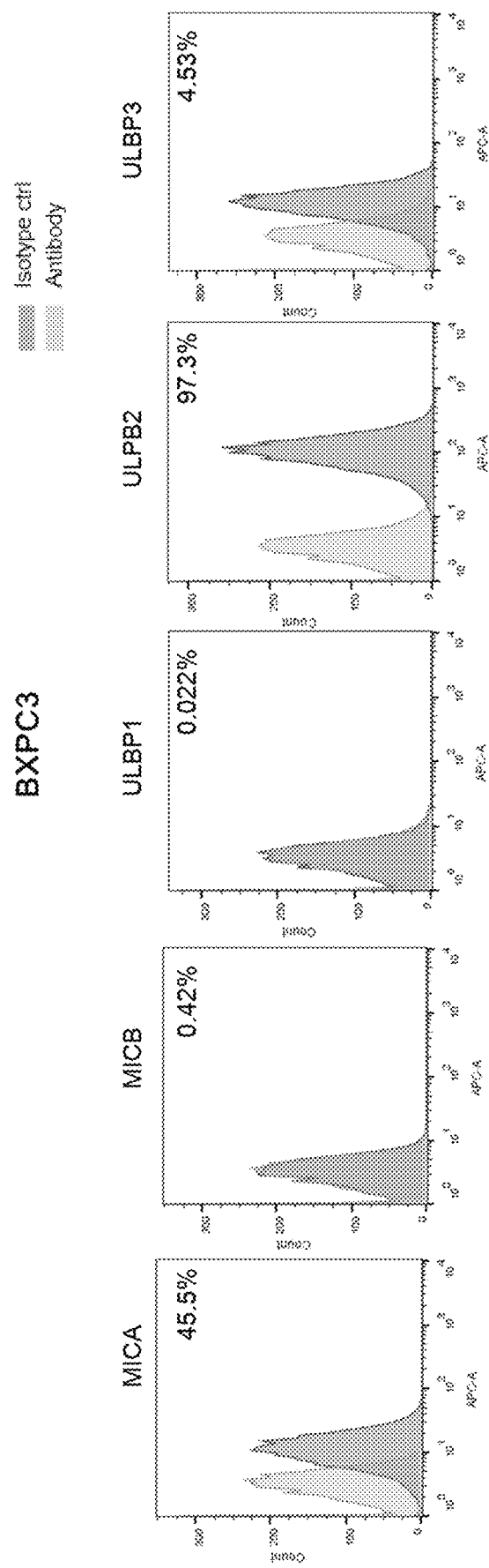
Figure 6H:
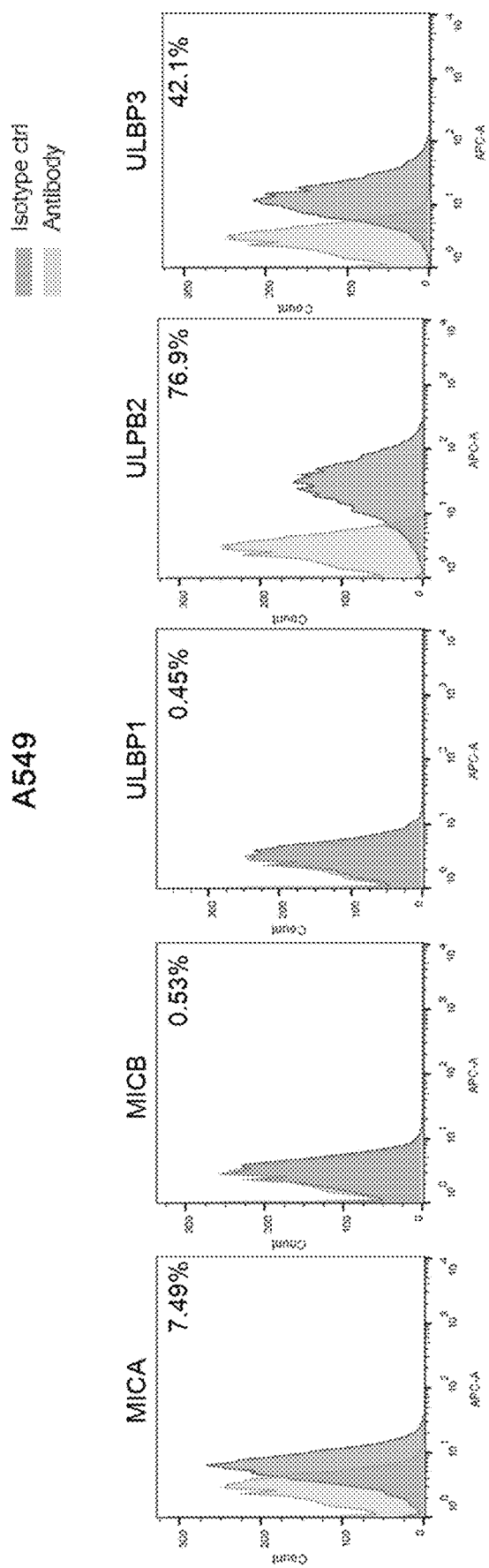
Figure 6I:
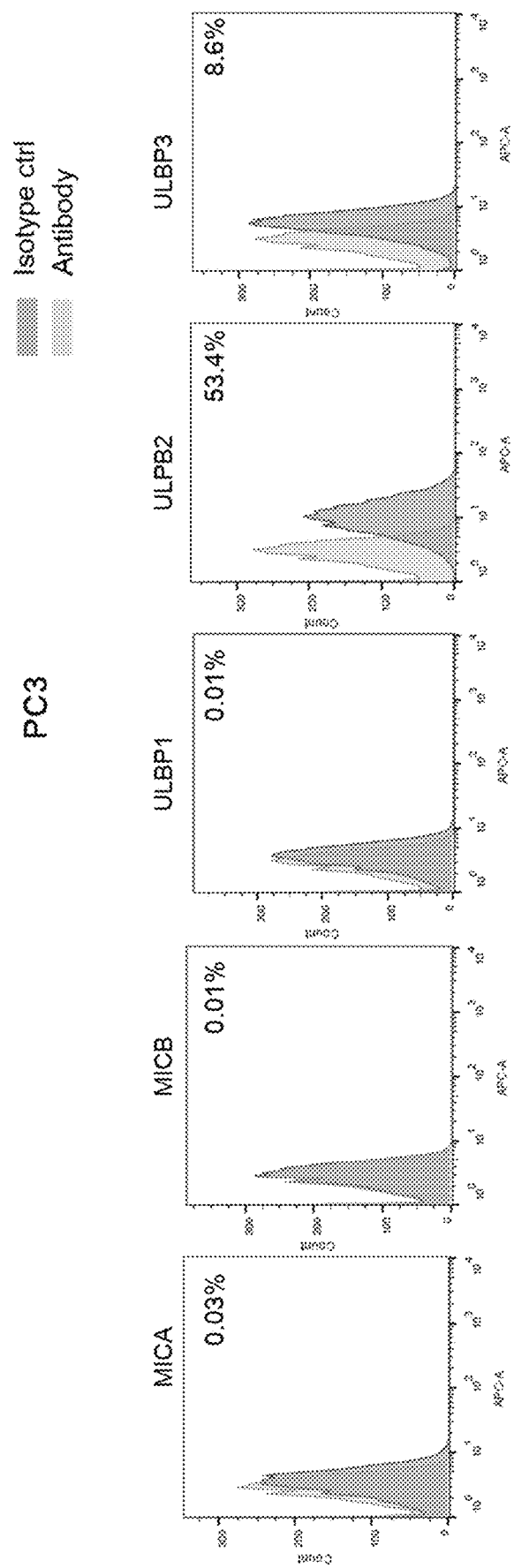
Figure 6J:
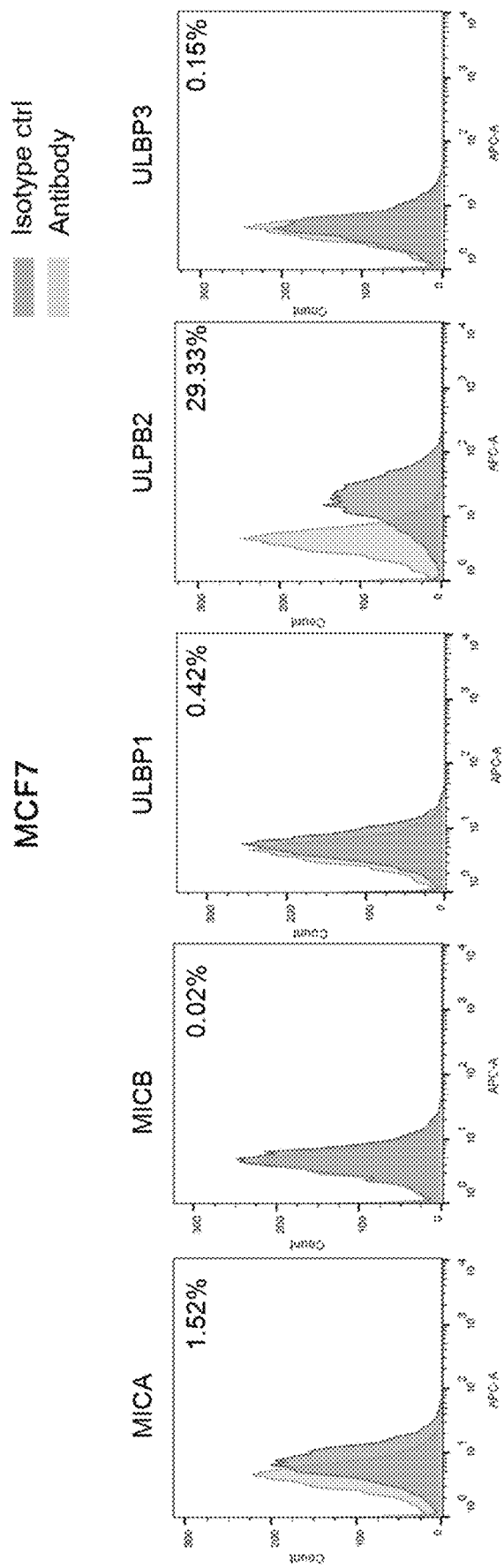

Then, the 7-AAD/CFSE cytotoxicity test kit (purchased from Biovision, catalogue number: K315-100) was used to test the cell activity of the prepared CAR-T cells according to the operation instructions of the kit. Flow cytometry data showed that the activity of KD-025 CAR-T cells was more than 95% (FIG. 4).

And then, the expression of CAR after infection was detected by flow cytometry.

Blank control group: T cells without virus infection,

KD-019 control group: specific CAR-T cells targeting CD19,

Group KD-025: specific CAR-T cells targeting NKG2DL.

The detecting cells to be collected during the preparation of cells.

After washing twice with PBS, the above experimental group and the control group were suspended in FACS solution (comprising 0.1% sodium azide and 0.4% BSA PBS).

According to the antibody instructions, the anti-human NKG2D antibody (APC Mouse Anti-Human NKG2D, 558071, BD) labeled with APC was added to the cell suspension of control group and the cell group detected, and incubated at 4° C. for 60 mins. Flow cytometry (BD FacsCanto II) was used to count the stained cells and then FlowJo software was used to analyze the results.

The results from flow cytometry as FIG. 5 showed, which proved that the cells to be detected in the collection of embodiment 4 expressing the specific chimeric antigen receptor targeting NKG2DL.

Application Examples for Effect Data Thereof

The tumor cell line (also known as target cell line): hepatoma cell SMMC7721 (purchased from Cobioer, Nanjing), and glioblastoma U251 cell (purchased from cells resource center the Shanghai Institutes of life sciences, Chinese academy of sciences), and ovarian cancer cell SKOV3 (purchased from Kunming Institute of animal science, Chinese academy of sciences), and gastric cancer cell NUGC4 (purchased from Cobioer, Nanjing), and Medulloblastoma cell HTB186 (purchased from Jennio, Guangzhou), and pancreatic cancer cell BXPC3 (purchased from Jennio, Guangzhou), lung cancer cell A549 (purchased from Kunming Institute of animal science, Chinese academy of sciences), and prostate cancer cell PC3 (purchased from Kunming Institute of animal science, Chinese academy of sciences), and breast cancer cell MCF7 (purchased from Kunming Institute of animal science, Chinese academy of sciences).

First, we detected the expression of NKG2DL major subtypes MicA, MicB, ULBP1, ULBP2 and ULBP3 in various target tumor cell lines. Tumor cells collected by trypsin digestion were washed twice with PBS and suspended in FACS solution (comprising 0.1% sodium azide and 0.4% BSA PBS). After cells counted and adjusted to centration to $1\times10^6$ cells/ml, MicA (R&D Systems, FAB1300A-025), MicB (R&D systems, FAB1599A-025), ULBP1 (R&D Systems, FAB1380A), ULBP2 (R&D Systems, FAB1298A), ULBP3 (R&D Systems, FAB1517A) antibody and homotypic control (R&D Systems, IC003A) was added respectively and incubated at 4° C. degrees for 60 mins. After washed twice with PBS and suspended in FACS solution, flow cytometry (BD FacsCanto II) detected the fluorescence of cells and analyzed the results by FlowJo software, which results were shown in FIG. 6 (another note: in FIG. 6, the abscissa showed APC fluorescence intensity; the ordinate represented the number of cells). The results showed that the test tumor cell lines showed high expression of NKG2DL antigen, whereas the control group had almost no expression.

Next, using the 7-AAD/CFSE cytotoxicity test kit (purchased from Biovision, catalogue number: K315-100), and according to the operation instructions of the kit to evaluate the killing of specific CAR-T cells targeted to the NKG2DL positive target cell line in the example 4.

Specifically, each target cell line was stained by CSFE fluorescence and was seeded in the culture plate at a concentration of $2\times10^4$ cells/ml per well. One experiment group and two control groups were set up for each target cell line, in which the experimental group added the cell suspension of specific CAR-T cells targeted to NKG2DL whereas the blank control group added T cells that was CD3+T cells obtained embodiment was not infected by the virus, and the KD-019 control group added unrelated CAR-T cells targeted to CD19.

In the experimental group, three specific effector to target ratios (10:1, 5:1 and 1:1) were applied to mix specific CAR-T cells targeting NKG2DL, which target NKG2DL, and target cells. Here, the term "effector to target ratio" refers to the ratio of effector cells (targeted to NKG2DL specific CAR-T cells) to target cells (tumor cells).

Also, the blank control group and the KD-019 control group also mixed T cells with target cells according to three different effector to target ratios.

After culture for 20 hours, the centrifuge went to remove the supernatant. After cleaning the cell precipitates that were stained by 7AAD. Flow cytometry (BD FacsCanto II) was used to count the staining cells, and the results were analyzed by FlowJo software.

Figure 7:
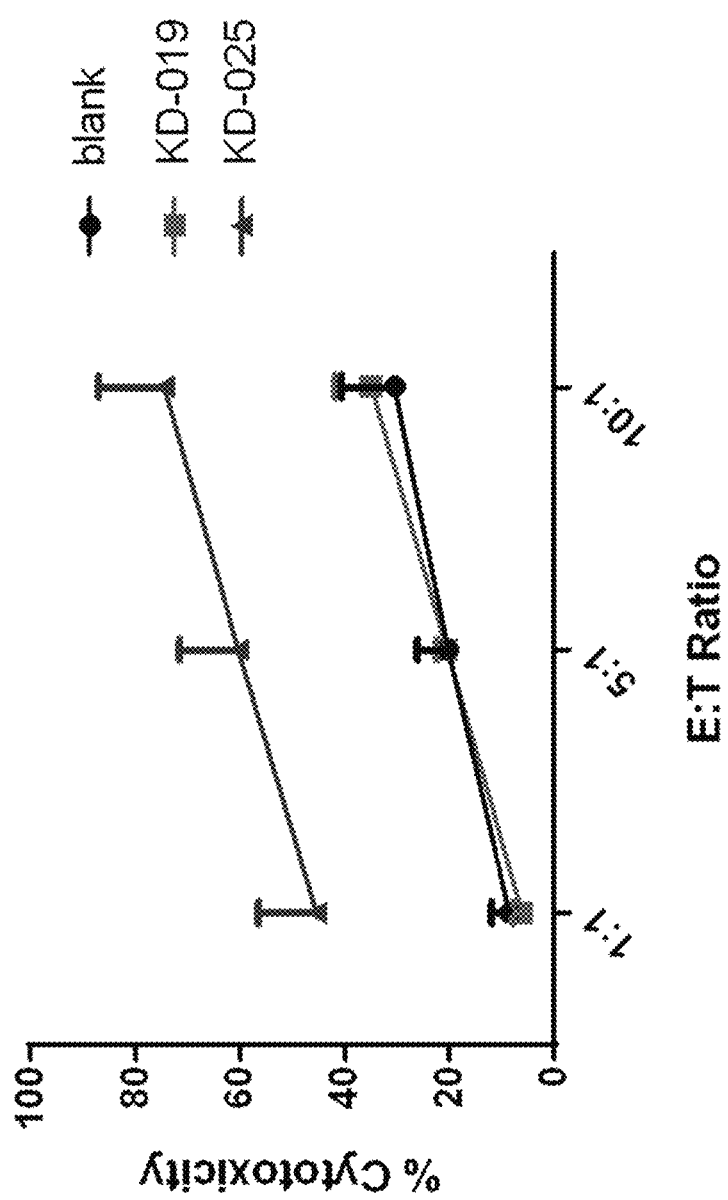
FIG. 7 depicts a specific CAR-T targeting NKG2DL positive hepatoma SMMC7721 cells, which shows the results of the killing activity to the target tumor cells in this application.

FIG. 7 shows the test results of tumor cell killing rate with hepatoma cell SMMC7721 as target cell. As can be seen from FIG. 7, the specific CAR-T cell KD-025 targeting NKG2DL in embodiment 4 has a significant killing effect on the hepatoma cell SMMC7721 (obviously higher than the two control groups), and the tumor killing rate is over 60% under the ratio of effector to target 10:1.

Figure 8:
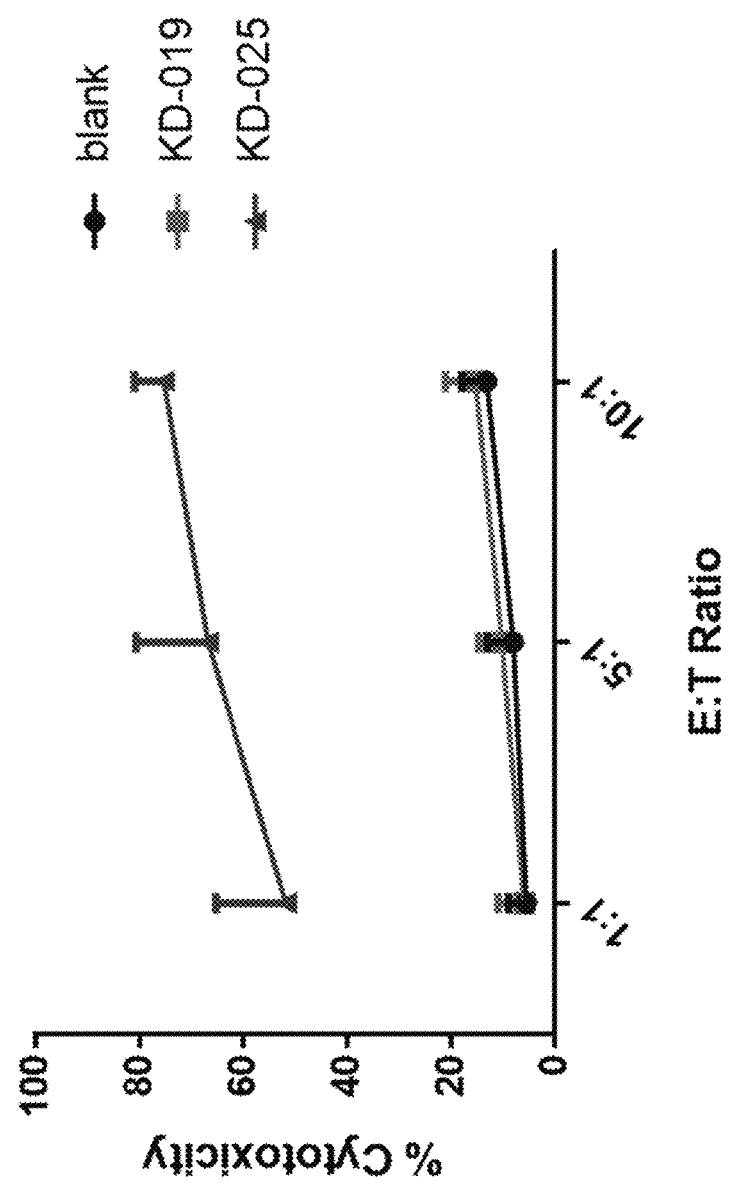
FIG. 8 depicts a specific CAR-T targeting NKG2DL positive glioblastoma U251 cells, which shows the results of the killing activity to the target tumor cells in this application.

FIG. 8 shows the test results of tumor cell killing rate with glioblastoma cell U251 as target cell. As can be seen from FIG. 8, the specific CAR-T cell KD-025 targeting NKG2DL in embodiment 4 has a significant killing effect on the glioblastoma cell U251 (obviously higher than the two control groups), and the tumor killing rate is over 70% under the ratio of effector to target 10:1.

Figure 9:
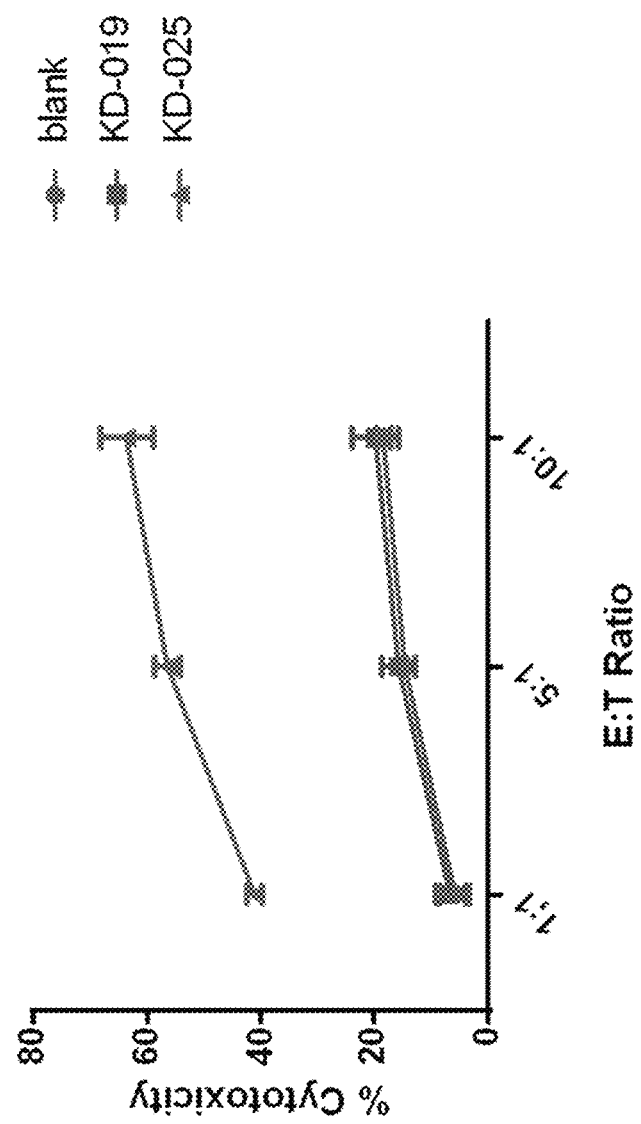
FIG. 9 depicts a specific CAR-T targeting NKG2DL positive ovarian cancer SKOV3 cells, which shows the results of the killing activity to the target tumor cells in this application.

FIG. 9 shows the test results of tumor cell killing rate with ovarian cancer cell SKOV3 as target cell. As can be seen from FIG. 9, the specific CAR-T cell KD-025 targeting NKG2DL in embodiment 4 has a significant killing effect on the Ovarian cancer cell SKOV3 (obviously higher than the two control groups), and the tumor killing rate is over 50% under the ratio of effector to target 10:1.

Figure 10:
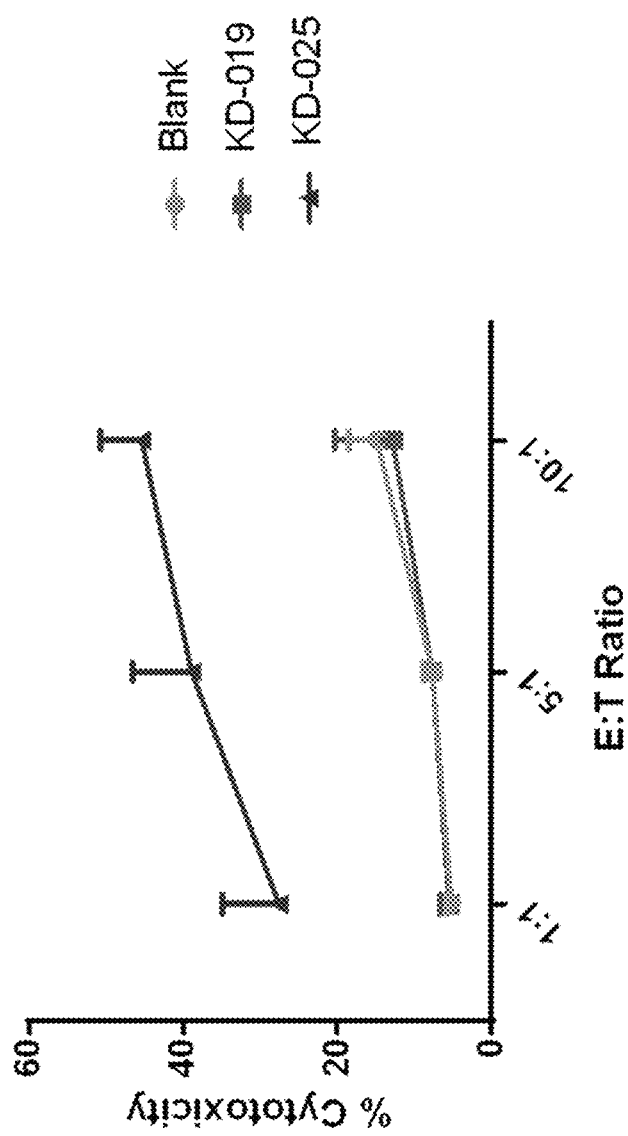
FIG. 10 depicts a specific CAR-T targeting NKG2DL positive gastric cancer NUGC4 cells, which shows the results of the killing activity to the target tumor cells in this application.

FIG. 10 shows the test results of tumor cell killing rate with gastric cancer cell NUGC4 as target cell. As can be seen from FIG. 10, the specific CAR-T cell KD-025 targeting NKG2DL in embodiment 4 has a significant killing effect on the gastric cancer cell NUGC4 (obviously higher than the two control groups), and the tumor killing rate is over 40% under the ratio of effector to target 10:1.

Figure 11:
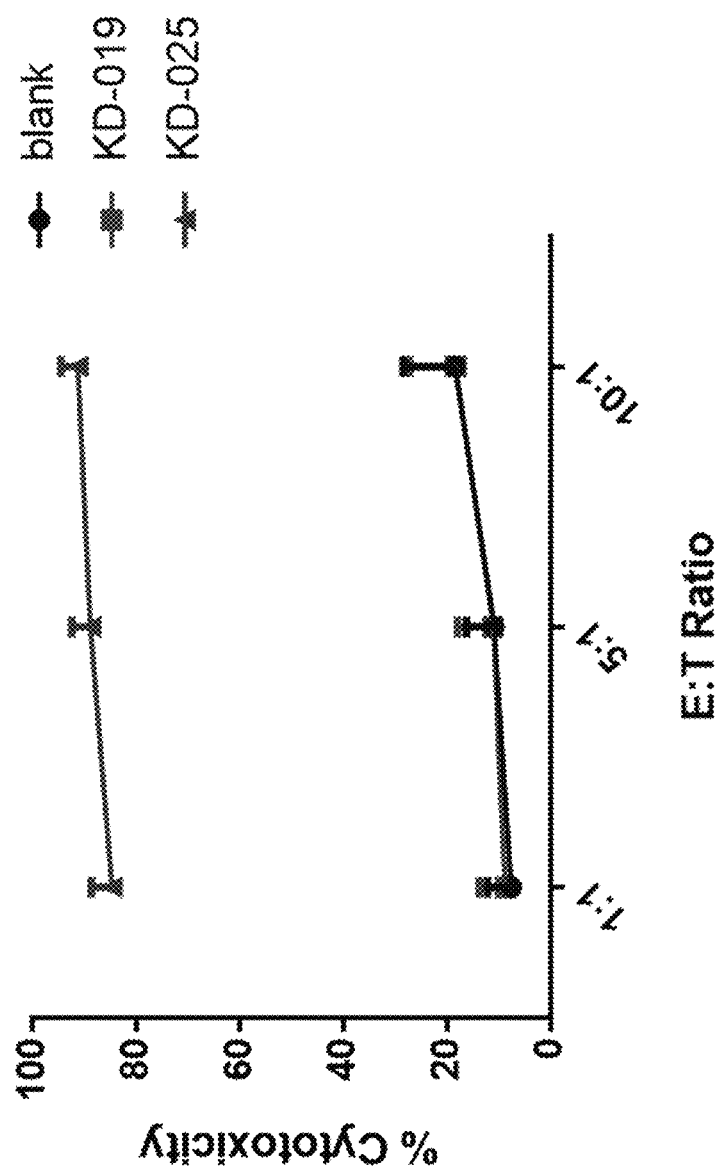
FIG. 11 depicts a specific CAR-T targeting NKG2DL positive medulloblastoma HTB186 cells, which shows the results of the killing activity to the target tumor cells in this application.

FIG. 11 shows the test results of tumor cell killing rate with medulloblastoma cell HTB186 as target cell. As can be seen from FIG. 11, the specific CAR-T cell KD-025 targeting NKG2DL in embodiment 4 has a significant killing effect on the medulloblastoma cell HTB186 (obviously higher than the two control groups), and the tumor killing rate is over 70% under the ratio of effector to target 10:1.

Figure 12:
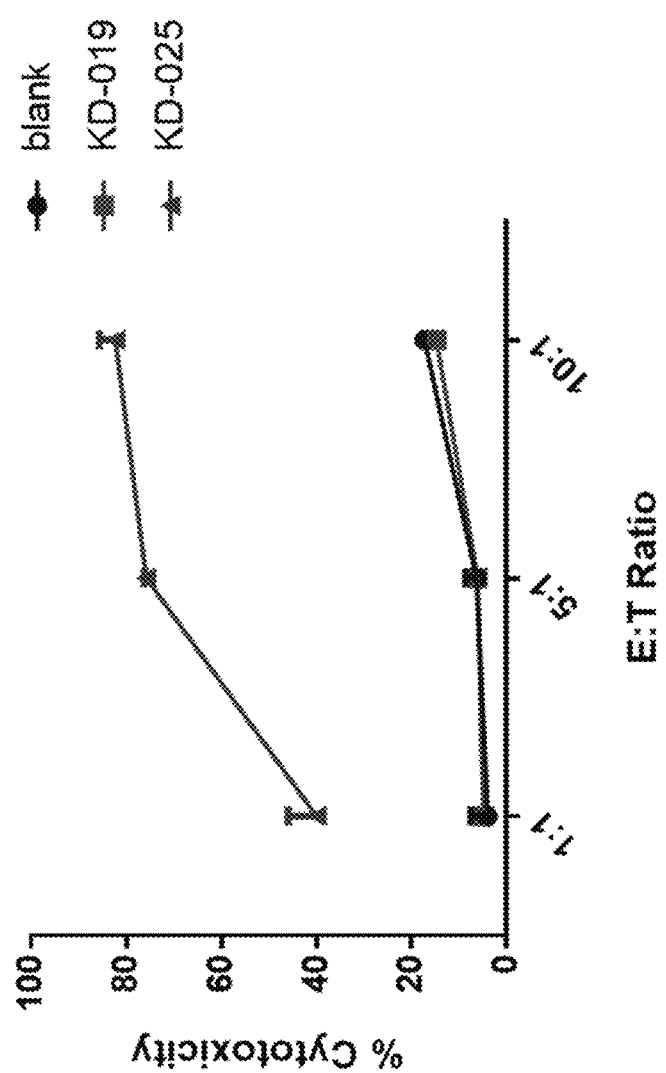
FIG. 12 depicts a specific CAR-T targeting NKG2DL positive pancreatic cancer BXPC3 cells, which shows the results of the killing activity to the target tumor cells in this application.

FIG. 12 shows the test results of tumor cell killing rate with pancreatic cancer cell BXPC3 as target cell. As can be seen from FIG. 12, the specific CAR-T cell KD-025 targeting NKG2DL in embodiment 4 has a significant killing effect on the pancreatic cancer cell BXPC3 (obviously higher than the two control groups), and the tumor killing rate is over 70% under the ratio of effector to target 10:1.

Figure 13:
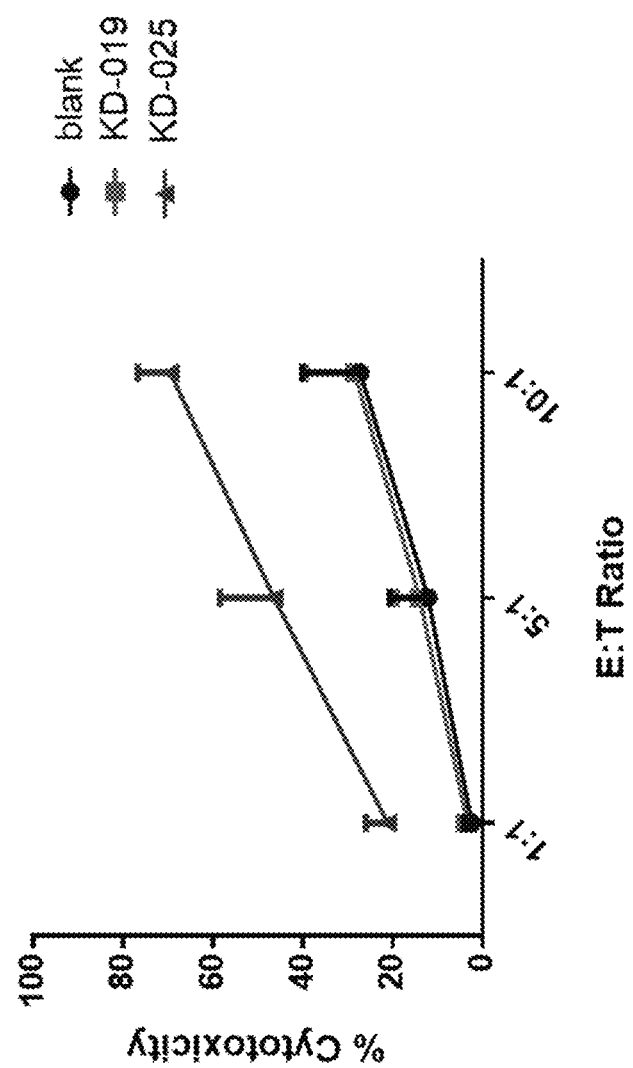
FIG. 13 depicts a specific CAR-T targeting NKG2DL positive lung cancer A549 cells, which shows the results of the killing activity to the target tumor cells in this application.

FIG. 13 shows the test results of tumor cell killing rate with lung cancer cell A549 as target cell. As can be seen from FIG. 13, the specific CAR-T cell KD-025 targeting NKG2DL in embodiment 4 has a significant killing effect on the lung cancer cell A549 (obviously higher than the two control groups), and the tumor killing rate is over 40% under the ratio of effector to target 10:1.

Figure 14:
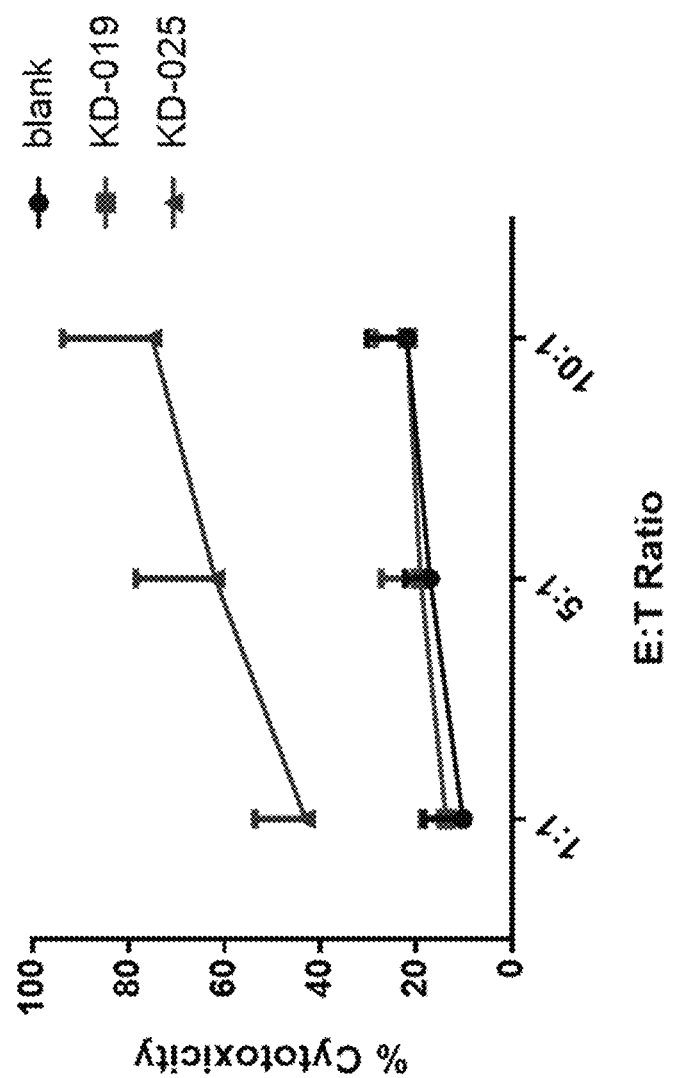
FIG. 14 depicts a specific CAR-T targeting NKG2DL positive prostate cancer PC3 cells, which shows the results of the killing activity to the target tumor cells in this application.

FIG. 14 shows the test results of tumor cell killing rate with prostate cancer cell PC3 as target cell. As can be seen from FIG. 14, the specific CAR-T cell KD-025 targeting NKG2DL in embodiment 4 has a significant killing effect on the prostate cancer cell PC3 (obviously higher than the two control groups), and the tumor killing rate is over 70% under the ratio of effector to target 10:1.

Figure 15:
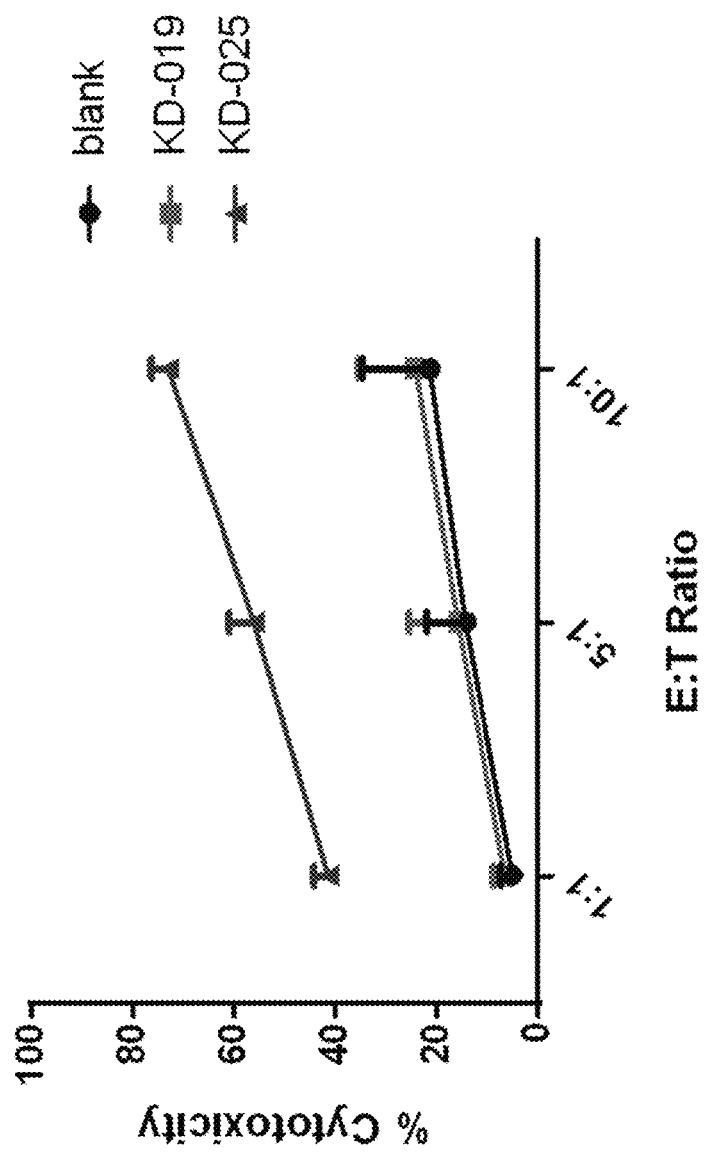
FIG. 15 depicts a specific CAR-T targeting NKG2DL positive breast cancer MCF7 cells, which shows the results of the killing activity to the target tumor cells in this application.

FIG. 15 shows the test results of tumor cell killing rate with breast cancer cell MCF7 as target cell. As can be seen from FIG. 15, the specific CAR-T cell KD-025 targeting NKG2DL in embodiment 4 has a significant killing effect on the breast cancer cell MCF7 (obviously higher than the two control groups), and the tumor killing rate is over 50% under the ratio of effector to target 10:1.

Figure 16A:
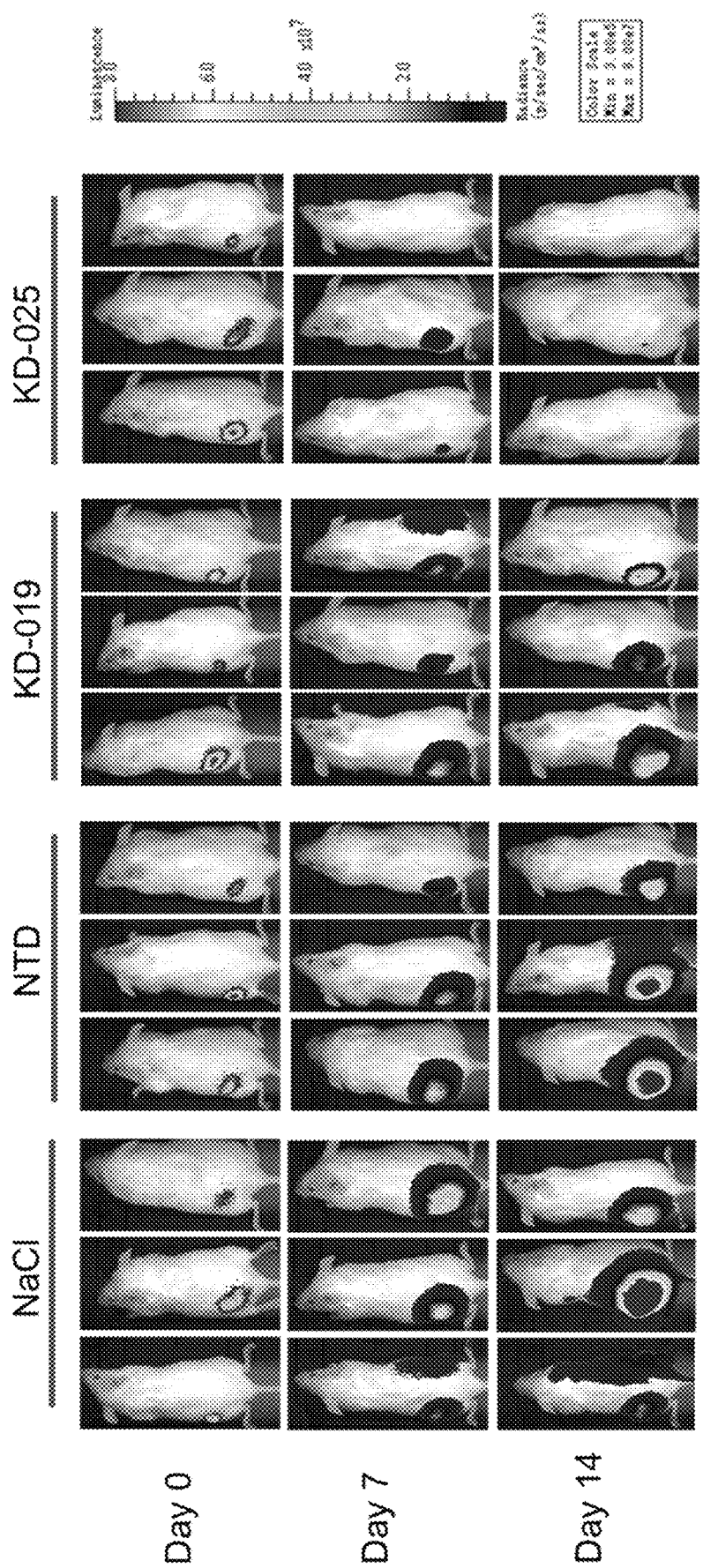
FIGS. 16A and 16B depict the killing results of the tumor xenograft animal model by subcutaneous infusing a specific CAR-T targeting NKG2DL positive hepatoma SMMC7721 cells, wherein the growth of subcutaneous transplantation tumor in xenograft NSG mice is detected as FIG. 16A shown whereas the fluorescence intensity of the tumor is detected as FIG. 16B shown.
Figure 16B:
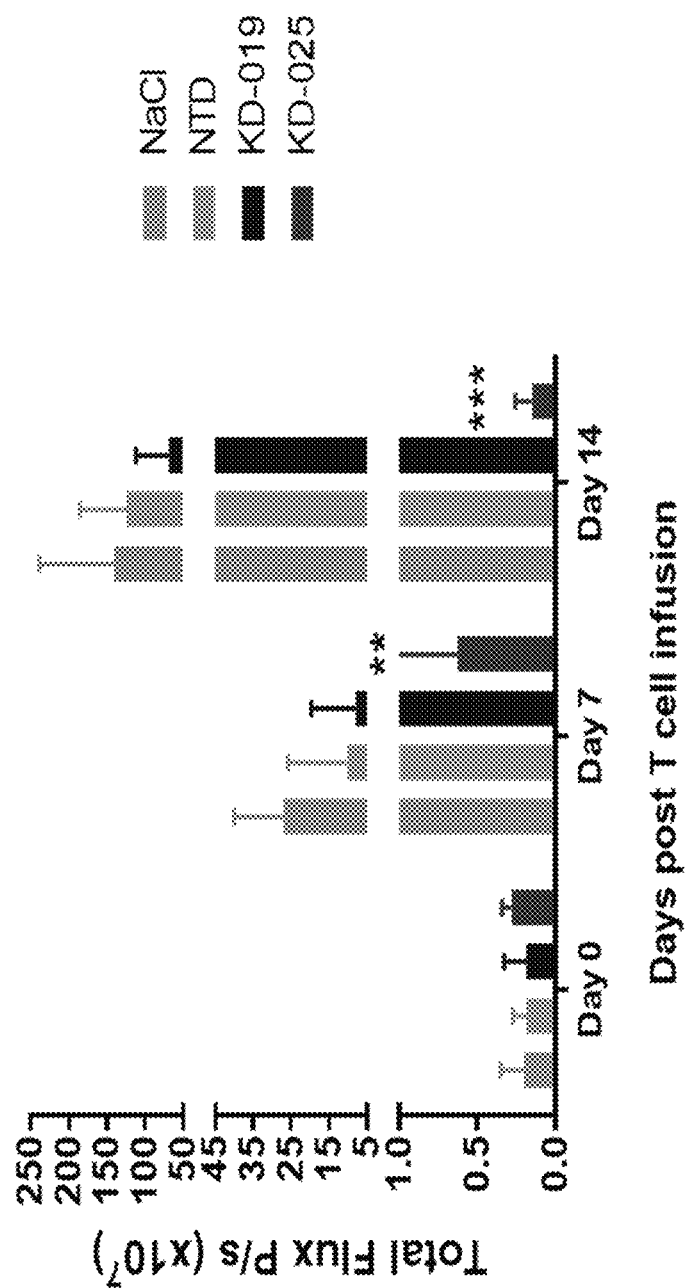

FIG. 16 shows the results of tumor suppressor test of CAR-T cells in NSG mice transplanted with SMMC7721 liver cancer cells. From FIG. 16, we can see that the specific CAR-T cell KD-025 targeted to NKG2DL in embodiment 4 has a significant inhibitory effect on liver cancer SMMC7721 xenografts. After inoculated tumor cells for 14 days, the tumor basically gone (FIG. 16A), and the fluorescence intensity of the tumor was significantly lower than that of the three control groups (FIG. 16B).

Figure 17A:
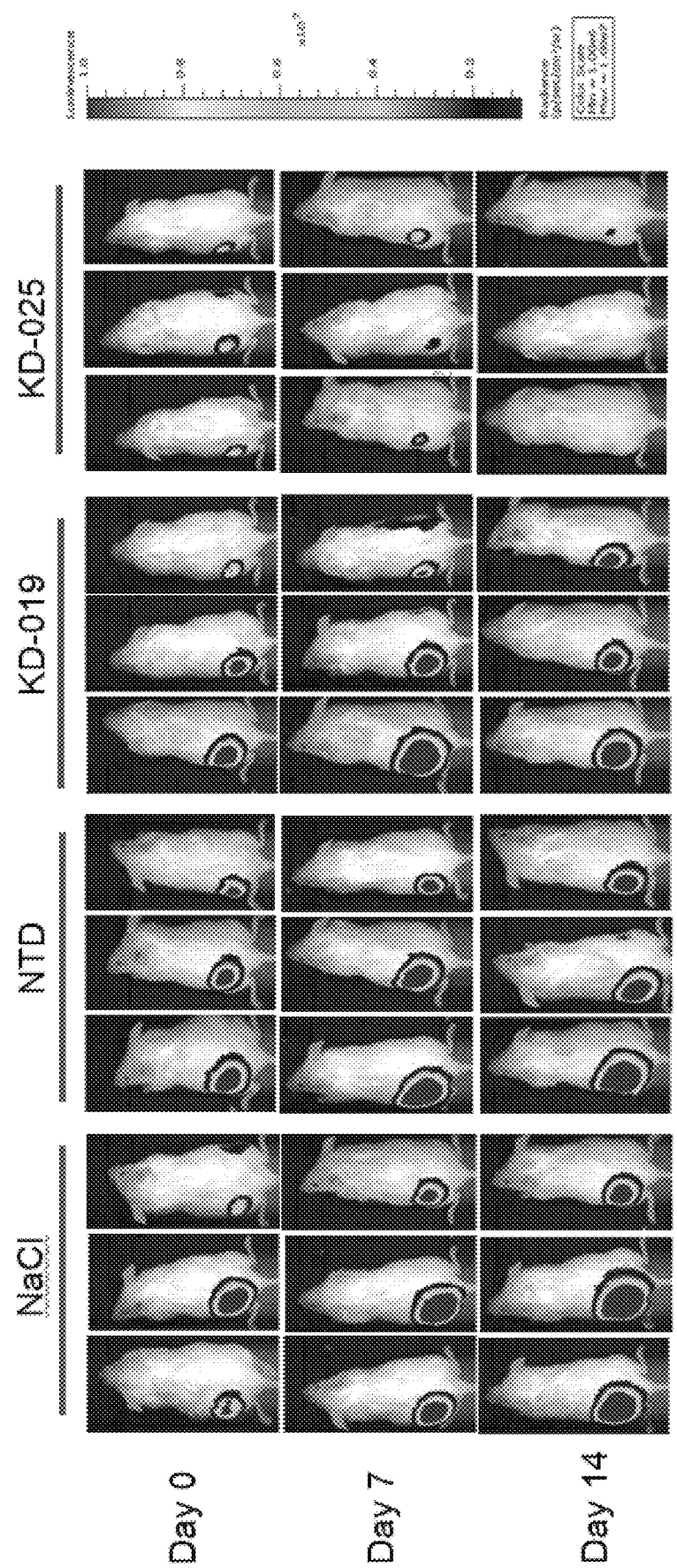
FIGS. 17A and 17B depict the killing results of the tumor xenograft animal model by subcutaneous infusing a specific CAR-T targeting NKG2DL positive glioblastoma U251 cells, wherein the growth of subcutaneous transplantation tumor in xenograft NSG mice is detected as FIG. 17A shown whereas the fluorescence intensity of the tumor is detected as FIG. 17B shown.
Figure 17B:
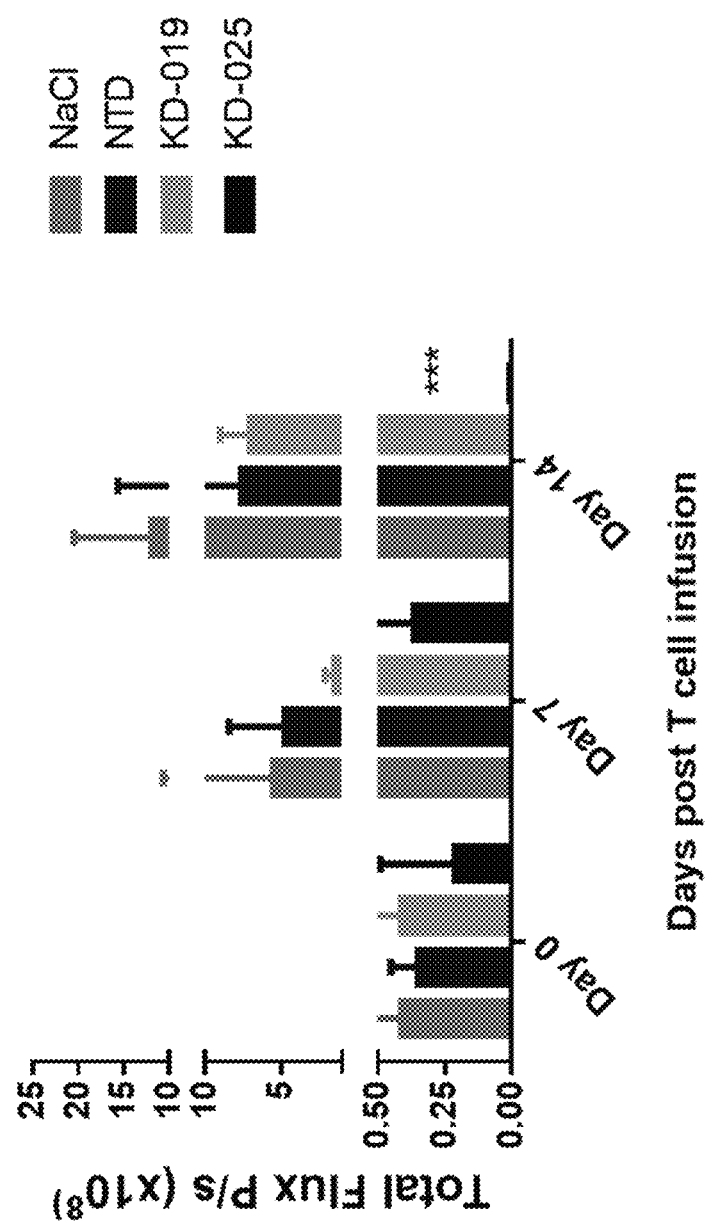

FIG. 17 shows the results of tumor suppressor test of CAR-T cells in NSG mice transplanted with glioblastoma U251 cells. From FIG. 17, we can see that the specific CAR-T cell KD-025 targeted to NKG2DL in embodiment 4 has a significant inhibitory effect on glioblastoma U251 xenografts. After inoculated tumor cells for 14 days, the tumor basically gone (FIG. 17A), and the fluorescence intensity of the tumor was significantly lower than that of the three control groups (FIG. 17B).

Figure 18A:
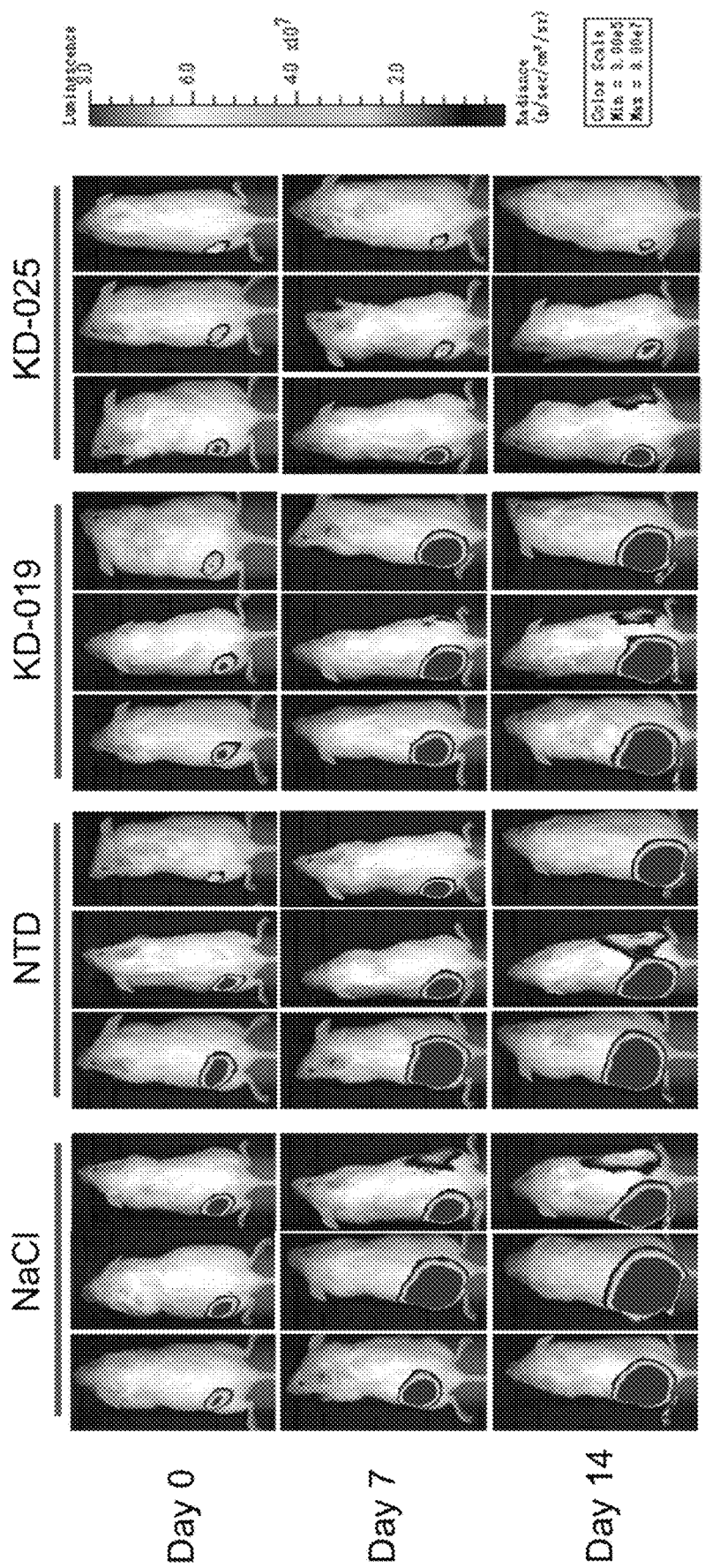
FIGS. 18A and 18B depict the killing results of the tumor xenograft animal model by subcutaneous infusing a specific CAR-T targeting NKG2DL positive ovarian cancer SKOV3 cells, wherein the growth of subcutaneous transplantation tumor in xenograft NSG mice is detected as FIG. 18A shown whereas the fluorescence intensity of the tumor is detected as FIG. 18B shown.
Figure 18B:
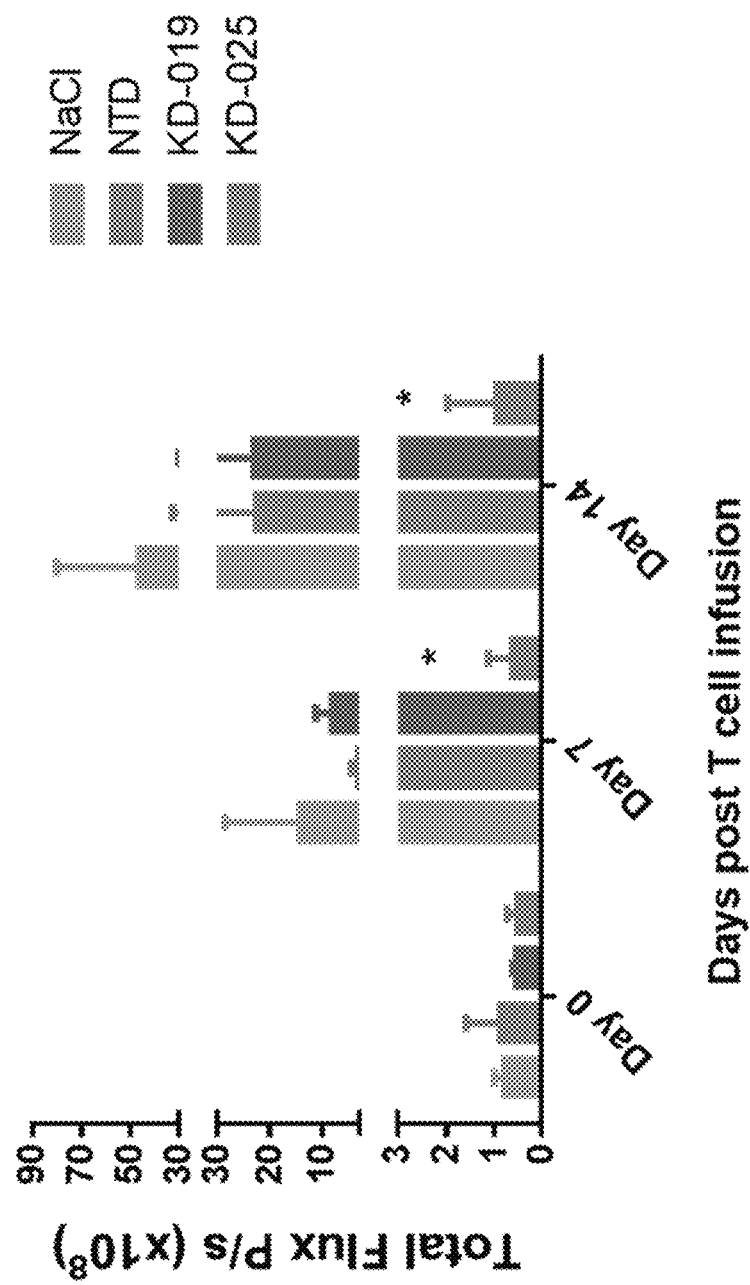

FIG. 18 shows the results of tumor suppressor test of CAR-T cells in NSG mice transplanted with SKOV3 ovarian cancer cells. From FIG. 18, we can see that the specific CAR-T cell KD-025 targeted to NKG2DL in embodiment 4 has a significant inhibitory effect on ovarian cancer SKOV3 xenografts. After inoculated tumor cells for 14 days, Tumor growth is obviously suppressed (FIG. 18A), and the fluorescence intensity of the tumor was obviously lower than that of the three control groups (FIG. 18B).

Figure 19A:
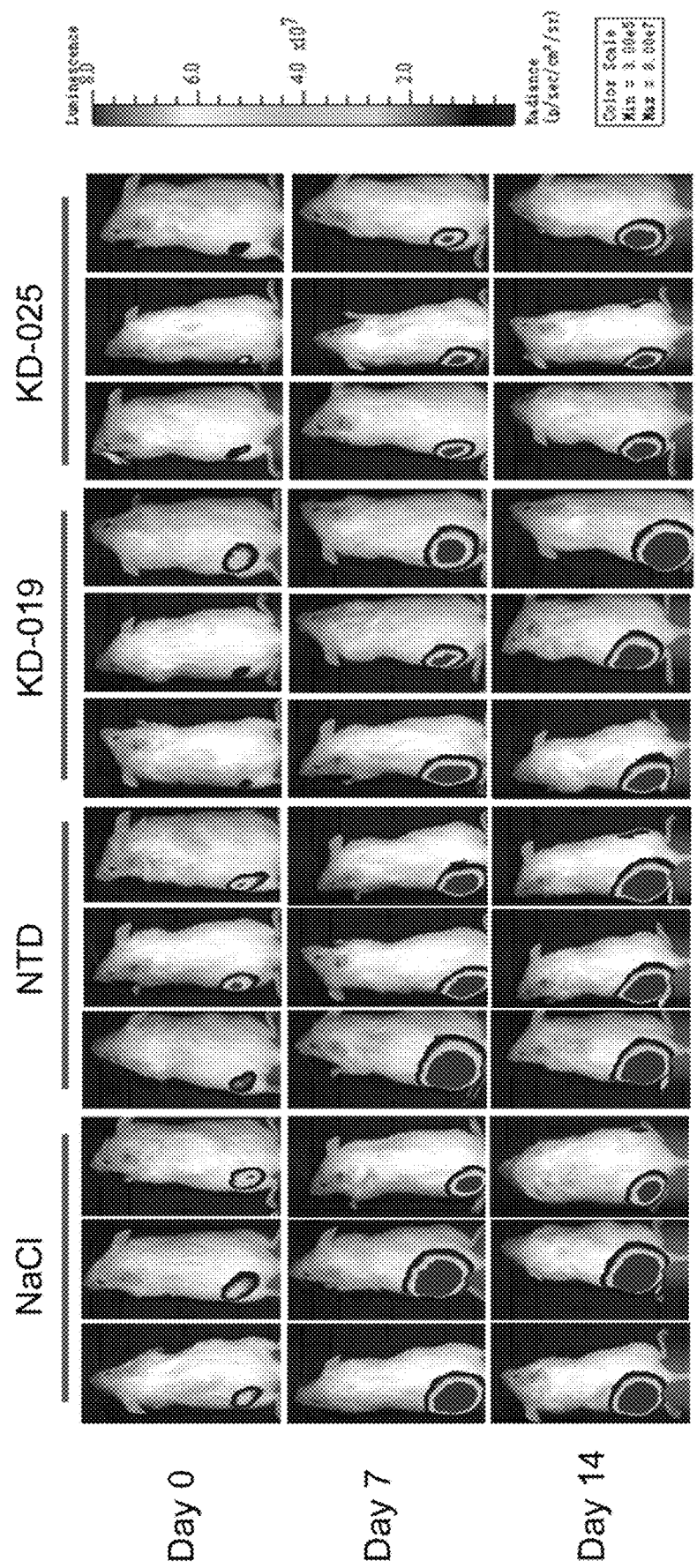
FIGS. 19A and 19B depict the killing results of the tumor xenograft animal model by subcutaneous infusing a specific CAR-T targeting NKG2DL positive gastric cancer NUGC4 cells, wherein the growth of subcutaneous transplantation tumor in xenograft NSG mice is detected as FIG. 19A shown whereas the fluorescence intensity of the tumor is detected as FIG. 19B shown.
Figure 19B:
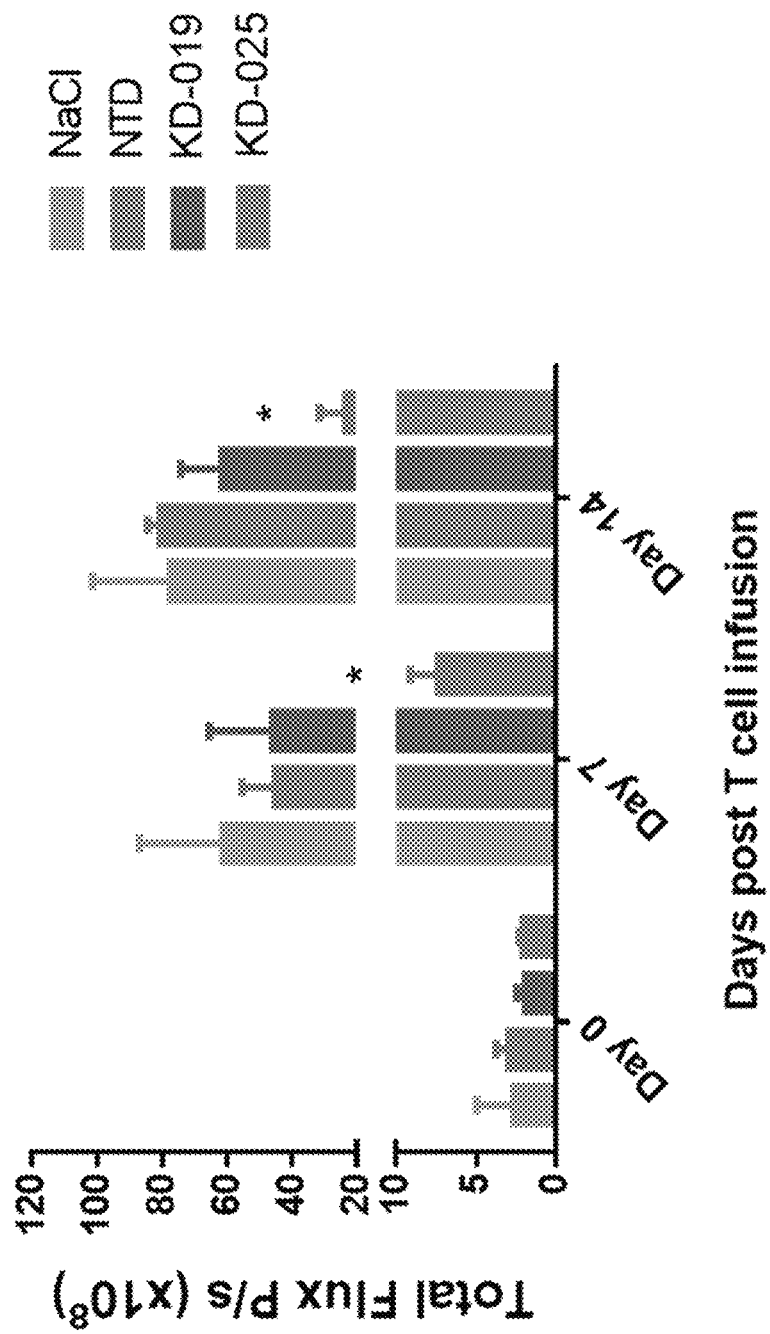

FIG. 19 shows the results of tumor suppressor test of CAR-T cells in NSG mice transplanted with NUGC4 gastric cancer cells. From FIG. 19, we can see that the specific CAR-T cell KD-025 targeted to NKG2DL in embodiment 4 has a significant inhibitory effect on gastric cancer NUGC4 xenografts. After inoculated tumor cells for 14 days, Tumor growth is suppressed (FIG. 19A), and the fluorescence intensity of the tumor was lower than that of the three control groups (FIG. 19B).

Figure 20A:
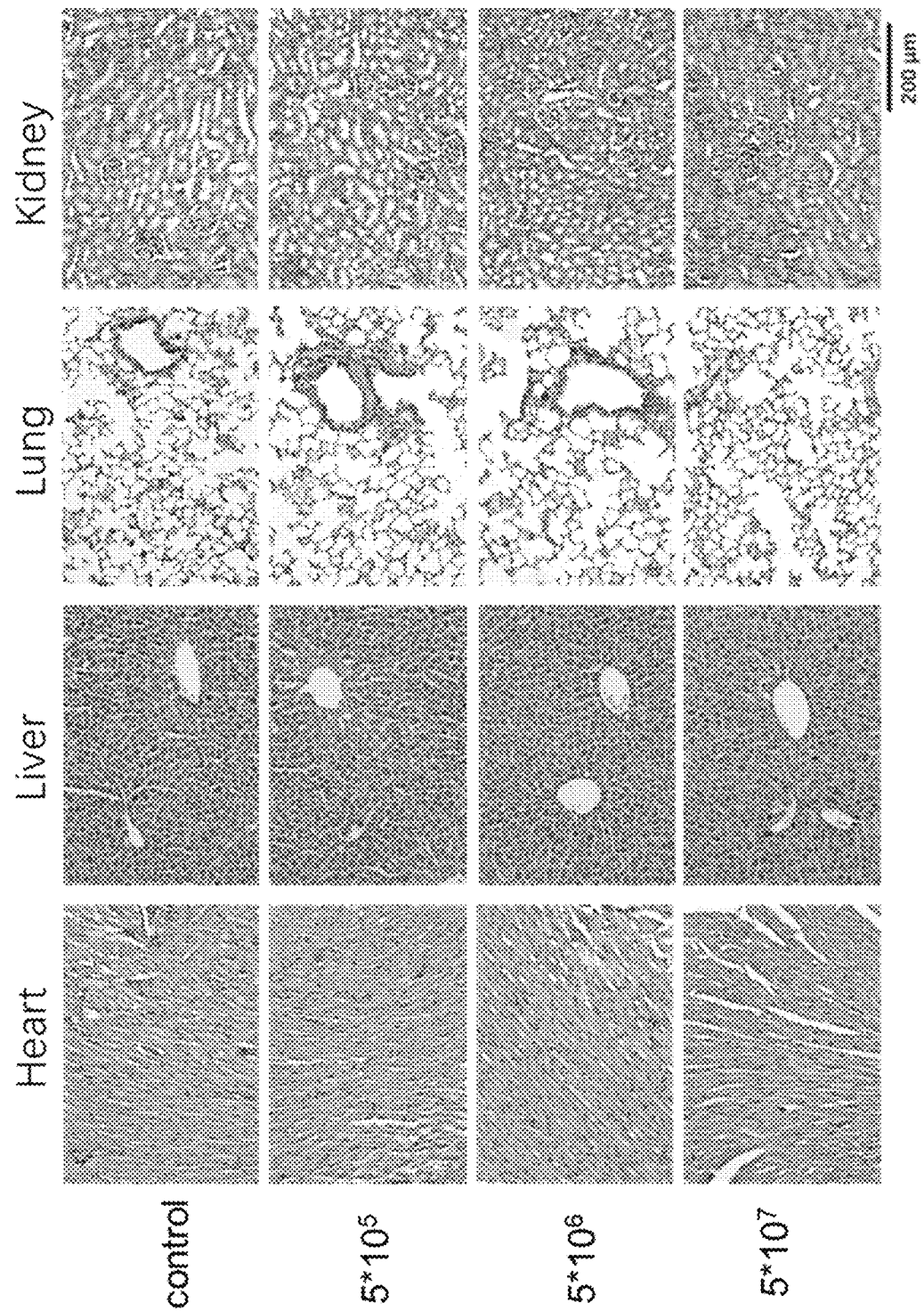
Figure 20B:
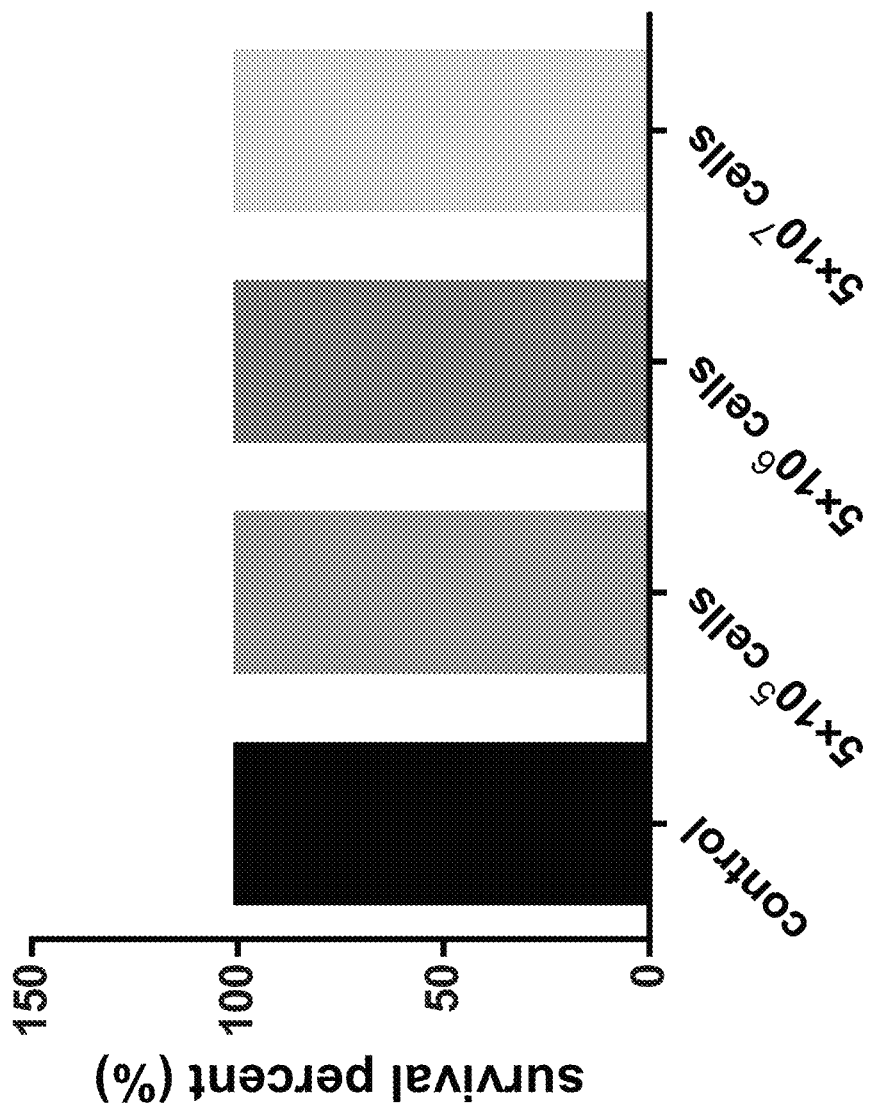

FIG. 20 shows the effects of different doses of KD-025 CAR-T cells on the main organs and survival term of mice. As can be seen from FIG. 20, the specific CAR-T cell KD-025 targeting NKG2DL in example 4 does not cause inflammation, edema and necrosis in the main organs of the mice, such as heart, liver, lung, and kidney (FIG. 20A), and there is no negative effect on the survival term of mice (FIG. 20B).

Figure 21:
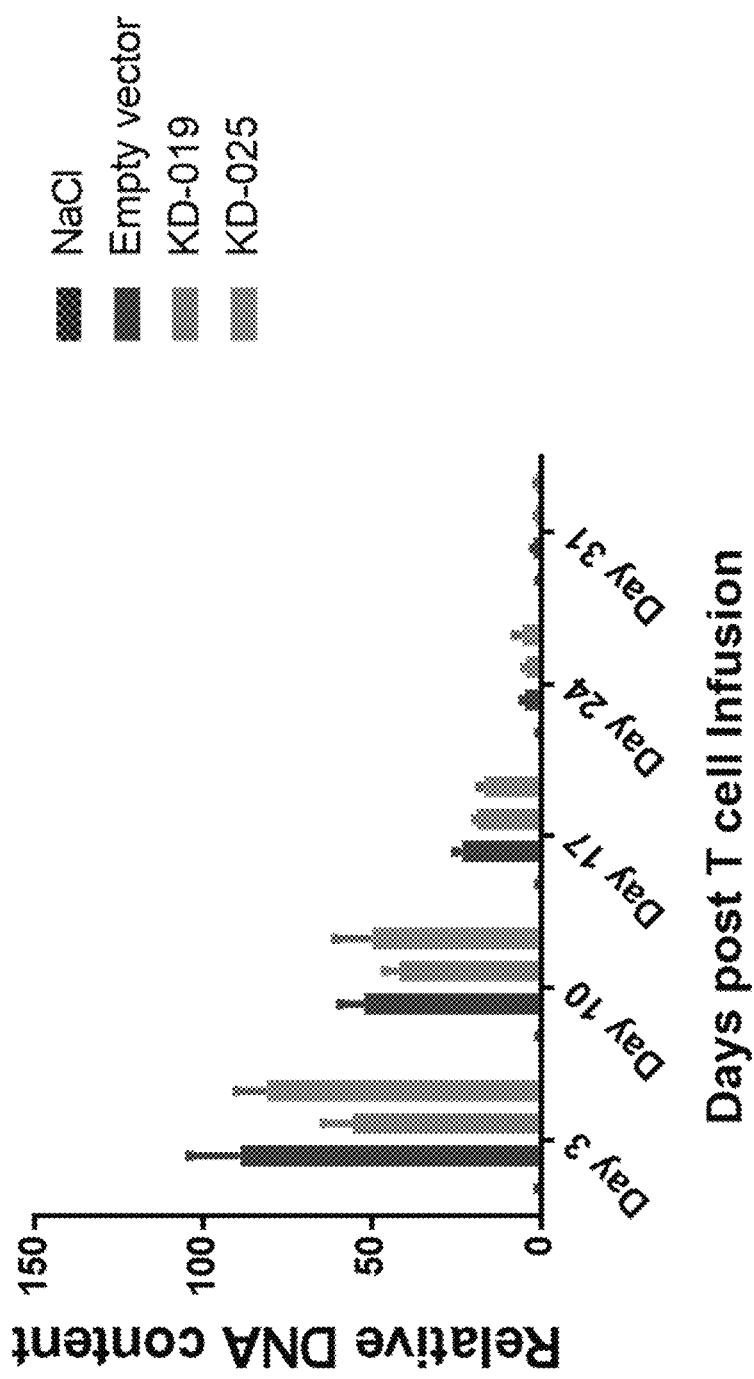
FIG. 21 depicts the persistence test result of KD-025 CAR in vivo by using B-NSG animals.

FIG. 21 shows the existence time of KD-025 CAR-T in mice. As can be seen from FIG. 21, the amount of existence in the control group and KD-025 CAR-T cells decreased to about 50% after 10 days of injection in mice, and decreased to about 25% after 17 days, and no residual CAR-T cells were detected after 31 days (FIG. 21).

Figure 22:
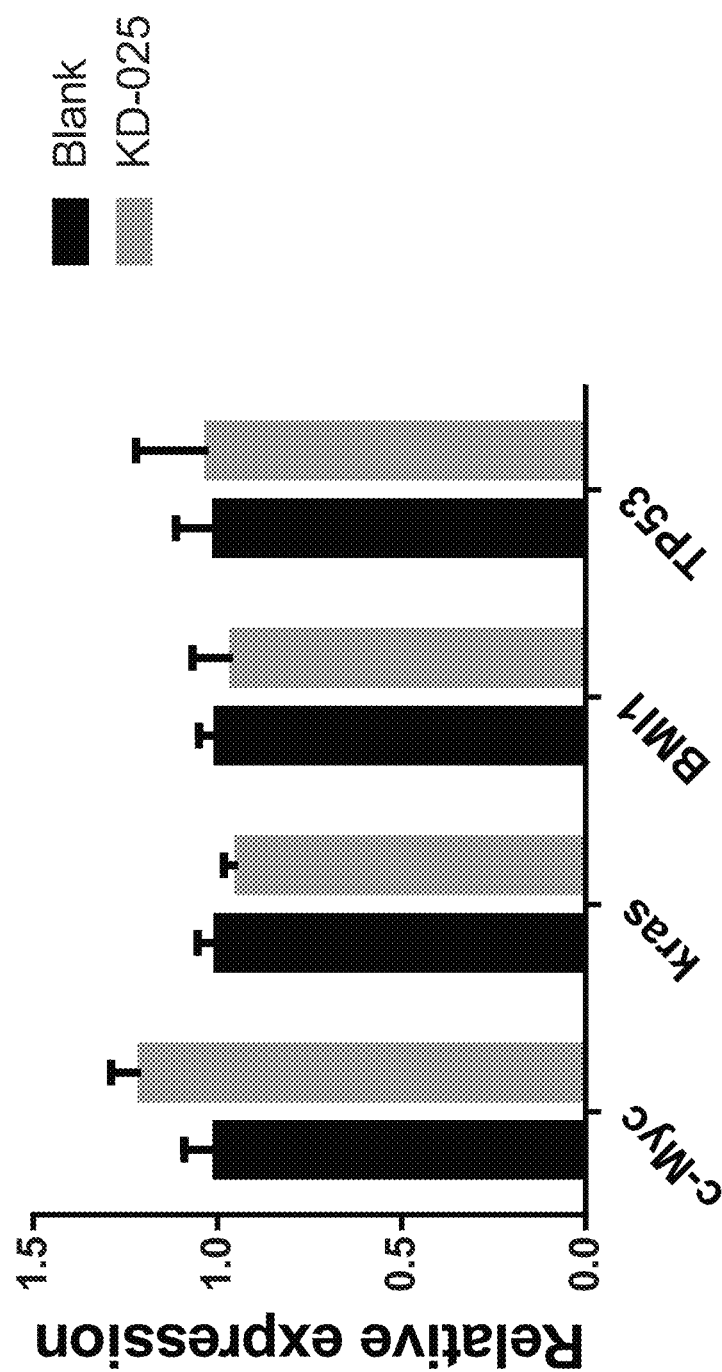
FIG. 22 depicts the detection of expression pattern of multiple oncogenes after KD-025 CAR virus infected T cells.

FIG. 22 shows the effect of KD-025CAR virus on the expression of oncogene after transfection of T cells. As can be seen from FIG. 22, the T cells transfected by the control group and KD-025 CAR virus were detected by real-time quantitative PCR analysis on the expression of the oncogene cMyc, KRAS BMl1 and TP53. It was found that the transfection of KD-025CAR virus to T cells did not change the expression level of oncogenes in the cells (FIG. 22).

From the results of the above FIGS. 7 to 19, it can be seen that the specific CAR-T cells of the target NKG2DL of the invention can specifically identify the NKG2DL positive tumor cells with a targeted killing capability.

Therefore, the specific chimeric antigen receptor of the target NKG2DL and the specific CAR-T cells of the targeted NKG2DL infected by its viral vector can be applied to the treatment of liver cancer, ovarian cancer, gastric cancer, lung cancer, prostate cancer, breast cancer, neuroglioma or neuroblastoma, pancreatic, bladder, and colon cancer, renal cell carcinoma, leukemia, lymphoma, multiple myeloma, melanoma, and their combinations.

It can be understood that although the instruction is described in the embodiment, not each embodiment comprises only one independent technical proposal. This description of the instruction is only to be clear, and the skilled in this field should take as a whole, and the technical solutions in embodiments can also be suitably combined to forms other embodiments can be understood by technicians in the field.

A series of detailed descriptions listed are only specific instructions for the embodiment of the invention. They are not used to limit the scope of protection of the invention. The equivalent embodiment methods or changes that are not separated from the topic of the invention should be comprised in the scope of the protection of the invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

```
<160> NUMBER OF SEQ ID NOS: 33

<210> SEQ ID NO 1
<211> LENGTH: 216
<212> TYPE: PRT
<213> ORGANISM: Artificial Sequence
<220> FEATURE:
<223> OTHER INFORMATION: The sequence is designed and synthesized

<400> SEQUENCE: 1

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Thr Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125
```

```
Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215

<210> SEQ ID NO 2
<211> LENGTH: 648
<212> TYPE: DNA
<213> ORGANISM: Homo sapiens

<400> SEQUENCE: 2
atggggtgga ttcgtggtcg gaggtctcga cacagctggg agatgagtga atttcataat      60
tataacttgg atctgaagaa gagtgatttt caacacgag ggcaaaagca agatgtccca     120
gtagtcaaaa gcaaatgtag agaaaatgca tctccatttt ttttctgctg cttcatcgct     180
gtagccatgg gaatccgttt cattattatg gtaacaatat ggagtgctgt attcctaaac     240
tcattattca accaagaagt tcaaattccc ttgaccgaaa gttactgtgg cccatgtcct     300
aaaaactgga tatgttacaa aataactgc taccaatttt ttgatgagag taaaaactgg     360
tatgagagcc aggcttcttg tatgtctcaa aatgccagcc ttctgaaagt atacagcaaa     420
gaggaccagg atttacttaa actggtgaag tcatatcatt ggatgggact agtacacatt     480
ccaacaaatg gatcttggca gtgggaagat ggctccattc tctcacccaa cctactaaca     540
ataattgaaa tgcagaaggg agactgtgca ctctatgcct cgagctttaa aggctatata     600
gaaaactgtt caactccaaa tacgtacatc tgcatgcaaa ggactgtg              648

<210> SEQ ID NO 3
<211> LENGTH: 21
<212> TYPE: PRT
<213> ORGANISM: Artificial Sequence
<220> FEATURE:
<223> OTHER INFORMATION: The sequence is designed and synthesized

<400> SEQUENCE: 3

Met Ala Leu Pro Val Thr Ala Leu Leu Leu Pro Leu Ala Leu Leu Leu
1               5                   10                  15

His Ala Ala Arg Pro
            20

<210> SEQ ID NO 4
<211> LENGTH: 119
<212> TYPE: PRT
<213> ORGANISM: Artificial Sequence
<220> FEATURE:
<223> OTHER INFORMATION: The sequence is designed and synthesized

<400> SEQUENCE: 4

Pro Cys Pro Lys Asn Trp Ile Cys Tyr Lys Asn Asn Cys Tyr Gln Phe
1               5                   10                  15

Phe Asp Glu Ser Lys Asn Trp Tyr Glu Ser Gln Ala Ser Cys Met Ser
            20                  25                  30
```

Gln Asn Ala Ser Leu Leu Lys Val Tyr Ser Lys Glu Asp Gln Asp Leu
            35                  40                  45

Leu Lys Leu Val Lys Ser Tyr His Trp Met Gly Leu Val His Ile Pro
 50                  55                  60

Thr Asn Gly Ser Trp Gln Trp Glu Asp Gly Ser Ile Leu Ser Pro Asn
 65                  70                  75                  80

Leu Leu Thr Ile Ile Glu Met Gln Lys Gly Asp Cys Ala Leu Tyr Ala
                85                  90                  95

Ser Ser Phe Lys Gly Tyr Ile Glu Asn Cys Ser Thr Pro Asn Thr Tyr
            100                 105                 110

Ile Cys Met Gln Arg Thr Val
            115

<210> SEQ ID NO 5
<211> LENGTH: 136
<212> TYPE: PRT
<213> ORGANISM: Artificial Sequence
<220> FEATURE:
<223> OTHER INFORMATION: The sequence is designed and synthesized

<400> SEQUENCE: 5

Ser Leu Phe Asn Gln Glu Val Gln Ile Pro Leu Thr Glu Ser Tyr Cys
 1               5                  10                  15

Gly Pro Cys Pro Lys Asn Trp Ile Cys Tyr Lys Asn Asn Cys Tyr Gln
            20                  25                  30

Phe Phe Asp Glu Ser Lys Asn Trp Tyr Glu Ser Gln Ala Ser Cys Met
            35                  40                  45

Ser Gln Asn Ala Ser Leu Leu Lys Val Tyr Ser Lys Glu Asp Gln Asp
 50                  55                  60

Leu Leu Lys Leu Val Lys Ser Tyr His Trp Met Gly Leu Val His Ile
 65                  70                  75                  80

Pro Thr Asn Gly Ser Trp Gln Trp Glu Asp Gly Ser Ile Leu Ser Pro
                85                  90                  95

Asn Leu Leu Thr Ile Ile Glu Met Gln Lys Gly Asp Cys Ala Leu Tyr
            100                 105                 110

Ala Ser Ser Phe Lys Gly Tyr Ile Glu Asn Cys Ser Thr Pro Asn Thr
            115                 120                 125

Tyr Ile Cys Met Gln Arg Thr Val
            130                 135

<210> SEQ ID NO 6
<211> LENGTH: 152
<212> TYPE: PRT
<213> ORGANISM: Artificial Sequence
<220> FEATURE:
<223> OTHER INFORMATION: The sequence is designed and synthesized

<400> SEQUENCE: 6

Ile Arg Phe Ile Ile Met Val Thr Ile Trp Ser Ala Val Phe Leu Asn
 1               5                  10                  15

Ser Leu Phe Asn Gln Glu Val Gln Ile Pro Leu Thr Glu Ser Tyr Cys
            20                  25                  30

Gly Pro Cys Pro Lys Asn Trp Ile Cys Tyr Lys Asn Asn Cys Tyr Gln
            35                  40                  45

Phe Phe Asp Glu Ser Lys Asn Trp Tyr Glu Ser Gln Ala Ser Cys Met
            50                  55                  60

Ser Gln Asn Ala Ser Leu Leu Lys Val Tyr Ser Lys Glu Asp Gln Asp

```
              65                  70                  75                  80
Leu Leu Lys Leu Val Lys Ser Tyr His Trp Met Gly Leu Val His Ile
                    85                  90                  95

Pro Thr Asn Gly Ser Trp Gln Trp Glu Asp Gly Ser Ile Leu Ser Pro
                100                 105                 110

Asn Leu Leu Thr Ile Ile Glu Met Gln Lys Gly Asp Cys Ala Leu Tyr
                115                 120                 125

Ala Ser Ser Phe Lys Gly Tyr Ile Glu Asn Cys Ser Thr Pro Asn Thr
            130                 135                 140

Tyr Ile Cys Met Gln Arg Thr Val
145                 150

<210> SEQ ID NO 7
<211> LENGTH: 170
<212> TYPE: PRT
<213> ORGANISM: Artificial Sequence
<220> FEATURE:
<223> OTHER INFORMATION: The sequence is designed and synthesized

<400> SEQUENCE: 7

Arg Glu Asn Ala Ser Pro Phe Phe Cys Cys Phe Ile Ala Val Ala
1               5                   10                  15

Met Gly Ile Arg Phe Ile Ile Met Val Thr Ile Trp Ser Ala Val Phe
                20                  25                  30

Leu Asn Ser Leu Phe Asn Gln Glu Val Gln Ile Pro Leu Thr Glu Ser
                35                  40                  45

Tyr Cys Gly Pro Cys Pro Lys Asn Trp Ile Cys Tyr Lys Asn Asn Cys
            50                  55                  60

Tyr Gln Phe Phe Asp Glu Ser Lys Asn Trp Tyr Glu Ser Gln Ala Ser
65                  70                  75                  80

Cys Met Ser Gln Asn Ala Ser Leu Leu Lys Val Tyr Ser Lys Glu Asp
                85                  90                  95

Gln Asp Leu Leu Lys Leu Val Lys Ser Tyr His Trp Met Gly Leu Val
                100                 105                 110

His Ile Pro Thr Asn Gly Ser Trp Gln Trp Glu Asp Gly Ser Ile Leu
                115                 120                 125

Ser Pro Asn Leu Leu Thr Ile Ile Glu Met Gln Lys Gly Asp Cys Ala
            130                 135                 140

Leu Tyr Ala Ser Ser Phe Lys Gly Tyr Ile Glu Asn Cys Ser Thr Pro
145                 150                 155                 160

Asn Thr Tyr Ile Cys Met Gln Arg Thr Val
                165                 170

<210> SEQ ID NO 8
<211> LENGTH: 216
<212> TYPE: PRT
<213> ORGANISM: Artificial Sequence
<220> FEATURE:
<223> OTHER INFORMATION: The sequence is designed and synthesized

<400> SEQUENCE: 8

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
                35                  40                  45
```

```
Asn Ala Ser Pro Phe Phe Cys Cys Phe Ile Ala Val Ala Met Gly
    50              55                  60

Ile Arg Phe Ile Ile Met Val Thr Ile Trp Ser Ala Val Phe Leu Asn
65              70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Thr Ile Ile Glu Met Gln Lys Gly Asp Cys Ala Leu Tyr
            180                 185                 190       Tyr

Ala Ser Ser Phe Lys Gly Tyr Ile Glu Asn Cys Ser Thr Pro Asn Thr
        195                 200                 205

Tyr Ile Cys Met Gln Arg Thr Val
    210                 215
```

```
<210> SEQ ID NO 9
<211> LENGTH: 145
<212> TYPE: PRT
<213> ORGANISM: Artificial Sequence
<220> FEATURE:
<223> OTHER INFORMATION: The sequence is designed and synthesized

<400> SEQUENCE: 9

Thr Ile Trp Ser Ala Val Phe Leu Asn Ser Leu Phe Asn Gln Glu Val
1               5                   10                  15

Gln Ile Pro Leu Thr Glu Ser Tyr Cys Gly Pro Cys Pro Lys Asn Trp
            20                  25                  30

Ile Cys Tyr Lys Asn Asn Cys Tyr Gln Phe Phe Asp Glu Ser Lys Asn
        35                  40                  45

Trp Tyr Glu Ser Gln Ala Ser Cys Met Ser Gln Asn Ala Ser Leu Leu
50                  55                  60

Lys Val Tyr Ser Lys Glu Asp Gln Asp Leu Leu Lys Leu Val Lys Ser
65                  70                  75                  80

Tyr His Trp Met Gly Leu Val His Ile Pro Thr Asn Gly Ser Trp Gln
            85                  90                  95

Trp Glu Asp Gly Ser Ile Leu Ser Pro Asn Leu Thr Ile Ile Glu
        100                 105                 110

Met Gln Lys Gly Asp Cys Ala Leu Tyr Ala Ser Ser Phe Lys Gly Tyr
    115                 120                 125

Ile Glu Asn Cys Ser Thr Pro Asn Thr Tyr Ile Cys Met Gln Arg Thr
    130                 135                 140

Val
145

<210> SEQ ID NO 10
<211> LENGTH: 45
<212> TYPE: PRT
<213> ORGANISM: Artificial Sequence
<220> FEATURE:
```

<223> OTHER INFORMATION: The sequence is designed and synthesized

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 11
<211> LENGTH: 24
<212> TYPE: PRT
<213> ORGANISM: Artificial Sequence
<220> FEATURE:
<223> OTHER INFORMATION: The sequence is designed and synthesized

<400> SEQUENCE: 11

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 12
<211> LENGTH: 42
<212> TYPE: PRT
<213> ORGANISM: Artificial Sequence
<220> FEATURE:
<223> OTHER INFORMATION: The sequence is designed and synthesized

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 13
<211> LENGTH: 107
<212> TYPE: PRT
<213> ORGANISM: Artificial Sequence
<220> FEATURE:
<223> OTHER INFORMATION: The sequence is designed and synthesized

<400> SEQUENCE: 13

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val Arg Ser Lys Arg Ser Arg Leu Leu His Ser Asp Tyr Met Asn
65              70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 14
<211> LENGTH: 112
<212> TYPE: PRT
<213> ORGANISM: Artificial Sequence
<220> FEATURE:
<223> OTHER INFORMATION: The sequence is designed and synthesized

<400> SEQUENCE: 14

```
Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 15
<211> LENGTH: 112
<212> TYPE: PRT
<213> ORGANISM: Artificial Sequence
<220> FEATURE:
<223> OTHER INFORMATION: The sequence is designed and synthesized

<400> SEQUENCE: 15

```
Arg Val Lys Phe Ser Arg Ser Ala Asp Ala Pro Ala Tyr Lys Gln Gly
1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 16
<211> LENGTH: 63
<212> TYPE: DNA
<213> ORGANISM: Artificial Sequence
<220> FEATURE:
<223> OTHER INFORMATION: The sequence is designed and synthesized

<400> SEQUENCE: 16

```
atggccctgc ccgtcaccgc tctgctgctg ccccttgctc tgcttcttca tgcagcaagg    60
ccg                                                                  63
```

<210> SEQ ID NO 17
<211> LENGTH: 357

```
<212> TYPE: DNA
<213> ORGANISM: Artificial Sequence
<220> FEATURE:
<223> OTHER INFORMATION: The sequence is designed and synthesized

<400> SEQUENCE: 17
ccctgcccaa agaactggat atgttacaaa ataattgct accagttttt cgacgagtcc      60
aagaattggt atgaatcaca agccagctgc atgtcccaaa atgcgtcatt gttgaaggta    120
tattctaagg aggaccaaga tttgttgaag ttggttaaat cctatcattg gatggggttg    180
gtccatatac ctacaaatgg ttcatggcag tgggaagatg gatctatact gagcccaaat    240
cttctgacaa taattgaaat gcaaaaaggc gattgtgccc tttacgctag tagcttcaaa    300
ggttatattg agaactgtag cacaccgaac acttatatct gtatgcagag aacggtt       357

<210> SEQ ID NO 18
<211> LENGTH: 408
<212> TYPE: DNA
<213> ORGANISM: Artificial Sequence
<220> FEATURE:
<223> OTHER INFORMATION: The sequence is designed and synthesized

<400> SEQUENCE: 18
tctctgttca accaagaggt gcagatacca cttaccgaat catattgtgg ccctgccca      60 aagaactgga tatgttacaa aataattgc taccagtttt tcgacgagtc caagaattgg    120
tatgaatcac aagccagctg catgtcccaa aatgcgtcat tgttgaaggt atattctaag    180
gaggaccaag atttgttgaa gttggttaaa tcctatcatt ggatgggtt ggtccatata    240 cctacaaatg gttcatggca gtgggaagat ggatctatac tgagcccaaa tcttctgaca    300
ataattgaaa tgcaaaaagg cgattgtgcc ctttacgcta gtagcttcaa aggttatatt    360
gagaactgta gcacaccgaa cacttatatc tgtatgcaga gaacggtt                 408

<210> SEQ ID NO 19
<211> LENGTH: 456
<212> TYPE: DNA
<213> ORGANISM: Artificial Sequence
<220> FEATURE:
<223> OTHER INFORMATION: The sequence is designed and synthesized

<400> SEQUENCE: 19
attaggttta ttattatggt cacaatatgg tctgccgtat ttctcaactc tctgttcaac     60
caagaggtgc agataccact taccgaatca tattgtggcc cctgcccaaa gaactggata   120
tgttacaaaa ataattgcta ccagtttttc gacgagtcca agaattggta tgaatcacaa   180
gccagctgca tgtcccaaaa tgcgtcattg ttgaaggtat attctaagga ggaccaagat   240
ttgttgaagt tggttaaatc ctatcattgg atgggttgg tccatatacc tacaaatggt   300
tcatggcagt gggaagatgg atctatactg agcccaaatc ttctgacaat aattgaaatg   360
caaaaaggcg attgtgccct ttacgctagt agcttcaaag gttatattga gaactgtagc   420
acaccgaaca cttatatctg tatgcagaga acggtt                             456

<210> SEQ ID NO 20
<211> LENGTH: 510
<212> TYPE: DNA
<213> ORGANISM: Artificial Sequence
<220> FEATURE:
<223> OTHER INFORMATION: The sequence is designed and synthesized

<400> SEQUENCE: 20
```

```
agagaaaatg ctagtccctt tttcttctgt tgctttattg cggtcgcaat ggggattagg      60
tttattatta tggtcacaat atggtctgcc gtatttctca actctctgtt caaccaagag     120
gtgcagatac cacttaccga atcatattgt ggccctgcc caaagaactg gatatgttac     180
aaaaataatt gctaccagtt tttcgacgag tccaagaatt ggtatgaatc acaagccagc     240
tgcatgtccc aaaatgcgtc attgttgaag gtatattcta aggaggacca agatttgttg     300
aagttggtta aatcctatca ttggatgggg ttggtccata tacctacaaa tggttcatgg     360
cagtgggaag atggatctat actgagccca aatcttctga caataattga aatgcaaaaa     420
ggcgattgtg cctttacgc tagtagcttc aaaggttata ttgagaactg tagcacaccg     480
aacacttata tctgtatgca gagaacggtt                                      510
```

<210> SEQ ID NO 21
<211> LENGTH: 648
<212> TYPE: DNA
<213> ORGANISM: Artificial Sequence
<220> FEATURE:
<223> OTHER INFORMATION: The sequence is designed and synthesized

<400> SEQUENCE: 21

```
atggggtgga ttcgtggtcg gaggtctcga cacagctggg agatgagtga atttcataat      60
tataacttgg atctgaagaa gagtgatttt tcaacacgat ggcaaaagca agatgtcca     120 gtagtcaaaa gcaaatgtag agaaaatgca tctccatttt ttttctgctg cttcatcgct     180
gtagccatgg gaatccgttt cattattatg gtaacaatat ggagtgctgt attcctaaac     240
tcattattca accaagaagt tcaaattccc ttgaccgaaa gttactgtgg cccatgtcct     300
aaaaactgga tatgttacaa aaataactgc taccaatttt ttgatgagag taaaaactgg     360
tatgagagcc aggcttcttg tatgtctcaa aatgccagcc ttctgaaagt atacagcaaa     420
gaggaccagg atttacttaa actggtgaag tcatatcatt ggatgggact agtacacatt     480
ccaacaaatg gatcttggca gtgggaagat ggctccattc tctcacccaa cctactaaca     540
ataattgaaa tgcagaaggg agactgtgca ctctatgcct cgagctttaa aggctatata     600
gaaaactgtt caactccaaa tacgtacatc tgcatgcaaa ggactgtg               648
```

<210> SEQ ID NO 22
<211> LENGTH: 435
<212> TYPE: DNA
<213> ORGANISM: Artificial Sequence
<220> FEATURE:
<223> OTHER INFORMATION: The sequence is designed and synthetized

<400> SEQUENCE: 22

```
acaatatgga gtgctgtatt cctaaactca ttattcaacc aagaagttca aattcccttg      60
accgaaagtt actgtggccc atgtcctaaa aactggatat gttacaaaaa taactgctac     120 caatttttg atgagagtaa aaactggtat gagagccagg cttcttgtat gtctcaaaat     180
gccagccttc tgaaagtata cagcaaagag gaccaggatt tacttaaact ggtgaagtca     240
tatcattgga tgggactagt acacattcca acaaatggat cttggcagtg ggaagatggc     300
tccattctct cacccaacct actaacaata attgaaatgc agaagggaga ctgtgcactc     360
tatgcctcga gctttaaagg ctatatagaa aactgttcaa ctccaaatac gtacatctgc     420
atgcaaagga ctgtg                                                      435
```

<210> SEQ ID NO 23
<211> LENGTH: 135

<212> TYPE: DNA
<213> ORGANISM: Artificial Sequence
<220> FEATURE:
<223> OTHER INFORMATION: The sequence is designed and synthetized

<400> SEQUENCE: 23
accacgacgc cagcgccgcg accaccaaca ccggcgccca ccatcgcgtc gcagcccctg    60
tccctgcgcc cagaggcgtg ccggccagcg gcggggggcg cagtgcacac gaggggggctg   120 gacttcgcct gtgat                                                    135

<210> SEQ ID NO 24
<211> LENGTH: 72
<212> TYPE: DNA
<213> ORGANISM: Artificial Sequence
<220> FEATURE:
<223> OTHER INFORMATION: The sequence is designed and synthetized

<400> SEQUENCE: 24
atctacatct gggcgccctt ggccgggact tgtggggtcc ttctcctgtc actggttatc    60 acccttact gc                                                         72

<210> SEQ ID NO 25
<211> LENGTH: 126
<212> TYPE: DNA
<213> ORGANISM: Artificial Sequence
<220> FEATURE:
<223> OTHER INFORMATION: The sequence is designed and synthetized

<400> SEQUENCE: 25
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 26
<211> LENGTH: 321
<212> TYPE: DNA
<213> ORGANISM: Artificial Sequence
<220> FEATURE:
<223> OTHER INFORMATION: The sequence is designed and synthetized

<400> SEQUENCE: 26
attgaagtta tgtatcctcc tccttaccta gacaatgaga agagcaatgg aaccattatc    60
catgtgaaag ggaaacacct ttgtccaagt cccctatttc ccggaccttc taagcccttt   120
tgggtgctgg tggtggttgg gggagtcctg gcttgctata gcttgctagt aacagtggcc   180
tttattattt tctgggtgag gagtaagagg agcaggctcc tgcacagtga ctacatgaac   240
atgactcccc gccgcccgg gcccaccccgc aagcattacc agccctatgc cccaccacgc   300
gacttcgcag cctatcgctc c                                             321

<210> SEQ ID NO 27
<211> LENGTH: 336
<212> TYPE: DNA
<213> ORGANISM: Artificial Sequence
<220> FEATURE:
<223> OTHER INFORMATION: The sequence is designed and synthetized

<400> SEQUENCE: 27
agagtgaagt tcagcaggag cgcagacgcc ccgcgtacc agcagggcca gaaccagctc    60
tataacgagc tcaatctagg acgaagagag gagtacgatg ttttggacaa gagacgtggc   120

| | |
|---|---|
| cgggaccctg agatgggggg aaagccgaga aggaagaacc ctcaggaagg cctgtacaat | 180 |
| gaactgcaga aagataagat ggcggaggcc tacagtgaga ttgggatgaa aggcgagcgc | 240 |
| cggaggggca aggggcacga tggcctttac cagggtctca gtacagccac caaggacacc | 300 |
| tacgacgccc ttcacatgca ggccctgccc cctcgc | 336 |

<210> SEQ ID NO 28
<211> LENGTH: 336
<212> TYPE: DNA
<213> ORGANISM: Artificial Sequence
<220> FEATURE:
<223> OTHER INFORMATION: The sequence is designed and synthetized

<400> SEQUENCE: 28

| | |
|---|---|
| agagtgaagt tcagcaggag cgcagacgcc cccgcgtaca agcagggcca gaaccagctc | 60 |
| tataacgagc tcaatctagg acgaagagag gagtacgatg tttttggacaa gagacgtggc | 120 |
| cgggaccctg agatgggggg aaagccgaga aggaagaacc ctcaggaagg cctgtacaat | 180 |
| gaactgcaga aagataagat ggcggaggcc tacagtgaga ttgggatgaa aggcgagcgc | 240 |
| cggaggggca aggggcacga tggcctttac cagggtctca gtacagccac caaggacacc | 300 |
| tacgacgccc ttcacatgca ggccctgccc cctcgc | 336 |

<210> SEQ ID NO 29
<211> LENGTH: 1259
<212> TYPE: DNA
<213> ORGANISM: Artificial Sequence
<220> FEATURE:
<223> OTHER INFORMATION: The sequence is designed and synthetized

<400> SEQUENCE: 29

| | |
|---|---|
| tgcaaagatg gataaagttt taaacagaga ggaatctttg cagctaatgg accttctagg | 60 |
| tcttgaaagg agtgggaatt ggctccggtg cccgtcagtg ggcagagcgc acatcgccca | 120 |
| cagtccccga gaagttgggg ggaggggtcg gcaattgatc cggtgcctag agaaggtggc | 180 |
| gcggggtaaa ctgggaaagt gatgtcgtgt actggctccg cctttttccc gagggtgggg | 240 |
| gagaaccgta tataagtgca gtagtcgccg tgaacgttct ttttcgcaac gggtttgccg | 300 |
| ccagaacaca ggtaagtgcc gtgtgtggtt cccgcgggcc tggcctcttt acgggttatg | 360 |
| gcccttgcgt gccttgaatt acttccacct ggctgcagta cgtgattctt gatcccgagc | 420 |
| ttcgggttgg aagtgggtgg agagttcga ggccttgcgc ttaaggagcc ccttcgcctc | 480 |
| gtgcttgagt tgaggcctgg cctgggcgct ggggccgccg cgtgcgaatc tggtggcacc | 540 |
| ttcgcgcctg tctcgctgct ttcgataagt ctctagccat ttaaaatttt tgatgacctg | 600 |
| ctgcgacgct ttttttctgg caagatagtc ttgtaaatgc gggccaagat ctgcacactg | 660 |
| gtatttcggt ttttggggcc gcgggcggcg acggggcccg tgcgtcccag cgcacatgtt | 720 |
| cggcgaggcg gggcctgcga gcgcggccac cgagaatcgg acggggggtag tctcaagctg | 780 |
| gccggcctgc tctggtgcct ggcctcgcgc cgccgtgtat cgccccgccc tgggcggcaa | 840 |
| ggctggcccg gtcggcacca gttgcgtgag cggaaagatg gccgcttccc ggccctgctg | 900 |
| cagggagctc aaaatggagg acgcggcgct cgggagagcg ggcgggtgag tcacccacac | 960 |
| aaaggaaaag ggcctttccg tcctcagccg tcgcttcatg tgactccacg gagtaccggg | 1020 |
| cgccgtccag gcacctcgat tagttctcga gcttttggag tacgtcgtct ttaggttggg | 1080 |
| gggaggggtt ttatgcgatg gagtttcccc acactgagtg ggtggagact gaagttaggc | 1140 |
| cagcttggca cttgatgtaa ttctccttgg aatttgccct ttttgagttt ggatcttggt | 1200 |

```
<210> SEQ ID NO 30
<211> LENGTH: 256
<212> TYPE: DNA
<213> ORGANISM: Artificial Sequence
<220> FEATURE:
<223> OTHER INFORMATION: The sequence is designed and synthetized

<400> SEQUENCE: 30
taggtcttga aaggagtggg aattggctcc ggtgcccgtc agtgggcaga gcgcacatcg    60
cccacagtcc ccgagaagtt gggggagggg gtcggcaatt gatccggtgc ctagagaagg   120
tggcgcgggg taaactggga aagtgatgtc gtgtactggc tccgcctttt tcccgagggt   180
gggggagaac cgtatataag tgcagtagtc gccgtgaacg ttctttttcg caacgggttt   240
gccgccagaa cacagg                                                   256

<210> SEQ ID NO 31
<211> LENGTH: 63
<212> TYPE: DNA
<213> ORGANISM: Artificial Sequence
<220> FEATURE:
<223> OTHER INFORMATION: The sequence is designed and synthetized

<400> SEQUENCE: 31
cactttggcg ccggctcgag ggggcccggg tgcaaagatg gataaagttt aaacagaga     60 gga                                                                  63

<210> SEQ ID NO 32
<211> LENGTH: 60
<212> TYPE: DNA
<213> ORGANISM: Artificial Sequence
<220> FEATURE:
<223> OTHER INFORMATION: The sequence is designed and synthetized

<400> SEQUENCE: 32
cactttggcg ccggctcgag ggggcccggg taggtcttga aaggagtggg aattggctcc    60

<210> SEQ ID NO 33
<211> LENGTH: 59
<212> TYPE: DNA
<213> ORGANISM: Artificial Sequence
<220> FEATURE:
<223> OTHER INFORMATION: The sequence is designed and synthetized

<400> SEQUENCE: 33
tccagaggtt gattgtcgac ttaacgcgtt tagcgagggg gcagggcctg catgtgaag     59
```

(also line above: tcattctcaa gcctcagaca gtggttcaaa gttttttct tccatttcag gtgtcgtga 1259)

What is claimed is:

1. A chimeric antigen receptor targeting human NKG2DL, wherein
an amino acid sequence of the chimeric antigen receptor targeting the human NKG2DL is sequentially connected by the following amino acid sequences from an amino terminal to a carboxy terminal: an amino acid sequence of a guiding sequence shown as SEQ ID No.3, an amino acid sequence of human NKG2D shown as SEQ ID No.4, an amino acid sequence of a human CD8 hinge region shown as SEQ ID No.10, an amino acid sequence of a human CD8 transmembrane region shown as SEQ ID No.11, an amino acid sequence of a human 4-1BB intracellular domain shown as SEQ ID No.12 and an amino acid sequence of a human CD3 zeta domain shown as SEQ ID No.14.

2. A nucleic acid molecule encoding the chimeric antigen receptor targeting the human NKG2DL according to claim 1, wherein a nucleotide sequence of the nucleic acid molecule is sequentially connected by the following nucleotide sequences from 5' to 3': a nucleotide sequence encoding the guiding sequence shown as SEQ ID NO.16, a nucleotide sequence encoding the human NKG2D shown as SEQ ID NO.17, a nucleotide sequence encoding the human CD8 hinge region shown as SEQ ID NO.23, a nucleotide sequence encoding the human CD8 transmembrane region shown as SEQ ID NO.24, a nucleotide sequence encoding the human 4-1BB intracellular domain shown as SEQ ID No.25 and a nucleotide sequence encoding the human CD3 zeta domain shown as SEQ ID No.27.

3. A recombinant vector, comprising the nucleic acid molecule according to claim 2.

4. A recombinant virus, comprising the recombinant vector according to claim 3, wherein the recombinant virus comprises lentivirus, adenovirus, adeno associated virus or retrovirus.

5. A chimeric antigen receptor targeting human NKG2DL modified immune cell, wherein the chimeric antigen receptor targeting the human NKG2DL modified immune cell is obtained by infecting an immune cell using the recombinant virus according to claim 4; wherein
the immune cell comprises a T cell, a natural killer (NK) cell or a pluripotent stem cell, and the pluripotent stein cell is differentiated into a lymphoid cell.

6. A method of preparing a pharmaceutical composition comprising the chimeric antigen receptor targeting the human NKG2DL modified immune cell according to claim 5, wherein the pharmaceutical composition is used for treating a cancer.

7. The method according to claim 6, wherein the cancer is configured to express the human NKG2DL protein, and the cancer comprises liver cancer, glioblastoma, ovarian cancer, gastric cancer, medulloblastoma, pancreatic cancer, lung cancer, prostate cancer, breast cancer, neuroblastoma, bladder cancer, colon cancer, renal cell carcinoma, leukemia, lymphoma, multiple myeloma or melanoma.

* * * * *